(12) United States Patent
Toriyabe et al.

(10) Patent No.: US 7,767,626 B2
(45) Date of Patent: Aug. 3, 2010

(54) 3-ARYLPHENYL SULFIDE DERIVATIVE AND INSECTICIDE AND MITICIDE

(75) Inventors: Keiji Toriyabe, Aomori (JP); Nobuo Takefuji, Shizuoka (JP); Minoru Itou, Shizuoka (JP); Tetsuya Hirade, Shizuoka (JP); Kiyotoshi Nishiyama, Shizuoka (JP); Mitsuharu Asahida, Iwate (JP); Yasunobu Maeda, Chiba (JP); Nobuhide Wada, Shizuoka (JP); Toyokazu Fujisawa, Nagano (JP); Hiroyuki Yano, Shizuoka (JP); Masaaki Komatsu, Shizuoka (JP); Osamu Tada, Shizuoka (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 12/269,549

(22) Filed: Nov. 12, 2008

(65) Prior Publication Data

US 2009/0170883 A1 Jul. 2, 2009

Related U.S. Application Data

(62) Division of application No. 11/098,440, filed on Apr. 5, 2005, now Pat. No. 7,612,105, which is a division of application No. 10/981,722, filed on Nov. 5, 2004, now Pat. No. 7,037,930, which is a division of application No. 10/121,833, filed on Apr. 15, 2002, now Pat. No. 6,858,639, which is a division of application No. 09/673,633, filed as application No. PCT/JP99/02212 on Apr. 26, 1999, now Pat. No. 6,509,354.

(30) Foreign Application Priority Data

| Apr. 27, 1998 | (JP) | ................................ 10-132768 |
| Sep. 18, 1998 | (JP) | ................................ 10-283539 |
| Oct. 30, 1998 | (JP) | ................................ 10-309580 |

(51) Int. Cl.
*C07D 333/08* (2006.01)
*A01N 43/00* (2006.01)
(52) U.S. Cl. ........................................ 504/289; 549/83
(58) Field of Classification Search .................... 549/83; 504/289; 514/438
See application file for complete search history.

(56) References Cited

U.S. PATENT DOCUMENTS

| 3,778,443 A | 12/1973 | Arya |
| 3,185,689 A | 3/1979 | Schwindt et al. |
| 4,146,688 A | 3/1979 | Schwindt et al. |
| 4,748,245 A | 5/1988 | James |
| 5,292,879 A * | 3/1994 | DiNinno et al. ............. 540/302 |
| 5,554,580 A | 9/1996 | Fischer et al. |

FOREIGN PATENT DOCUMENTS

| JP | 48-66621 | 9/1973 |
| JP | 52-118484 | 9/1977 |
| JP | 53-28697 | 3/1978 |
| JP | 58-128381 | 7/1983 |
| JP | 58-194866 | 11/1983 |
| JP | 59-98004 | 6/1984 |
| JP | 62-48649 | 3/1987 |
| JP | 1-250374 | 10/1989 |
| JP | 2-184675 | 7/1990 |
| JP | 4-297477 | 10/1992 |
| JP | 7-76578 | 3/1995 |
| JP | 8-500835 | 1/1996 |
| WO | WO 87/03781 | 7/1987 |
| WO | WO 89/11279 | 11/1989 |
| WO | WO 97/01541 | 1/1997 |

OTHER PUBLICATIONS

Tetrahedron Letters, 1994, 35(48), pp. 9063-9066.
Gupta, et al., Tetrahedron Letters, 1996, 37(16), pp. 2817-2820, 1996.
Noren, et al., Enviromental Health Perspective, 1996, 104, (7), pp. 766-772.
Benaskar, et al., Tetrahedron Letters, 1994, 35(11), pp. 1727-1730.

* cited by examiner

*Primary Examiner*—James O. Wilson
*Assistant Examiner*—Paul V. Ward
(74) *Attorney, Agent, or Firm*—Oblon, Spivak, McClelland, Maier & Neustadt, L.L.P.

(57) ABSTRACT

3-Arylphenyl sulfide derivatives represented by general formula (I):

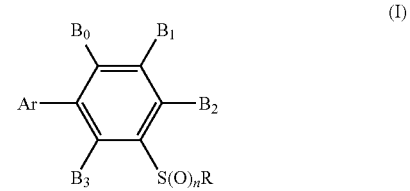

(wherein R is a $C_2$-$C_6$ alkyl group, a $C_2$-$C_6$ alkenyl group, a $C_2$-$C_6$ alkynyl group or the like, $B_0$ to $B_2$ and $B_3$ are hydrogen atoms, halogen atoms, cyano groups, $C_1$-$C_4$ haloalkyl groups or the like, n is 0, 1 or 2, and Ar is a phenyl ring, a pyridine ring, a thiophene ring, a pyrazole ring or the like), and insecticides and miticides containing the 3-arylphenyl sulfide derivatives as an active ingredient.

19 Claims, No Drawings

3-ARYLPHENYL SULFIDE DERIVATIVE AND INSECTICIDE AND MITICIDE

CROSS REFERENCE TO RELATED APPLICATION

This application is a divisional of U.S. application Ser. No. 11/098,440, filed on Apr. 5, 2005 now U.S. Pat. No. 7,612,105, which is a divisional of U.S. application Ser. No. 10/981,722, filed on Nov. 5, 2004 now U.S. Pat. No. 7,037,930, which is a divisional of U.S. application Ser. No. 10/121,833, filed on Apr. 15, 2002 now U.S. Pat. No. 6,858,639, which is a divisional of U.S. application Ser. No. 09/673,633, filed on Oct. 27, 2000 now U.S. Pat. No. 6,509,354, which is a 371 of PCT/JP99/002212, filed on Apr. 26, 1999, and claims priority to the following Japanese Patent Applications: 10-132768, filed on Apr. 27, 1998; 10-283539, filed on Sep. 18, 1998; and 10-309580, filed on Oct. 30, 1998.

TECHNICAL FIELD

The present invention relates to novel 3-arylphenyl sulfide derivatives and insecticides and miticides containing them as an active ingredient.

BACKGROUND ART

East German Patent No. 1425417 East German Patent No. 142542, JP-A-7-2655 and Tetrahedron vol. 39, p. 2289 (1983) and Tetrahedron Lett. vol. 25, 44, p. 5095 (1984) disclose 3-methylthiobiphenyl derivatives, and East German Patent No. 4323916 and International Patent Application WO95/02580 disclose 3-pyridylphenyl sulfide derivatives. However, none of them mention anything about insecticides or miticides. Also, International Patent Application WO96/06830, JP-A-2-184675, JP-A-60-233061, European Patent No. 152590, South African Patent No. 6800955 and German Patent No. 3316300 report 3-azorylphenyl sulfide derivatives but mention nothing about insecticides or miticides. On the other hand, use of 4-biphenyl sulfide derivatives as insecticides is reported, for example, in U.S. Pat. No. 3,442,955. However, the 3-arylphenyl sulfide derivatives of the present invention have not been known yet.

In recent years, some of the conventional commercial insecticides are restricted in their use in view of problems of persistency, accumulation and environmental pollution, and others have become less effective as the pest insects have acquired resistance during their use for a long period of time. Therefore, it has been desired to develop a new insecticide which is highly effective at a low dose and excellent in safety.

DISCLOSURE OF THE INVENTION

Under these circumstances, the present inventors have synthesized various 3-arylphenyl sulfide derivatives and have studied their physiological activities. As a result, it has been found that the compounds of the present invention exhibit outstanding effects on various pests, especially on farm and garden pests including mites represented by two-spotted spider mite, Kanzawa spider mite and citrus red mite, pest lepidopterans represented by diamondblackmoss, Asiatic rice borer and beat armyworm, pest hemipterans represented by brown rice planthopper, green rice leafhopper and cotton aphid and pest coleoptera represented by adzuki bean weevil. The present invention has been accomplished on the basis of this discovery.

That is, the present invention provides (1) 3-arylphenyl sulfide derivatives represented by general formula (I):

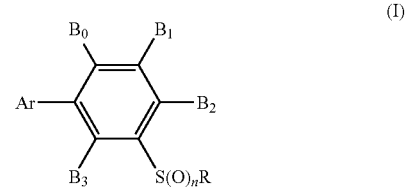

(wherein R is a $C_2$-$C_6$ alkyl group (which may be mono- or poly-substituted by halogen atoms or cyano groups), a $C_2$-$C_6$ alkenyl group (which may be mono- or poly-substituted by halogen atoms or cyano groups), a $C_2$-$C_6$ alkynyl group (which may be mono- or poly-substituted by halogen atoms or cyano groups), a $C_3$-$C_6$ cycloalkyl group (which may be mono- or poly-substituted by halogen atoms or cyano groups) or a $C_4$-$C_9$ cycloalkylalkyl group (which may be mono- or poly-substituted by halogen atoms or cyano groups), n is an integer of from 0 to 2, Ar is a group represented by any one of general formulae:

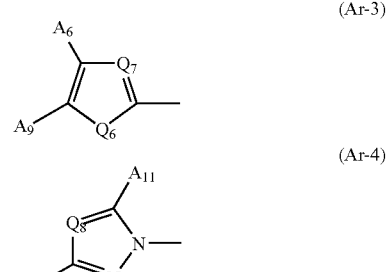

wherein $Q_1$, $Q_2$, $Q_3$, $Q_4$ and $Q_5$ are, respectively, a nitrogen atom or C-$A_1$, a nitrogen atom or C-$A_2$, a nitrogen atom or C-$A_3$, a nitrogen atom or C-$A_4$, and a nitrogen atom or C-$A_5$, $Q_6$ is an oxygen atom or a sulfur atom, $Q_7$ is a nitrogen atom or C-$A_7$, $Q_8$ is a nitrogen atom or C-$A_8$, $A_1$, $A_5$, $A_7$, $A_{11}$ and $B_0$ are hydrogen atoms, halogen atoms, amino groups, cyano groups, nitro groups, $C_1$-$C_6$ alkyl groups, $C_1$-$C_4$ haloalkyl groups, $C_1$-$C_6$ alkylthio groups (which may be mono- or poly-substituted by halogen atoms) or $C_1$-$C_6$ alkoxy groups, $A_2$, $A_3$, $A_4$, $A_6$, $A_9$, $B_1$, $B_2$ and $B_3$ are hydrogen atoms, halogen atoms, cyano groups, nitro groups, $C_1$-$C_6$ alkyl groups (which may be mono- or poly-substituted by halogen atoms, hydroxyl groups, cyano groups, $C_2$-$C_7$ alkoxycarbonyl groups or $C_1$-$C_6$ alkoxy groups), $C_2$-$C_6$ alkenyl groups (which may be mono- or poly-substituted by halogen atoms or cyano groups), $C_2$-$C_6$ alkynyl groups (which may be mono- or poly-substituted by halogen atoms or cyano groups), $C_1$-$C_6$ alkoxy groups (which may be mono- or polysubstituted by halogen atoms, cyano groups, $C_2$-$C_5$ alkoxycarbonyl groups or $C_1$-$C_3$ alkoxy groups), $C_1$-$C_6$ alkylthio groups (which may be mono- or poly-substituted by halogen atoms or $C_1$-$C_3$ alkoxy groups), $C_1$-$C_6$ alkylsulfinyl groups (which may be mono- or poly-substituted by halogen atoms or $C_1$-$C_3$ alkoxy groups), $C_1$-$C_6$ alkylsulfonyl groups (which may be mono- or poly-substituted by halogen atoms or $C_1$-$C_3$ alkoxy groups), $C_1$-$C_7$ acyl groups, $C_2$-$C_5$ haloalkylcarbonyl groups, carboxyl groups, $C_2$-$C_7$ alkoxycarbonyl groups or $NR_1R_2$ [wherein $R_1$ and $R_2$ are independently hydrogen atoms, $C_1$-$C_6$ alkyl groups (which may be mono- or poly-substituted by halogen atoms, cyano groups, hydroxyl groups, $C_1$-$C_6$ alkoxy groups or $C_1$-$C_6$ alkylthio groups), $C_2$-$C_6$ alkenyl groups (which may be mono- or poly-substituted by halogen atoms or cyano groups), $C_2$-$C_6$ alkynyl groups (which may be mono- or poly-substituted by halogen atoms or cyano groups), $C_1$-$C_7$ acyl groups or $C_2$-$C_7$ alkoxycarbonyl groups or may form a 5 to 6-membered ring together with the nitrogen atom attached thereto], $A_8$ is a hydrogen atom, a halogen atom, a cyano group, a $C_1$-$C_6$ alkyl group (which may be mono- or poly-substituted by halogen atoms or $C_1$-$C_3$ alkoxy groups), a $C_1$-$C_6$ alkoxy group (which may be mono- or poly-substituted by halogen atoms or $C_1$-$C_3$ alkoxy groups), a $C_1$-$C_7$ acyl group, a $C_2$-$C_5$ haloalkylcarbonyl group or $NR_1R_2$ (wherein $R_1$ and $R_2$ are the same as defined above), and $A_{10}$ is a hydrogen atom, a $C_1$-$C_6$ alkyl group (which may be mono- or poly-substituted by halogen atoms or $C_1$-$C_3$ alkoxy groups), a $C_1$-$C_7$ acyl group, a $C_2$-$C_5$ haloalkylcarbonyl group, a carboxyl group or a $C_2$-$C_7$ alkoxycarbonyl group; provided that when Ar is represented by general formula (Ar-1) or (Ar-2), not more than three of $Q_1$-$Q_5$ are nitrogen atoms; when Ar is represented by general formula (Ar-1) wherein only $Q_5$ is a nitrogen atom, $A_1$ is a hydrogen atom; when Ar is represented by general formula (Ar-1) wherein $Q_1$, $Q_2$, $Q_3$, $Q_4$ and $Q_5$ are, respectively, C-$A_1$, C-$A_2$, C-$A_3$, C-$A_4$ and C-$A_5$, $A_2$, $A_3$, $A_4$ and $B_2$ are not simultaneously hydrogen atoms; when all of $A_1$ to $A_5$ are hydrogen atoms, compounds wherein $B_2$ is a methyl group, and R is an isopropyl are excluded; and when Ar is represented by general formula (Ar-4) wherein $Q_8$ is C-$A_8$, R is a $C_2$-$C_6$ alkyl group (which may be mono- or poly-substituted by halogen atoms), a $C_3$-$C_6$ cycloalkyl group (which may be mono- or poly-substituted by halogen atoms) or a $C_4$-$C_9$ cycloalkylalkyl group (which may be mono- or poly-substituted by halogen atoms)), (2) insecticides or miticides containing these 3-arylphenyl sulfide derivatives as an active ingredient (3) a method of killing a farm or garden pest insect or mites which uses an effective amount of these 3-arylphenyl sulfide derivatives.

The terms used in this application are defined below.

The halogen atom represents a fluorine atom, a chlorine atom, a bromine atom or an iodine atom.

The alkyl group means a linear or branched $C_{1-6}$ alkyl group such as a methyl group, an ethyl group, a n-propyl group, an isopropyl group, a n-butyl group, an isobutyl group, a sec-butyl group or a tert-butyl group, unless otherwise noted.

The cycloalkyl group means a $C_{3-6}$ cycloalkyl group such as a cyclopropyl group, a cyclopentyl group or a cyclohexyl group.

The cycloalkylalkyl group means a $C_{1-3}$ alkyl group substituted with a $C_{3-6}$ cycloalkyl group such as a cyclopropylmethyl group, a cyclopentylmethyl group or a cyclohexylmethyl group.

The alkenyl group means a linear or branched $C_{2-6}$ alkenyl group such as an ethenyl group or a 2-propenyl group.

The alkynyl group means a linear or branched $C_{2-6}$ alkynyl group such as an ethynyl group or a 2-propynyl group.

The haloalkyl group means a $C_{1-4}$ alkyl group substituted with from 1 to 9 identical or different halogen atoms such as a chloromethyl group, a trifluoromethyl group or a tetrafluoroethyl group, unless otherwise noted.

The alkoxy group means an alkyl-O-group wherein the alkyl moiety is as defined above, such as a methoxy group or an ethoxy group.

The alkoxyalkyl group means an alkyl-O-alkyl-group wherein the alkyl moieties are as defined above, such as a methoxymethyl group or an ethoxymethyl group.

The alkoxyalkoxy group means an alkyl-O-alkyl-O-group wherein the alkyl moieties are as defined above, such as a methoxymethoxy group or an ethoxymethoxy group.

The haloalkoxy group means a haloalkyl-O-group wherein the haloalkyl moiety is as defined above, such as a trifluoromethoxy group or a 2,2,2-trifluoroethoxy group.

The alkylthio group, the alkylsulfinyl group and the alkylsulfonyl group mean, respectively, an alkyl-S-group, an alkyl-SO-group and an alkyl-$SO_2$-group wherein the alkyl moieties are as defined above, such as a methylthio group, an ethylthio group, a methylsulfinyl group, an ethylsulfinyl group, a methylsulfonyl group or an ethylsulfonyl group.

The haloalkylthio group, the haloalkylsulfinyl group and the haloalkylsulfonyl group mean, respectively, a haloalkyl-S-group, a haloalkyl-SO-group and a haloalkyl-$SO_2$-group wherein the haloalkyl moieties are as defined above, such as a trifluoromethylthio group, a dichlorofluoromethylthio group, a trifluoromethylsulfinyl group, a 2,2,2-trifluoroethylsulfinyl group, a trifluoromethylsulfonyl group or a 2,2,2-trifluoroethylsulfonyl group.

The acyl group means a formyl group or an alkyl-CO-group wherein the alkyl group is as defined above, such as an acetyl group or a propionyl group.

The haloalkylcarbonyl group and the alkoxycarbonyl group means, respectively, a haloalkyl-CO-group and an alkoxy-CO-group wherein the haloalkyl and alkoxy moieties are as defined above, such as a trifluoroacetyl group or a methoxycarbonyl group.

Preferred compounds of general formula (I) described above are those wherein Ar is represented by general formula (Ar-1) or general formula (Ar-4), R is a 2,2,2-trifluoroethyl group, a n-propyl group, a 2,2,3,3-tetrafluoropropyl group or a cyclopropylmethyl group, and n is 0 or 1.

Still further preferred compounds are those wherein R is a 2,2,2-trifluoroethyl group, a n-propyl group, a 2,2,3,3-tetrafluoropropyl group or a cyclopropylmethyl group, Ar is a phenyl group having hydrogen atoms as $A_1$ and $A_5$ and a halogen atom, a difluoromethoxy group, a trifluoromethoxy group or a trifluoromethyl group as $A_3$ or $A_2$, $B_0$ is a hydrogen atom, a methyl group or a halogen atom, $B_2$ is a halogen atom, a cyano group, an alkyl group or a haloalkyl group, and n is 0 or 1.

Now, typical specific examples of the compound represented by general formula (I) of the present invention will be given in Tables 1 to 60. The compound numbers used in the tables will be referred to in the subsequent description. Herein, the symbols in the tables denote the following groups.

Me: a methyl group, Et: an ethyl group,
Pr: a n-propyl group, Pr-i: an isopropyl group,
Pr-c: a cyclopropyl group, Bu: a n-butyl group,
Bu-i: an isobutyl group, Bu-s: a sec-butyl group,
Bu-t: a tert-butyl group, Bu-c: a cyclobutyl group,
Pen: a n-pentyl group, Pen-i: an isopentyl group,
Pen-c: a cyclopentyl group, Hex-c: a cyclohexyl group.

TABLE 1

[Structure: biphenyl with substituents A1, A2, A3, A4, A5 on one ring and B0, B1, B2, B3, S(O)nR on the other]

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-1  | H   | H   | H   | H | H | H | H | CN | H | Et        | 0 |         |
| I-2  | H   | H   | H   | H | H | H | H | CN | H | Pr        | 0 | 1.6310  |
| I-3  | H   | H   | H   | H | H | H | H | CN | H | CH$_2$Pr-c | 0 | 1.6411  |
| I-4  | H   | H   | H   | H | H | H | H | Me | H | Et        | 0 |         |
| I-5  | H   | H   | H   | H | H | H | H | Me | H | Pr        | 0 |         |
| I-6  | H   | H   | H   | H | H | H | H | Me | H | CH$_2$Pr-c | 0 |         |
| I-7  | CF$_3$ | H  | H   | H | H | H | H | CN | H | Pr        | 0 | 1.5669  |
| I-8  | CF$_3$ | H  | H   | H | H | H | H | CN | H | CH$_2$Pr-c | 0 | 77-80   |
| I-9  | H   | CF$_3$ | H | H | H | H | H | CN | H | Et        | 0 |         |
| I-10 | H   | CF$_3$ | H | H | H | H | H | CN | H | Pr        | 0 | 53-54   |
| I-11 | H   | CF$_3$ | H | H | H | H | H | CN | H | Pr-i      | 0 |         |
| I-12 | H   | CF$_3$ | H | H | H | H | H | CN | H | CH$_2$Pr-c | 0 | 84-85   |
| I-13 | H   | Me  | H   | H | H | H | H | CN | H | Pr        | 0 | 1.6256  |
| I-14 | H   | Me  | H   | H | H | H | H | CN | H | Bu-i      | 0 |         |
| I-15 | H   | OMe | H   | H | H | H | H | CN | H | Pr        | 0 | 1.6265  |
| I-16 | H   | OMe | H   | H | H | H | H | CN | H | CH$_2$Pr-c | 0 |         |
| I-17 | H   | H   | CF$_3$ | H | H | H | H | CN | H | Et        | 0 | 108-110 |
| I-18 | H   | H   | CF$_3$ | H | H | H | H | CN | H | Pr        | 0 | 81-82   |
| I-19 | H   | H   | CF$_3$ | H | H | H | H | CN | H | Pr        | 1 | 105-107 |
| I-20 | H   | H   | CF$_3$ | H | H | H | H | CN | H | Pr        | 2 | 127-128 |
| I-21 | H   | H   | CF$_3$ | H | H | H | H | CN | H | Bu        | 0 | 74-75   |
| I-22 | H   | H   | CF$_3$ | H | H | H | H | CN | H | Pen-i     | 0 | 59-60   |
| I-23 | H   | H   | Me  | H | H | H | H | CN | H | Pr        | 0 | 64-65   |
| I-24 | H   | H   | OMe | H | H | H | H | CN | H | Pr        | 0 | 1.6409  |
| I-25 | Cl  | H   | H   | H | H | H | H | CN | H | Pr        | 0 |         |
| I-26 | H   | Cl  | H   | H | H | H | H | CN | H | Pr        | 0 | 67-68   |
| I-27 | H   | H   | Cl  | H | H | H | H | CN | H | Pr        | 0 | 79-80   |

RI: refractive index

TABLE 2

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-28 | H | H | CF$_3$ | H | H | H | H | CN | H | Pr-i       | 0 | 71-74   |
| I-29 | H | H | CF$_3$ | H | H | H | H | CN | H | Pr-i       | 1 | 68-71   |
| I-30 | H | H | CF$_3$ | H | H | H | H | CN | H | Pr-i       | 2 | 87-90   |
| I-31 | H | H | CF$_3$ | H | H | H | H | CN | H | Bu-s       | 0 | 99-102  |
| I-32 | H | H | CF$_3$ | H | H | H | H | CN | H | Bu-s       | 0 | 60-61   |
| I-33 | H | H | CF$_3$ | H | H | H | H | CN | H | C$_3$F$_7$-n | 0 | 75-76 |
| I-34 | H | H | Cl     | H | H | H | H | CN | H | C$_3$F$_7$-n | 0 |       |
| I-35 | H | H | Cl     | H | H | H | H | CN | H | CH$_2$Pr-c | 0 | 107-108 |
| I-36 | H | H | Cl     | H | H | H | H | CN | H | CH$_2$Pr-c | 1 |         |
| I-37 | H | H | CF$_3$ | H | H | H | H | CN | H | CH$_2$Pr-c | 0 | 102-105 |
| I-38 | H | H | CF$_3$ | H | H | H | H | CN | H | CH$_2$Pr-c | 1 | 82-83   |
| I-39 | H | H | CF$_3$ | H | H | H | H | CN | H | CH$_2$Pr-c | 2 | 132-133 |
| I-40 | H | H | CF$_3$ | H | H | H | H | CN | H | Bu-i       | 0 | 76-77   |
| I-41 | H | H | CF$_3$ | H | H | H | H | CN | H | CH$_2$Bu-t | 0 | 99-100  |
| I-42 | H | H | CF$_3$ | H | H | H | H | CN | H | CH$_2$CH=CH$_2$ | 0 | 89-90 |
| I-43 | H | H | CF$_3$ | H | H | H | H | CN | H | CH$_2$C≡CH | 0 | 131-132 |
| I-44 | H | H | CF$_3$ | H | H | H | H | CN | H | CH$_2$CHF$_2$ | 0 | 121-122 |
| I-45 | H | Cl | Cl    | H | H | H | H | CN | H | Pr         | 0 | 109-110 |
| I-46 | H | H | SCF$_3$ | H | H | H | H | CN | H | Pr        | 0 | 76-78   |
| I-47 | H | H | Bu-t   | H | H | H | H | CN | H | Pr         | 0 | 1.6074  |
| I-48 | H | H | OCF$_3$ | H | H | H | H | CN | H | Pr        | 0 | 58-59   |
| I-49 | H | H | OCF$_3$ | H | H | H | H | CN | H | CH$_2$Pr-c | 0 | 73-75   |
| I-50 | H | H | CF$_3$ | H | H | F | H | Me | H | CH$_2$Pr-c | 0 | 35-36   |
| I-51 | H | H | CF$_3$ | H | H | F | H | Me | H | CH$_2$Pr-c | 1 | 72-73   |

TABLE 2-continued

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-52 | H | H | $CF_3$ | H | H | H | H | Me | H | Pr | 0 | 55-57 |
| I-53 | H | H | $CF_3$ | H | H | H | H | Me | H | Pr | 1 | 67-68 |
| I-54 | H | H | $CF_3$ | H | H | H | H | OMe | H | Pr | 0 | 68-70 |
| I-55 | Cl | H | $CF_3$ | H | Cl | H | H | Me | H | Pr-i | 0 | 1.5462 |
| I-56 | Cl | H | $CF_3$ | H | Cl | H | H | $NO_2$ | H | Pr-i | 0 | 1.5881 |
| I-57 | Cl | H | $CF_3$ | H | Cl | H | H | $NH_2$ | H | Pr-i | 0 | 1.5782 |
| I-58 | Cl | H | $CF_3$ | H | Cl | H | H | Br | H | Pr-i | 0 | 1.5642 |
| I-59 | Cl | H | $CF_3$ | H | H | H | H | CN | H | Bu-i | 0 | 1.5691 |
| I-60 | Cl | H | $CF_3$ | H | H | H | H | CN | H | $CH_2Pr$-c | 0 | 64-65 |
| I-61 | Cl | H | Cl | H | H | H | H | CN | H | $CH_2Pr$-c | 0 | 95-96 |

TABLE 3

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-62 | Cl | H | Cl | H | H | H | H | CN | H | Et | 0 | 89-92 |
| I-63 | H | H | $CF_3$ | H | H | H | H | H | H | Pr-i | 2 | 1.5469 |
| I-64 | H | H | $CF_3$ | H | H | H | H | H | H | Pr-i | 0 | 1.5560 |
| I-65 | H | H | $CF_3$ | H | H | H | H | H | H | Pr-i | 1 | 1.5599 |
| I-66 | H | H | $CF_3$ | H | H | H | H | H | H | Bu-t | 2 | 1.5418 |
| I-67 | H | H | $CF_3$ | H | H | H | H | H | H | Pen-c | 0 | 1.5732 |
| I-68 | H | H | $CF_3$ | H | H | H | H | H | H | $CH_2Pr$-c | 0 | Unmeasurable |
| I-69 | H | H | $CF_3$ | H | H | H | H | H | H | $CH_2Pr$-c | 2 | 75-77 |
| I-70 | Cl | H | Cl | H | H | H | H | H | H | Pr-i | 2 | 1.5807 |
| I-71 | Cl | H | Cl | H | H | H | H | H | H | Pr-i | 0 | 1.6143 |
| I-72 | Cl | H | Cl | H | H | H | H | H | H | Pr-i | 1 | 1.6169 |
| I-73 | Cl | H | $CF_3$ | H | Cl | H | H | H | H | Pr-i | 0 | 1.5675 |
| I-74 | Cl | H | $CF_3$ | H | Cl | H | H | H | H | Pr-i | 1 | 1.5658 |
| I-75 | Cl | H | $CF_3$ | H | Cl | H | H | H | H | Pr-i | 2 | 1.5412 |
| I-76 | H | Cl | H | Cl | H | H | H | CN | H | $CH_2Pr$-c | 0 | 179-180 |
| I-77 | H | Cl | H | Cl | H | H | H | CN | H | Pr | 0 | 65-66 |
| I-78 | H | H | $CF_3$ | H | H | H | H | Cl | H | Pr-i | 0 | 1.5704 |
| I-79 | H | H | $CF_3$ | H | H | H | H | Cl | H | Pr | 0 | 48-49 |
| I-80 | H | H | $CF_3$ | H | H | H | H | Cl | H | Pr | 1 | |
| I-81 | H | H | $CF_3$ | H | H | H | H | Cl | H | $CH_2Pr$-c | 0 | 64-65 |
| I-82 | H | H | $CF_3$ | H | H | H | H | Cl | H | $CH_2Pr$-c | 1 | 1.5692 |
| I-83 | H | H | CN | H | H | H | H | CN | H | Pr | 0 | 146-148 |
| I-84 | H | H | CN | H | H | H | H | CN | H | Pr | 1 | |
| I-85 | H | H | $OCHF_2$ | H | H | H | H | CN | H | $CH_2Pr$-c | 0 | 56-58 |
| I-86 | H | H | $CHF_2$ | H | H | H | H | CN | H | $CH_2Pr$-c | 1 | |
| I-87 | H | H | $CHF_2$ | H | H | H | H | CN | H | Pr | 0 | 64-65 |
| I-88 | H | H | $CHF_2$ | H | H | H | H | CN | H | Pr | 1 | |
| I-89 | H | H | $CF_3$ | H | H | H | H | CN | H | $CF_2CF_2Cl$ | 0 | 104-105 |
| I-90 | H | H | $CF_3$ | H | H | H | H | CN | H | $CF_2CF_2Cl$ | 1 | |
| I-91 | H | H | $CF_3$ | H | H | H | H | CHO | H | Pr | 0 | 69-70 |
| I-92 | H | H | $CF_3$ | H | H | H | H | $CO_2H$ | H | Pr | 0 | 241-242 |
| I-93 | H | H | $CF_3$ | H | H | H | H | $NH_2$ | H | $CH_2Pr$-c | 0 | 44-45 |
| I-94 | H | H | $CF_3$ | H | H | H | H | $NO_2$ | H | Pr | 1 | |
| I-95 | H | H | $CF_3$ | H | H | H | H | $SO_2Me$ | H | Pr | 0 | |

TABLE 4

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-96 | H | H | $CF_3$ | H | H | H | H | $CHF_2$ | H | Pr | 0 | Unmeasurable |
| I-97 | H | H | $CF_3$ | H | H | H | H | $CHF_2$ | H | Pr | 1 | |
| I-98 | H | H | $CF_3$ | H | H | H | H | $CF_3$ | H | Pr | 0 | 1.5267 |
| I-99 | H | H | $CF_3$ | H | H | H | H | $CF_3$ | H | Pr | 1 | 94-95 |
| I-100 | H | H | $CF_3$ | H | H | H | H | $CF_3$ | H | $CH_2Pr$-c | 1 | 70-71 |
| I-101 | H | Cl | Me | H | H | H | H | CN | H | Pr | 0 | 52-53 |

TABLE 4-continued

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-102 | H | Cl | Me | H | H | H | H | CN | H | Pr | 1 | 97-99 |
| I-103 | H | Me | Cl | H | H | H | H | CN | H | Pr | 0 | 51-52 |
| I-104 | H | Me | Cl | H | H | H | H | CN | H | Pr | 1 | 123-124 |
| I-105 | H | F | Me | H | H | H | H | CN | H | Pr | 0 | 63-64 |
| I-106 | H | H | $CF_3$ | H | H | H | H | Me | H | Pr | 2 | 73-75 |
| I-107 | H | Me | F | H | H | H | H | CN | H | Pr | 0 | 34-35 |
| I-108 | H | Cl | Me | H | H | H | H | CN | H | $CH_2Pr$-c | 0 | 79-80 |
| I-109 | H | Me | Cl | H | H | H | H | CN | H | $CH_2Pr$-c | 0 | 72-73 |
| I-110 | H | F | Me | H | H | H | H | CN | H | $CH_2Pr$-c | 0 | 67-69 |
| I-111 | H | Me | F | H | H | H | H | CN | H | $CH_2Pr$-c | 0 | 59-60 |
| I-112 | H | F | Me | H | H | H | H | CN | H | Pr | 1 | 102-104 |
| I-113 | H | $CF_3$ | H | $CF_3$ | H | H | H | CN | H | Pr | 0 | 60-61 |
| I-114 | H | $CF_3$ | H | $CF_3$ | H | H | H | CN | H | $CH_2Pr$-c | 0 | 91-92 |
| I-115 | Me | H | H | H | H | H | H | CN | H | Pr | 0 | 1.6159 |
| I-116 | H | H | $CF_3$ | H | H | H | H | $CO_2Et$ | H | Pr | 0 | 63-64 |
| I-117 | H | OMe | OMe | H | H | H | H | CN | H | Pr | 0 | 1.6395 |
| I-118 | H | H | F | H | H | H | H | CN | H | Pr | 0 | 62-63 |
| I-119 | H | H | $CF_3$ | H | H | H | H | Me | H | $CH_2Pr$-c | 0 | 50-51 |
| I-120 | H | H | $CF_3$ | H | H | H | H | Me | H | $CH_2Pr$-c | 1 | 58-60 |
| I-121 | H | H | $CF_3$ | H | H | H | H | Me | H | $CH_2Pr$-c | 2 | 1.5419 |
| I-122 | H | Me | F | H | H | H | H | CN | H | Pr | 1 | 97-98 |
| I-123 | H | H | $CF_3$ | H | H | H | H | CN | H | $CH_2CF_3$ | 0 | 150-151 |
| I-124 | H | H | $CF_3$ | H | H | H | H | CN | H | $CH_2CF_3$ | 1 | 161-162 |
| I-125 | H | H | $CF_3$ | H | H | H | H | CN | H | $CF_2CHF_2$ | 0 | 94-96 |
| I-126 | H | H | $CF_3$ | H | H | H | H | CN | H | CF2Et | 1 | |
| I-127 | H | H | $CF_3$ | H | H | H | H | CN | H | $CH_2CH_2CF_3$ | 0 | 92-94 |
| I-128 | H | H | $CF_3$ | H | H | H | H | CN | H | $CH_2CH_2CF_3$ | 1 | 151-153 |
| I-129 | H | H | $CF_3$ | H | H | H | H | CN | H | $CH_2CF_2CHF_2$ | 0 | 45-47 |

TABLE 5

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-130 | H | H | $CF_3$ | H | H | H | H | CN | H | $CH_2CF_2CHF_2$ | 1 | 73-75 |
| I-131 | H | H | $CF_3$ | H | H | H | H | Me | H | $CH_2CF_3$ | 0 | 1.5359 |
| I-132 | H | H | $CF_3$ | H | H | H | H | Me | H | $CH_2CF_3$ | 1 | 113-114 |
| I-133 | H | H | $CF_3$ | H | H | H | H | $CHF_2$ | H | $CH_2CF_3$ | 0 | 1.5094 |
| I-134 | H | H | $CF_3$ | H | H | H | H | $CHF_2$ | H | $CH_2CF_3$ | 1 | 122-124 |
| I-135 | H | H | $CF_3$ | H | H | H | H | CN | H | $CH_2CF_2CF_3$ | 0 | |
| I-136 | H | H | $CF_3$ | H | H | H | H | CN | H | $CH_2CF_2CF_3$ | 1 | |
| I-137 | H | H | $CF_3$ | H | H | H | H | CN | H | $CH_2CH_2Cl$ | 0 | 84-85 |
| I-138 | H | H | $CF_3$ | H | H | H | H | $CF_3$ | H | $CH_2Pr$-c | 0 | |
| I-139 | H | H | $CF_3$ | H | H | H | Cl | CN | H | Pr | 0 | 75-76 |
| I-140 | H | H | $CF_3$ | H | H | H | Cl | CN | H | Pr | 1 | |
| I-141 | H | H | $CF_3$ | H | H | H | Cl | CN | H | $CH_2Pr$-c | 0 | |
| I-142 | H | H | $CF_3$ | H | H | H | Cl | CN | H | $CH_2Pr$-c | 1 | |
| I-143 | H | H | $CF_3$ | H | H | H | Me | CN | H | Pr | 0 | |
| I-144 | H | H | $CF_3$ | H | H | H | Me | CN | H | Pr | 1 | |
| I-145 | H | H | $CF_3$ | H | H | H | Me | CN | H | $CH_2Pr$-c | 0 | |
| I-146 | H | H | $CF_3$ | H | H | H | Me | CN | H | $CH_2Pr$-c | 1 | |
| I-147 | H | H | $CF_3$ | H | H | H | OMe | CN | H | Pr | 0 | |
| I-148 | H | H | $CF_3$ | H | H | H | OMe | CN | H | Pr | 1 | |
| I-149 | H | H | $CF_3$ | H | H | H | OMe | CN | H | $CH_2Pr$-c | 0 | |
| I-150 | H | H | $CF_3$ | H | H | H | OMe | CN | H | $CH_2Pr$-c | 1 | |
| I-151 | H | H | $CF_3$ | H | H | H | H | Br | H | Pr | 0 | 55-56 |
| I-152 | H | H | $CF_3$ | H | H | H | H | Br | H | Pr | 1 | 1.5712 |
| I-153 | H | H | $CF_3$ | H | H | H | H | Br | H | Pr | 2 | 73-75 |
| I-154 | H | H | COMe | H | H | H | H | CN | H | Pr | 0 | 97-98 |
| I-155 | H | H | $CF_3$ | H | H | H | H | CN | Me | Pr | 0 | |
| I-156 | H | H | $CF_3$ | H | H | H | H | CN | Me | Pr | 1 | |
| I-157 | H | H | $CF_3$ | H | H | H | H | CN | Me | $CH_2Pr$-c | 0 | |
| I-158 | H | H | $CF_3$ | H | H | H | H | CN | Me | $CH_2Pr$-c | 1 | |
| I-159 | H | H | $CF_3$ | H | H | H | H | CN | OMe | Pr | 0 | |
| I-160 | H | H | $CF_3$ | H | H | H | H | CN | OMe | Pr | 1 | |
| I-161 | H | H | $CF_3$ | H | H | H | H | CN | OMe | $CH_2Pr$-c | 0 | |

TABLE 5-continued

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-162 | H | H | $CF_3$ | H | H | H | H | CN | OMe | $CH_2Pr$-c | 1 | |
| I-163 | H | H | $CF_3$ | H | H | H | H | $NO_2$ | H | Pr | 0 | 99-100 |

TABLE 6

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-164 | H | H | $CF_3$ | H | H | H | H | CN | H | 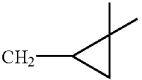 | 0 | |
| I-165 | H | H | $CF_3$ | H | H | H | H | CN | H | 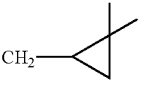 | 1 | |
| I-166 | H | OMe | OMe | OMe | H | H | H | CN | H | Pr | 0 | 1.6221 |
| I-167 | H | OMe | OMe | OMe | H | H | H | CN | H | Pr | 1 | 1.6145 |
| I-168 | H | OMe | OMe | H | H | H | H | CN | H | $CH_2Pr$-c | 0 | 73-74 |
| I-169 | H | OMe | OMe | H | H | H | H | CN | H | Pr | 1 | 130-131 |
| I-170 | H | H | $CF_3$ | H | H | H | H | CN | H | $CH_2CH_2Cl$ | 1 | 138-139 |
| I-171 | H | H | $CF_3$ | H | H | H | H | CN | Cl | Pr | 0 | 102-104 |
| I-172 | H | H | $CF_3$ | H | H | H | H | CN | Cl | Pr | 1 | 153-154 |
| I-173 | H | H | $CF_3$ | H | H | H | H | CN | Cl | $CH_2Pr$-c | 0 | 104-106 |
| I-174 | H | H | $CF_3$ | H | H | H | H | CN | Cl | $CH_2Pr$-c | 1 | 188-189 |
| I-175 | F | H | H | H | H | H | H | CN | H | Pr | 0 | 1.6120 |
| I-176 | H | $CF_3$ | H | $CF_3$ | H | H | H | CN | H | Pr | 1 | 148-151 |
| I-177 | H | H | $CF_3$ | H | H | H | H | CN | H | $C_2F_5$ | 0 | 93-94 |
| I-178 | H | H | $CF_3$ | H | H | H | H | CN | H | $C_2F_5$ | 1 | 105-107 |
| I-179 | H | H | $NO_2$ | H | H | H | H | CN | H | Pr | 0 | 149-152 |
| I-180 | H | H | $NO_2$ | H | H | H | H | CN | H | Pr | 1 | 121-122 |
| I-181 | H | F | H | H | H | H | H | CN | H | Pr | 0 | 1.6195 |
| I-182 | H | F | H | H | H | H | H | CN | H | Pr | 1 | |
| I-183 | H | H | $CF_3$ | H | H | H | H | $CHF_2$ | H | $CH_2Pr$-c | 0 | 41-42 |
| I-184 | H | H | $CF_3$ | H | H | H | H | $CHF_2$ | H | $CH_2Pr$-c | 1 | 1.5323 |
| I-185 | H | H | $CF_3$ | H | H | H | H | F | H | Pr | 0 | 1.5495 |
| I-186 | H | H | $CF_3$ | H | H | H | H | F | H | Pr | 1 | 1.5428 |
| I-187 | H | H | $CF_3$ | H | H | H | H | Et | H | $CH_2Pr$-c | 0 | 39-40 |
| I-188 | H | H | $CF_3$ | H | H | H | H | Et | H | $CH_2Pr$-c | 1 | 1.5621 |
| I-189 | H | H | $CF_3$ | H | H | H | H | OMe | H | Pr | 1 | 68-69 |
| I-190 | H | H | $CF_3$ | H | H | H | H | OMe | H | $CH_2CF_3$ | 0 | 54-55 |
| I-191 | H | H | $CF_3$ | H | H | H | H | OMe | H | $CH_2CF_3$ | 1 | 115-116 |
| I-192 | H | H | $CF_3$ | H | H | H | H | OMe | H | $CH_2Pr$-c | 0 | 75-77 |
| I-193 | H | H | $CF_3$ | H | H | H | H | OMe | H | $CH_2Pr$-c | 1 | 67-68 |
| I-194 | H | H | $CF_3$ | H | H | H | H | OEt | H | Pr | 0 | 58-59 |
| I-195 | H | H | $CF_3$ | H | H | H | H | OEt | H | Pr | 1 | 71-72 |

TABLE 7

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-196 | H | H | $CF_3$ | H | H | H | H | OEt | H | $CH_2CF_3$ | 0 | 71-72 |
| I-197 | H | H | $CF_3$ | H | H | H | H | OEt | H | $CH_2CF_3$ | 1 | 148-150 |
| I-198 | H | H | $CF_3$ | H | H | H | H | OEt | H | $CH_2Pr$-c | 0 | 90-92 |
| I-199 | H | H | $CF_3$ | H | H | H | H | OEt | H | $CH_2Pr$-c | 1 | 70-71 |
| I-200 | H | H | $CF_3$ | H | H | H | H | OPr-i | H | Pr | 0 | 48-50 |
| I-201 | H | H | $CF_3$ | H | H | H | H | OPr-i | H | Pr | 1 | 1.5579 |
| I-202 | H | H | $CF_3$ | H | H | H | H | OPr-i | H | $CH_2CF_3$ | 0 | 52-53 |

TABLE 7-continued

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-203 | H | H | $CF_3$ | H | H | H | H | OPr-i | H | $CH_2CF_3$ | 1 | 145-146 |
| I-204 | H | H | $CF_3$ | H | H | H | H | OPr-i | H | $CH_2Pr$-c | 0 | 87-88 |
| I-205 | H | H | $CF_3$ | H | H | H | H | OPr-i | H | $CH_2Pr$-c | 1 | 1.5605 |
| I-206 | H | H | $CF_3$ | H | H | H | H | $OCHF_2$ | H | Pr | 0 | 1.5440 |
| I-207 | H | H | $CF_3$ | H | H | H | H | $OCHF_2$ | H | Pr | 1 | 77-79 |
| I-208 | H | H | $CF_3$ | H | H | H | H | $OCHF_2$ | H | $CH_2CF_3$ | 0 | 1.5121 |
| I-209 | H | H | $CF_3$ | H | H | H | H | $OCHF_2$ | H | $CH_2CF_3$ | 1 | 78-80 |
| I-210 | H | H | $CF_3$ | H | H | H | H | $OCHF_2$ | H | $CH_2Pr$-c | 0 | 1.5540 |
| I-211 | H | H | $CF_3$ | H | H | H | H | $OCHF_2$ | H | $CH_2Pr$-c | 1 | 74-75 |
| I-212 | H | H | $CF_3$ | H | H | H | H | $OCH_2OEt$ | H | Pr | 0 | 1.5491 |
| I-213 | H | H | $CF_3$ | H | H | H | H | $OCH_2OEt$ | H | $CH_2CF_3$ | 0 | 1.5213 |
| I-214 | H | H | $CF_3$ | H | H | H | H | $OCH_2OEt$ | H | $CH_2Pr$-c | 0 | 50-51 |
| I-215 | H | H | $CF_3$ | H | H | H | H | Cl | H | $CH_2CF_3$ | 0 | 54-56 |
| I-216 | H | H | $CF_3$ | H | H | H | H | Cl | H | $CH_2CF_3$ | 1 | 117-119 |
| I-217 | H | H | $CF_3$ | H | H | H | H | NHCOMe | H | $CH_2Pr$-c | 0 | 123-124 |
| I-218 | H | H | $CF_3$ | H | H | H | H | CN | H | $C_2H_4CF=CF_2$ | 0 | 80-82 |
| I-219 | H | H | $CF_3$ | H | H | H | H | CN | H | $CH_2Bu$-c | 0 | 75-76 |
| I-220 | H | H | $CF_3$ | H | H | H | H | CN | H | $CH_2Bu$-c | 1 | 105-106 |
| I-221 | H | H | $CF_3$ | H | H | F | H | $NO_2$ | H | Pr | 0 | 57-59 |
| I-222 | H | H | $CF_3$ | H | H | F | H | $NO_2$ | H | Pr | 1 | 123-125 |
| I-223 | H | H | $CF_3$ | H | H | F | H | $NO_2$ | H | $CH_2Pr$-c | 0 | 118-119 |
| I-224 | H | H | $CF_3$ | H | H | F | H | $NO_2$ | H | $CH_2Pr$-c | 1 | 153-154 |
| I-225 | H | H | $CF_3$ | H | H | SPr | H | CN | H | Pr | 0 | 66-67 |
| I-226 | H | H | $CF_3$ | H | H | F | H | CN | H | Pr | 0 | |
| I-227 | H | H | $CF_3$ | H | H | F | H | CN | H | $CH_2Pr$-c | 0 | 83-84 |
| I-228 | H | H | $CF_3$ | H | H | F | H | CN | H | $CH_2Pr$-c | 1 | 123-125 |
| I-229 | H | H | $CF_3$ | H | H | Cl | H | CN | H | $CH_2Pr$-c | 0 | 89-90 |

TABLE 8

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-230 | H | H | $CF_3$ | H | H | Cl | H | CN | H | $CH_2Pr$-c | 1 | 146-147 |
| I-231 | H | H | $CF_3$ | H | H | F | H | Me | H | $C_2F_5$ | 0 | 1.4826 |
| I-232 | H | H | $CF_3$ | H | H | F | H | Me | H | $C_2F_5$ | 1 | 55-56 |
| I-233 | H | H | $CF_3$ | H | H | F | H | Me | H | Pr | 0 | 31-33 |
| I-234 | H | H | $CF_3$ | H | H | F | H | Me | H | Pr | 1 | 104-106 |
| I-235 | H | H | $CF_3$ | H | H | F | H | Me | H | Pr-i | 0 | Unmeasurable |
| I-236 | H | H | $CF_3$ | H | H | F | H | Me | H | Pr-i | 1 | 94.95 |
| I-237 | H | H | $CF_3$ | H | H | F | H | Me | H | Pr-i | 2 | 99-100 |
| I-238 | H | H | $CF_3$ | H | H | F | H | Me | H | $CH_2CF_3$ | 0 | 1.5179 |
| I-239 | H | H | $CF_3$ | H | H | F | H | Me | H | $CH_2CF_3$ | 1 | 116-117 |
| I-240 | H | H | $CF_3$ | H | H | H | F | Me | H | $CH_2Pr$-c | 0 | 1.5491 |
| I-241 | H | H | $CF_3$ | H | H | H | F | Me | H | $CH_2Pr$-c | 1 | 1.5435 |
| I-242 | H | H | $CF_3$ | H | H | H | F | Me | H | $CH_2CF_3$ | 0 | 1.5084 |
| I-243 | H | H | $CF_3$ | H | H | H | F | Me | H | $CH_2CF_3$ | 1 | 83-84 |
| I-244 | H | H | $CF_3$ | H | H | F | H | $NH_2$ | H | $CH_2Pr$-c | 0 | Unmeasurable |
| I-245 | H | H | $CF_3$ | H | H | F | H | Br | H | $CH_2Pr$-c | 0 | Unmeasurable |
| I-246 | H | H | $CF_3$ | H | H | F | H | Br | H | $CH_2Pr$-c | 1 | |
| I-247 | H | H | $CF_3$ | H | H | F | H | Me | H | $CH_2Pr$-c | 2 | 93-94 |
| I-248 | H | H | Cl | H | H | F | H | Me | H | $CH_2Pr$-c | 0 | 57-60 |
| I-249 | H | H | Cl | H | H | F | H | Me | H | $CH_2Pr$-c | 1 | 1.6082 |
| I-250 | H | $CF_3$ | H | H | H | F | H | Me | H | $CH_2Pr$-c | 0 | Unmeasurable |
| I-251 | H | $CF_3$ | H | H | H | F | H | Me | H | $CH_2Pr$-c | 1 | 78-79 |
| I-252 | H | H | $CF_3$ | H | H | F | H | Cl | H | $CH_2CF_3$ | 0 | 1.5292 |
| I-253 | H | H | $CF_3$ | H | H | F | H | Cl | H | $CH_2CF_3$ | 1 | 125-127 |
| I-254 | H | H | $CF_3$ | H | H | F | H | Cl | H | $CH_2Pr$-c | 0 | 52-53 |
| I-255 | H | H | $CF_3$ | H | H | F | H | Cl | H | $CH_2Pr$-c | 1 | 67-68 |
| I-256 | H | H | $CF_3$ | H | H | F | H | Me | H | $CH_2CF_2CHF_2$ | 0 | 1.5139 |
| I-257 | H | H | $CF_3$ | H | H | F | H | Me | H | $CH_2CF_2CHF_2$ | 1 | 109-110 |
| I-258 | H | H | $CF_3$ | H | H | Cl | H | Me | H | $CH_2Pr$-c | 0 | 64-65 |
| I-259 | H | H | $CF_3$ | H | H | Cl | H | Me | H | $CH_2Pr$-c | 1 | 84-85 |
| I-260 | H | H | $CF_3$ | H | H | Cl | H | Me | H | $CH_2CF_3$ | 0 | 1.5295 |
| I-261 | H | H | $CF_3$ | H | H | Cl | H | Me | H | $CH_2CF_3$ | 1 | 154-155 |
| I-262 | H | H | $CF_3$ | H | H | H | H | Me | H | $CH_2CF_2CHF_2$ | 0 | 1.5209 |
| I-263 | H | H | $CF_3$ | H | H | H | H | Me | H | $CH_2CF_2CHF_2$ | 1 | 109-111 |

TABLE 9

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-264 | H | H | $CF_3$ | H | H | Me | H | Me | H | $CH_2CF_3$ | 0 | Unmeasurable |
| I-265 | H | H | $CF_3$ | H | H | Me | H | Me | H | $CH_2CF_3$ | 1 | 134-135 |
| I-266 | H | H | $CF_3$ | H | H | F | H | H | H | $CH_2Pr$-c | 0 | Unmeasurable |
| I-267 | H | H | $CF_3$ | H | H | F | H | H | H | $CH_2Pr$-c | 1 | 65-66 |
| I-268 | H | H | $CF_3$ | H | H | Cl | H | H | H | Pr-i | 2 | 105-108 |
| I-269 | H | H | $CF_3$ | H | H | $NH_2$ | H | H | H | Pr-i | 0 | 1.5671 |
| I-270 | H | H | $CF_3$ | H | H | $NH_2$ | H | H | H | Pr-i | 1 | 156-159 |
| I-271 | H | H | $CF_3$ | H | H | $NH_2$ | H | H | H | Pr-i | 2 | 135-138 |
| I-272 | H | H | $CF_3$ | H | H | Cl | H | H | H | Pr-i | 0 | 1.5394 |
| I-273 | Cl | H | Cl | H | H | Cl | H | H | H | Pr-i | 0 | 1.6129 |
| I-274 | Cl | H | Cl | H | H | $NH_2$ | H | H | H | Pr-i | 0 | 1.6267 |
| I-275 | Cl | H | $CF_3$ | H | Cl | $NO_2$ | H | H | H | Pr-i | 0 | 1.5949 |
| I-276 | H | H | $CF_3$ | H | H | Cl | H | Cl | H | $CH_2Pr$-c | 0 | 67-68 |
| I-277 | H | H | $CF_3$ | H | H | Cl | H | Cl | H | $CH_2Pr$-c | 1 | 140-142 |
| I-278 | H | H | $CF_3$ | H | H | Cl | H | CN | H | $CH_2CF_3$ | 0 | 59-60 |
| I-279 | H | H | $CF_3$ | H | H | Cl | H | CN | H | $CH_2CF_3$ | 1 | 133-134 |
| I-280 | H | H | $CF_3$ | H | H | F | H | $CHF_2$ | H | $CH_2CF_2CHF_2$ | 0 | |
| I-281 | H | H | $CF_3$ | H | H | F | H | $CHF_2$ | H | $CH_2CF_2CHF_2$ | 1 | |
| I-282 | H | H | $CF_3$ | H | H | F | H | $CHF_2$ | H | $CH_2CF_3$ | 0 | 1.4980 |
| I-283 | H | H | $CF_3$ | H | H | F | H | $CHF_2$ | H | $CH_2CF_3$ | 1 | 121-122 |
| I-284 | H | H | $CF_3$ | H | H | F | H | $CHF_2$ | H | $CH_2Pr$-c | 0 | |
| I-285 | H | H | $CF_3$ | H | H | F | H | $CHF_2$ | H | $CH_2Pr$-c | 1 | |
| I-286 | H | H | $CF_3$ | H | H | H | H | $NHCO_2Bu$-t | H | Pr | 0 | 49-51 |
| I-287 | H | H | $CF_3$ | H | H | F | H | CN | H | $CH_2CF_3$ | 0 | 72-73 |
| I-288 | H | H | $CF_3$ | H | H | F | H | CN | H | $CH_2CF_3$ | 1 | 139-140 |
| I-289 | H | H | $CF_3$ | H | H | H | H | Me | H | Pr-i | 0 | 1.5521 |
| I-290 | H | H | $CF_3$ | H | H | H | H | Me | H | Pr-i | 1 | 80-81 |
| I-291 | H | H | $CF_3$ | H | H | Me | H | Me | H | $CH_2Pr$-c | 0 | 1.5604 |
| I-292 | H | H | $CF_3$ | H | H | Me | H | Me | H | $CH_2Pr$-c | 1 | 1.5479 |
| I-293 | H | H | $CF_3$ | H | H | Cl | H | Cl | H | $CH_2CF_3$ | 0 | 1.5422 |
| I-294 | H | H | $CF_3$ | H | H | Cl | H | Cl | H | $CH_2CF_3$ | 1 | 153-154 |
| I-295 | H | H | $CF_3$ | H | H | F | H | Me | H | $CH_2CF_2CF_3$ | 0 | 1.4940 |
| I-296 | H | H | $CF_3$ | H | H | F | H | Me | H | $CH_2CF_2CF_3$ | 1 | 105-107 |
| I-297 | H | H | $CF_3$ | H | H | Cl | H | Me | H | $CH_2CF_2CHF_2$ | 0 | 1.5291 |

TABLE 10

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-298 | H | H | $CF_3$ | H | H | Cl | H | Me | H | $CH_2CF_2CHF_2$ | 1 | 132-134 |
| I-299 | H | H | $CF_3$ | H | H | F | H | $CHF_2$ | H | Pr | 0 | 1.5428 |
| I-300 | H | H | $CF_3$ | H | H | F | H | $CHF_2$ | H | Pr | 1 | 71-72 |
| I-301 | H | H | $CF_3$ | H | H | Cl | H | Me | H | $CH_2CF_2CF_3$ | 0 | 1.4991 |
| I-302 | H | H | $CF_3$ | H | H | Cl | H | Me | H | $CH_2CF_2CF_3$ | 1 | 97-99 |
| I-303 | H | H | H | H | H | F | H | Me | H | $CH_2Pr$-c | 0 | 1.6034 |
| I-304 | H | H | H | H | H | F | H | Me | H | $CH_2Pr$-c | 1 | 1.6027 |
| I-305 | H | H | $CF_3$ | H | H | Me | H | Me | H | $CH_2CF_2CF_3$ | 0 | 1.4998 |
| I-306 | H | H | $CF_3$ | H | H | Me | H | Me | H | $CH_2CF_2CF_3$ | 1 | 104-106 |
| I-307 | H | H | $CF_3$ | H | H | Me | H | Me | H | $CH_2CF_2CHF_2$ | 0 | 1.5159 |
| I-308 | H | H | $CF_3$ | H | H | Me | H | Me | H | $CH_2CF_2CHF_2$ | 1 | 140-142 |
| I-309 | H | H | $CF_3$ | H | H | F | H | Me | H | Et | 0 | 32-33 |
| I-310 | H | H | $CF_3$ | H | H | F | H | Me | H | Et | 1 | 120-121 |
| I-311 | H | H | $CF_3$ | H | H | F | H | Me | H | Bu | 0 | 1.5431 |
| I-312 | H | H | $CF_3$ | H | H | F | H | Me | H | Bu | 1 | 1.5422 |
| I-313 | H | H | $OCF_3$ | H | H | F | H | Me | H | $CH_2Pr$-c | 0 | 1.5465 |
| I-314 | H | H | $OCF_3$ | H | H | F | H | Me | H | $CH_2Pr$-c | 1 | 1.5461 |
| I-315 | H | H | $CF_3$ | H | H | F | H | $NO_2$ | H | $CH_2CF_3$ | 0 | 77-78 |
| I-316 | H | H | $CF_3$ | H | H | F | H | $NO_2$ | H | $CH_2CF_3$ | 1 | |
| I-317 | H | H | $CF_3$ | H | H | F | H | Cl | H | Pr | 0 | 47-48 |
| I-318 | H | H | $CF_3$ | H | H | F | H | Cl | H | Pr | 1 | 78-79 |
| I-319 | H | H | $CF_3$ | H | H | F | H | H | H | $CH_2CF_3$ | 0 | 1.5101 |
| I-320 | H | H | $CF_3$ | H | H | F | H | H | H | $CH_2CF_3$ | 1 | 100-101 |
| I-321 | H | H | $CF_3$ | H | H | F | H | H | H | $CH_2CF_3$ | 2 | 88-90 |
| I-322 | H | H | $CF_3$ | H | H | F | H | $NH_2$ | H | $CH_2CF_3$ | 0 | 1.5331 |
| I-323 | H | H | $CF_3$ | H | H | F | H | $NH_2$ | H | $CH_2CF_3$ | 1 | |
| I-324 | H | H | $CF_3$ | H | H | Me | H | Cl | H | $CH_2CF_3$ | 0 | 1.5268 |

TABLE 10-continued

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-325 | H | H | $CF_3$ | H | H | Me | H | Cl | H | $CH_2CF_3$ | 1 | 150-152 |
| I-326 | H | H | $CF_3$ | H | H | H | H | Me | H | $CH_2CF_3$ | 2 | 107-108 |
| I-327 | H | H | $CF_3$ | H | H | F | H | Me | H | $CH_2CF_3$ | 2 | 110-111 |
| I-328 | H | H | $CF_3$ | H | H | F | H | H | H | $CH_2CF_3$ | 0 | 1.5155 |
| I-329 | H | H | $CF_3$ | H | H | F | H | H | H | $CH_2CF_3$ | 1 | 65-66 |
| I-330 | H | H | $CF_3$ | H | H | OMe | H | Me | H | $CH_2CF_3$ | 0 | 1.5321 |
| I-331 | H | H | $CF_3$ | H | H | OMe | H | Me | H | $CH_2CF_3$ | 1 | 170-172 |

TABLE 11

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-332 | H | H | $CF_3$ | H | H | H | H | SMe | H | $CH_2CF_3$ | 0 | 67-69 |
| I-333 | H | H | $CF_3$ | H | H | H | H | SMe | H | $CH_2CF_3$ | 1 | |
| I-334 | H | H | $CF_3$ | H | H | H | H | SMe | H | Pr | 0 | |
| I-335 | H | H | $CF_3$ | H | H | H | H | SMe | H | Pr | 1 | 1.5899 |
| I-336 | H | H | $CF_3$ | H | H | F | H | Br | H | $CH_2CF_3$ | 0 | 1.5396 |
| I-337 | H | H | $CF_3$ | H | H | F | H | Br | H | $CH_2CF_3$ | 1 | 126-127 |
| I-338 | H | H | $CF_3$ | H | H | F | H | Br | H | $CH_2Pr\text{-}c$ | | |
| I-339 | H | H | $CF_3$ | H | H | F | H | Br | H | $CH_2Pr\text{-}c$ | 1 | 75-78 |
| I-340 | H | H | $CF_3$ | H | H | H | H | Br | H | $CH_2CF_3$ | 0 | 1.5561 |
| I-341 | H | H | $CF_3$ | H | H | H | H | Br | H | $CH_2CF_3$ | 1 | 133-134 |
| I-342 | H | H | $CF_3$ | H | H | F | H | Me | H | Bu-s | 0 | 1.5384 |
| I-343 | H | H | $CF_3$ | H | H | F | H | Me | H | Bu-s | 1 | 86-87 |
| I-344 | H | H | $CF_3$ | H | H | F | H | Me | H | Bu-i | 0 | 1.5402 |
| I-345 | H | H | $CF_3$ | H | H | F | H | Me | H | Bu-i | 1 | 112-113 |
| I-346 | H | H | $CF_3$ | H | H | F | H | Me | H | $C_3F_7\text{-}n$ | 0 | 1.4730 |
| I-347 | H | H | $CF_3$ | H | H | F | H | Me | H | $C_3F_7\text{-}n$ | 1 | 1.4838 |
| I-348 | H | H | $CF_3$ | H | H | Me | H | Cl | H | $CH_2Pr\text{-}c$ | 0 | 1.5734 |
| I-349 | H | H | $CF_3$ | H | H | Me | H | Cl | H | $CH_2Pr\text{-}c$ | 1 | 122-123 |
| I-350 | H | Cl | $CF_3$ | H | H | F | H | Me | H | $CH_2Pr\text{-}c$ | 0 | 1.5708 |
| I-351 | H | Cl | $CF_3$ | H | H | F | H | Me | H | $CH_2Pr\text{-}c$ | 1 | 68-70 |
| I-352 | H | Cl | $CF_3$ | H | H | F | H | Me | H | $CH_2CF_3$ | 0 | 1.5361 |
| I-353 | H | Cl | $CF_3$ | H | H | F | H | Me | H | $CH_2CF_3$ | 1 | 98-99 |
| I-354 | H | H | Cl | H | H | F | H | Me | H | $CH_2CF_3$ | 0 | 1.5661 |
| I-355 | H | H | Cl | H | H | F | H | Me | H | $CH_2CF_3$ | 1 | 112-113 |
| I-356 | H | H | $OCF_3$ | H | H | F | H | Me | H | $CH_2CF_3$ | 0 | 1.5061 |
| I-357 | H | H | $OCF_3$ | H | H | F | H | Me | H | $CH_2CF_3$ | 1 | 94-95 |
| I-358 | H | $CF_3$ | H | H | H | F | H | Me | H | $CH_2CF_3$ | 0 | 1.5130 |
| I-359 | H | $CF_3$ | H | H | H | F | H | Me | H | $CH_2CF_3$ | 1 | 120-121 |
| I-360 | H | $CF_3$ | Cl | H | H | F | H | Me | H | $CH_2CF_3$ | 0 | 1.5348 |
| I-361 | H | $CF_3$ | Cl | H | H | F | H | Me | H | $CH_2CF_3$ | 1 | 107-109 |
| I-362 | H | H | $CF_3$ | H | H | H | H | F | H | $CH_2Pr\text{-}c$ | 0 | 34-35 |
| I-363 | H | H | $CF_3$ | H | H | H | H | F | H | $CH_2Pr\text{-}c$ | 1 | 49-51 |
| I-364 | H | H | $CF_3$ | H | H | H | H | F | H | $CH_2CF_3$ | 0 | 1.5140 |
| I-365 | H | H | $CF_3$ | H | H | H | H | F | H | $CH_2CF_3$ | 1 | |

TABLE 12

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-366 | H | H | $CF_3$ | H | H | H | H | F | H | $CH_2CF_3$ | 2 | 76-78 |
| I-367 | H | H | $CF_3$ | H | H | F | H | F | H | $CH_2Pr\text{-}c$ | 0 | 1.5395 |
| I-368 | H | H | $CF_3$ | H | H | F | H | F | H | $CH_2Pr\text{-}c$ | 1 | 73-74 |
| I-369 | H | H | $CF_3$ | H | H | F | H | F | H | $CH_2CF_3$ | 0 | 1.5016 |
| I-370 | H | H | $CF_3$ | H | H | F | H | F | H | $CH_2CF_3$ | 1 | 85-86 |
| I-371 | F | H | $CF_3$ | H | H | H | H | Me | H | $CH_2CF_3$ | 0 | |
| I-372 | F | H | $CF_3$ | H | H | H | H | Me | H | $CH_2CF_3$ | 1 | 107-110 |
| I-373 | F | H | $CF_3$ | H | H | H | H | Me | H | $CH_2Pr\text{-}c$ | 0 | |
| I-374 | F | H | $CF_3$ | H | H | H | H | Me | H | $CH_2Pr\text{-}c$ | 1 | 1.5554 |

TABLE 12-continued

| Compound No. | $A_1$ | $A_2$ | $A_3$ | $A_4$ | $A_5$ | $B_0$ | $B_1$ | $B_2$ | $B_3$ | R | n | m.p. (°C.) or RI ($n_D^{20}$) |
|---|---|---|---|---|---|---|---|---|---|---|---|---|
| I-375 | Cl | H | $CF_3$ | H | Cl | H | H | H | H | $CH_2CF_3$ | 0 | 1.5406 |
| I-376 | Cl | H | $CF_3$ | H | Cl | H | H | H | H | $CH_2CF_3$ | 1 | |
| I-377 | Cl | H | $CF_3$ | H | Cl | H | H | H | H | Pr | 0 | 1.5649 |
| I-378 | Cl | H | $CF_3$ | H | Cl | H | H | H | H | Pr | 1 | |
| I-379 | Cl | H | $CF_3$ | H | Cl | H | H | H | H | $CH_2$Pr-c | 0 | 1.5771 |
| I-380 | Cl | H | $CF_3$ | H | Cl | H | H | H | H | $CH_2$Pr-c | 1 | |
| I-381 | Cl | H | $CF_3$ | H | Cl | H | H | H | H | Et | 0 | 1.5625 |
| I-382 | Cl | H | $CF_3$ | H | Cl | H | H | H | H | Et | 1 | |
| I-383 | H | H | $CF_3$ | H | H | H | H | $CF_3$ | H | $CH_2$Pr-c | 0 | 1.5370 |
| I-384 | H | H | $CF_3$ | H | H | H | H | $CF_3$ | H | $CH_2$Pr-c | 1 | |
| I-385 | H | H | $CF_3$ | H | H | H | H | $CF_3$ | H | $CH_2CF_3$ | 0 | 1.4998 |
| I-386 | H | H | $CF_3$ | H | H | H | H | $CF_3$ | H | $CH_2CF_3$ | 1 | 106-108 |
| I-387 | H | $CF_3$ | Cl | H | H | F | H | Me | H | $CH_2$Pr-c | 0 | 1.5720 |
| I-388 | H | $CF_3$ | Cl | H | H | F | H | Me | H | $CH_2$Pr-c | 1 | 78-80 |
| I-389 | H | H | $CF_3$ | H | H | H | H | H | H | Pr | 0 | 1.5621 |
| I-390 | H | H | $CF_3$ | H | H | H | H | H | H | Pr | 1 | |
| I-391 | H | H | $CF_3$ | H | H | H | $CF_3$ | H | H | $CH_2$Pr-c | 0 | 1.5324 |
| I-392 | H | H | $CF_3$ | H | H | H | $CF_3$ | H | H | $CH_2$Pr-c | 1 | 1.5256 |
| I-393 | H | H | $CF_3$ | H | H | H | $CF_3$ | H | H | $CH_2CF_3$ | 0 | 1.4942 |
| I-394 | H | H | $CF_3$ | H | H | H | $CF_3$ | H | H | $CH_2CF_3$ | 1 | 96-97 |
| I-395 | H | H | $CF_3$ | H | H | H | $CF_3$ | H | H | Bu-i | 0 | 1.5121 |
| I-396 | H | H | $CF_3$ | H | H | H | $CF_3$ | H | H | Bu-i | 1 | |
| I-397 | H | H | $CF_3$ | H | H | H | $CF_3$ | H | H | Et | 0 | 38-39 |
| I-398 | H | H | $CF_3$ | H | H | H | $CF_3$ | H | H | Et | 1 | |
| I-399 | H | H | $CF_3$ | H | H | H | $CF_3$ | H | H | Pr-i | 0 | 1.5129 |

TABLE 13

| Compound No. | $A_1$ | $A_2$ | $A_3$ | $A_4$ | $A_5$ | $B_0$ | $B_1$ | $B_2$ | $B_3$ | R | n | m.p. (°C.) or RI ($n_D^{20}$) |
|---|---|---|---|---|---|---|---|---|---|---|---|---|
| I-400 | H | H | $CF_3$ | H | H | H | $CF_3$ | H | H | Pr-i | 1 | |
| I-401 | H | H | $CF_3$ | H | H | H | $CF_3$ | H | H | Bu-t | 0 | 65-68 |
| I-402 | H | H | $CF_3$ | H | H | H | $CF_3$ | H | H | Bu-t | 1 | |
| I-403 | $NO_2$ | H | $CF_3$ | H | H | H | H | Me | H | $CH_2CF_3$ | 0 | 87-88 |
| I-404 | $NO_2$ | H | $CF_3$ | H | H | H | H | Me | H | $CH_2CF_3$ | 1 | |
| I-405 | $NH_2$ | H | $CF_3$ | H | H | H | H | Me | H | $CH_2CF_3$ | 0 | 1.5421 |
| I-406 | $NH_2$ | H | $CF_3$ | H | H | H | H | Me | H | $CH_2CF_3$ | 1 | 116-117 |
| I-407 | H | H | $CF_3$ | H | H | F | H | F | H | Pr | 0 | 1.5332 |
| I-408 | H | H | $CF_3$ | H | H | F | H | F | H | Pr | 1 | 73-74 |
| I-409 | H | H | $CF_3$ | H | H | F | H | F | H | $CH_2CF_2CHF_2$ | 0 | |
| I-410 | H | H | $CF_3$ | H | H | F | H | F | H | $CH_2CF_2CHF_2$ | 1 | |
| I-411 | H | $CF_3$ | Cl | H | H | H | H | H | H | $CH_2CF_3$ | 0 | 1.5472 |
| I-412 | H | $CF_3$ | Cl | H | H | H | H | H | H | $CH_2CF_3$ | 1 | |
| I-413 | H | F | $CF_3$ | H | H | F | H | Me | H | $CH_2CF_3$ | 0 | 1.4982 |
| I-414 | H | F | $CF_3$ | H | H | F | H | Me | H | $CH_2CF_3$ | 1 | 132-133 |
| I-415 | H | F | $CF_3$ | H | H | H | H | Me | H | $CH_2CF_3$ | 0 | |
| I-416 | H | F | $CF_3$ | H | H | H | H | Me | H | $CH_2CF_3$ | 1 | |
| I-417 | H | H | $OCF_3$ | H | H | F | H | Cl | H | $CH_2CF_3$ | 0 | 1.5181 |
| I-418 | H | H | $OCF_3$ | H | H | F | H | Cl | H | $CH_2CF_3$ | 1 | 100-101 |
| I-419 | H | H | $OCF_3$ | H | H | H | H | H | H | $CH_2CF_3$ | 0 | 1.5216 |
| I-420 | H | H | $OCF_3$ | H | H | H | H | H | H | $CH_2CF_3$ | 1 | |
| I-421 | H | H | $OCF_3$ | H | H | Me | H | Cl | H | $CH_2CF_3$ | 0 | 1.5216 |
| I-422 | H | H | $OCF_3$ | H | H | Me | H | Cl | H | $CH_2CF_3$ | 1 | 141-143 |
| I-423 | H | H | $OCF_3$ | H | H | H | H | Cl | H | $CH_2CF_3$ | 0 | |
| I-424 | H | H | $OCF_3$ | H | H | H | H | Cl | H | $CH_2CF_3$ | 1 | |
| I-425 | H | H | $OCF_3$ | H | H | Cl | H | Me | H | $CH_2CF_3$ | 0 | 1.5239 |
| I-426 | H | H | $OCF_3$ | H | H | Cl | H | Me | H | $CH_2CF_3$ | 1 | 151-153 |
| I-427 | H | H | $OCF_3$ | H | H | H | H | Me | H | $CH_2CF_3$ | 0 | 1.5161 |
| I-428 | H | H | $OCF_3$ | H | H | H | H | Me | H | $CH_2CF_3$ | 1 | 95-98 |
| I-429 | H | H | $OCF_3$ | H | H | Cl | H | Cl | H | $CH_2CF_3$ | 0 | 1.5324 |
| I-430 | H | H | $OCF_3$ | H | H | Cl | H | Cl | H | $CH_2CF_3$ | 1 | 129-131 |
| I-431 | H | H | $OCF_3$ | H | H | F | H | Cl | H | $CH_2$Pr-c | 0 | |
| I-432 | H | H | $OCF_3$ | H | H | F | H | Cl | H | $CH_2$Pr-c | 1 | |
| I-433 | H | H | $OCF_3$ | H | H | H | H | H | H | $CH_2$Pr-c | 0 | |

TABLE 14

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-434 | H | H | OCF₃ | H | H | H | H | H | H | CH₂Pr-c | 1 | |
| I-435 | H | H | OCF₃ | H | H | Me | H | Cl | H | CH₂Pr-c | 0 | |
| I-436 | H | H | OCF₃ | H | H | Me | H | Cl | H | CH₂Pr-c | 1 | |
| I-437 | H | H | OCF₃ | H | H | H | H | Cl | H | CH₂Pr-c | 0 | |
| I-438 | H | H | OCF₃ | H | H | H | H | Cl | H | CH₂Pr-c | 1 | |
| I-439 | H | H | OCF₃ | H | H | Cl | H | Me | H | CH₂Pr-c | 0 | |
| I-440 | H | H | OCF₃ | H | H | Cl | H | Me | H | CH₂Pr-c | 1 | |
| I-441 | H | H | OCF₃ | H | H | H | H | Me | H | CH₂Pr-c | 0 | |
| I-442 | H | H | OCF₃ | H | H | H | H | Me | H | CH₂Pr-c | 1 | |
| I-443 | H | H | OCF₃ | H | H | Cl | H | Cl | H | CH₂Pr-c | 0 | |
| I-444 | H | H | OCF₃ | H | H | Cl | H | Cl | H | CH₂Pr-c | 1 | |
| I-445 | H | H | OCHF₂ | H | H | F | H | Me | H | CH₂CF₃ | 0 | 1.5311 |
| I-446 | H | H | OCHF₂ | H | H | F | H | Me | H | CH₂CF₃ | 1 | 91-92 |
| I-447 | H | H | OCHF₂ | H | H | F | H | Cl | H | CH₂CF₃ | 0 | |
| I-448 | H | H | OCHF₂ | H | H | F | H | Cl | H | CH₂CF₃ | 1 | |
| I-449 | H | H | OCHF₂ | H | H | H | H | H | H | CH₂CF₃ | 0 | |
| I-450 | H | H | OCHF₂ | H | H | H | H | H | H | CH₂CF₃ | 1 | |
| I-451 | H | H | OCHF₂ | H | H | Me | H | Cl | H | CH₂CF₃ | 0 | 1.5488 |
| I-452 | H | H | OCHF₂ | H | H | Me | H | Cl | H | CH₂CF₃ | 1 | 125-128 |
| I-453 | H | H | OCHF₂ | H | H | H | H | Cl | H | CH₂CF₃ | 0 | |
| I-454 | H | H | OCHF₂ | H | H | H | H | Cl | H | CH₂CF₃ | 1 | |
| I-455 | H | H | OCHF₂ | H | H | Cl | H | Me | H | CH₂CF₃ | 0 | 1.5540 |
| I-456 | H | H | OCHF₂ | H | H | Cl | H | Me | H | CH₂CF₃ | 1 | 113-114 |
| I-457 | H | H | OCHF₂ | H | H | H | H | Me | H | CH₂CF₃ | 0 | |
| I-458 | H | H | OCHF₂ | H | H | H | H | Me | H | CH₂CF₃ | 1 | |
| I-459 | H | H | OCHF₂ | H | H | Cl | H | Cl | H | CH₂CF₃ | 0 | |
| I-460 | H | H | OCHF₂ | H | H | Cl | H | Cl | H | CH₂CF₃ | 1 | |
| I-461 | H | H | OCHF₂ | H | H | F | H | Me | H | CH₂Pr-c | 0 | |
| I-462 | H | H | OCHF₂ | H | H | F | H | Me | H | CH₂Pr-c | 1 | |
| I-463 | H | H | OCHF₂ | H | H | F | H | Cl | H | CH₂Pr-c | 0 | |
| I-464 | H | H | OCHF₂ | H | H | F | H | Cl | H | CH₂Pr-c | 1 | |
| I-465 | H | H | OCHF₂ | H | H | H | H | H | H | CH₂Pr-c | 0 | |
| I-466 | H | H | OCHF₂ | H | H | H | H | H | H | CH₂Pr-c | 1 | |
| I-467 | H | H | OCHF₂ | H | H | Me | H | Cl | H | CH₂Pr-c | 0 | |

TABLE 15

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-468 | H | H | OCHF₂ | H | H | Me | H | Cl | H | CH₂Pr-c | 1 | |
| I-469 | H | H | OCHF₂ | H | H | H | H | Cl | H | CH₂Pr-c | 0 | |
| I-470 | H | H | OCHF₂ | H | H | H | H | Cl | H | CH₂Pr-c | 1 | |
| I-471 | H | H | OCHF₂ | H | H | Cl | H | Me | H | CH₂Pr-c | 0 | |
| I-472 | H | H | OCHF₂ | H | H | Cl | H | Me | H | CH₂Pr-c | 1 | |
| I-473 | H | H | OCHF₂ | H | H | H | H | Me | H | CH₂Pr-c | 0 | |
| I-474 | H | H | OCHF₂ | H | H | H | H | Me | H | CH₂Pr-c | 1 | |
| I-475 | H | H | OCHF₂ | H | H | Cl | H | Cl | H | CH₂Pr-c | 0 | |
| I-476 | H | H | OCHF₂ | H | H | Cl | H | Cl | H | CH₂Pr-c | 1 | |
| I-477 | H | H | Br | H | H | F | H | Me | H | CH₂CF₃ | 0 | 1.5822 |
| I-478 | H | H | Br | H | H | F | H | Me | H | CH₂CF₃ | 1 | 115-117 |
| I-479 | H | H | Br | H | H | F | H | Cl | H | CH₂CF₃ | 0 | |
| I-480 | H | H | Br | H | H | F | H | Cl | H | CH₂CF₃ | 1 | |
| I-481 | H | H | Br | H | H | H | H | H | H | CH₂CF₃ | 0 | |
| I-482 | H | H | Br | H | H | H | H | H | H | CH₂CF₃ | 1 | |
| I-483 | H | H | Br | H | H | Me | H | Cl | H | CH₂CF₃ | 0 | |
| I-484 | H | H | Br | H | H | Me | H | Cl | H | CH₂CF₃ | 1 | |
| I-485 | H | H | Br | H | H | H | H | Cl | H | CH₂CF₃ | 0 | |
| I-486 | H | H | Br | H | H | H | H | Cl | H | CH₂CF₃ | 1 | |
| I-487 | H | H | Br | H | H | Cl | H | Me | H | CH₂CF₃ | 0 | |
| I-488 | H | H | Br | H | H | Cl | H | Me | H | CH₂CF₃ | 1 | |
| I-489 | H | H | Br | H | H | H | H | Me | H | CH₂CF₃ | 0 | |
| I-490 | H | H | Br | H | H | H | H | Me | H | CH₂CF₃ | 1 | |
| I-491 | H | H | Br | H | H | Cl | H | Cl | H | CH₂CF₃ | 0 | |
| I-492 | H | H | Br | H | H | Cl | H | Cl | H | CH₂CF₃ | 1 | |
| I-493 | H | H | Br | H | H | F | H | Me | H | CH₂Pr-c | 0 | |
| I-494 | H | H | Br | H | H | F | H | Me | H | CH₂Pr-c | 1 | |

TABLE 15-continued

| Compound No. | $A_1$ | $A_2$ | $A_3$ | $A_4$ | $A_5$ | $B_0$ | $B_1$ | $B_2$ | $B_3$ | R | n | m.p. (°C.) or RI ($n_D^{20}$) |
|---|---|---|---|---|---|---|---|---|---|---|---|---|
| I-495 | H | H | Br | H | H | F | H | Cl | H | CH$_2$Pr-c | 0 | |
| I-496 | H | H | Br | H | H | F | H | Cl | H | CH$_2$Pr-c | 1 | |
| I-497 | H | H | Br | H | H | H | H | H | H | CH$_2$Pr-c | 0 | |
| I-498 | H | H | Br | H | H | H | H | H | H | CH$_2$Pr-c | 1 | |
| I-499 | H | H | Br | H | H | Me | H | Cl | H | CH$_2$Pr-c | 0 | |
| I-500 | H | H | Br | H | H | Me | H | Cl | H | CH$_2$Pr-c | 1 | |
| I-501 | H | H | Br | H | H | H | H | Cl | H | CH$_2$Pr-c | 0 | |

TABLE 16

| Compound No. | $A_1$ | $A_2$ | $A_3$ | $A_4$ | $A_5$ | $B_0$ | $B_1$ | $B_2$ | $B_3$ | R | n | m.p. (°C.) or RI ($n_D^{20}$) |
|---|---|---|---|---|---|---|---|---|---|---|---|---|
| I-502 | H | H | Br | H | H | H | H | Cl | H | CH$_2$Pr-c | 1 | |
| I-503 | H | H | Br | H | H | Cl | H | Me | H | CH$_2$Pr-c | 0 | |
| I-504 | H | H | Br | H | H | Cl | H | Me | H | CH$_2$Pr-c | 1 | |
| I-505 | H | H | Br | H | H | H | H | Me | H | CH$_2$Pr-c | 0 | |
| I-506 | H | H | Br | H | H | H | H | Me | H | CH$_2$Pr-c | 1 | |
| I-507 | H | H | Br | H | H | Cl | H | Cl | H | CH$_2$Pr-c | 0 | |
| I-508 | H | H | Br | H | H | Cl | H | Cl | H | CH$_2$Pr-c | 1 | |
| I-509 | H | H | Cl | H | H | F | H | Cl | H | CH$_2$CF$_3$ | 0 | |
| I-510 | H | H | Cl | H | H | F | H | Cl | H | CH$_2$CF$_3$ | 1 | |
| I-511 | H | H | Cl | H | H | H | H | H | H | CH$_2$CF$_3$ | 0 | |
| I-512 | H | H | Cl | H | H | H | H | H | H | CH$_2$CF$_3$ | 1 | |
| I-513 | H | H | Cl | H | H | Me | H | Cl | H | CH$_2$CF$_3$ | 0 | 1.5850 |
| I-514 | H | H | Cl | H | H | Me | H | Cl | H | CH$_2$CF$_3$ | 1 | 163-165 |
| I-515 | H | H | Cl | H | H | H | H | Cl | H | CH$_2$CF$_3$ | 0 | |
| I-516 | H | H | Cl | H | H | H | H | Cl | H | CH$_2$CF$_3$ | 1 | |
| I-517 | H | H | Cl | H | H | Cl | H | Me | H | CH$_2$CF$_3$ | 0 | 1.5981 |
| I-518 | H | H | Cl | H | H | Cl | H | Me | H | CH$_2$CF$_3$ | 1 | 193-194 |
| I-519 | H | H | Cl | H | H | H | H | Me | H | CH$_2$CF$_3$ | 0 | |
| I-520 | H | H | Cl | H | H | H | H | Me | H | CH$_2$CF$_3$ | 1 | |
| I-521 | H | H | Cl | H | H | Cl | H | Cl | H | CH$_2$CF$_3$ | 0 | |
| I-522 | H | H | Cl | H | H | Cl | H | Cl | H | CH$_2$CF$_3$ | 1 | |
| I-523 | H | H | Cl | H | H | F | H | Cl | H | CH$_2$Pr-c | 0 | |
| I-524 | H | H | Cl | H | H | F | H | Cl | H | CH$_2$Pr-c | 1 | |
| I-525 | H | H | Cl | H | H | H | H | H | H | CH$_2$Pr-c | 0 | |
| I-526 | H | H | Cl | H | H | H | H | H | H | CH$_2$Pr-c | 1 | |
| I-527 | H | H | Cl | H | H | Me | H | Cl | H | CH$_2$Pr-c | 0 | |
| I-528 | H | H | Cl | H | H | Me | H | Cl | H | CH$_2$Pr-c | 1 | |
| I-529 | H | H | Cl | H | H | H | H | Cl | H | CH$_2$Pr-c | 0 | |
| I-530 | H | H | Cl | H | H | H | H | Cl | H | CH$_2$Pr-c | 1 | |
| I-531 | H | H | Cl | H | H | Cl | H | Me | H | CH$_2$Pr-c | 0 | |
| I-532 | H | H | Cl | H | H | Cl | H | Me | H | CH$_2$Pr-c | 1 | |
| I-533 | H | H | Cl | H | H | H | H | Me | H | CH$_2$Pr-c | 0 | |
| I-534 | H | H | Cl | H | H | H | H | Me | H | CH$_2$Pr-c | 1 | |
| I-535 | H | H | Cl | H | H | H | H | H | H | Et | 0 | 1.6485 |

TABLE 17

| Compound No. | $A_1$ | $A_2$ | $A_3$ | $A_4$ | $A_5$ | $B_0$ | $B_1$ | $B_2$ | $B_3$ | R | n | m.p. (°C.) or RI ($n_D^{20}$) |
|---|---|---|---|---|---|---|---|---|---|---|---|---|
| I-536 | H | H | Cl | H | H | H | H | H | H | Et | 1 | |
| I-537 | H | H | F | H | H | F | H | Me | H | CH$_2$CF$_3$ | 0 | 1.5450 |
| I-538 | H | H | F | H | H | F | H | Me | H | CH$_2$CF$_3$ | 1 | 112-113 |
| I-539 | H | H | F | H | H | F | H | Cl | H | CH$_2$CF$_3$ | 0 | |
| I-540 | H | H | F | H | H | F | H | Cl | H | CH$_2$CF$_3$ | 1 | |
| I-541 | H | H | F | H | H | H | H | H | H | CH$_2$CF$_3$ | 0 | |
| I-542 | H | H | F | H | H | H | H | H | H | CH$_2$CF$_3$ | 1 | |
| I-543 | H | H | F | H | H | Me | H | Cl | H | CH$_2$CF$_3$ | 0 | 1.5648 |
| I-544 | H | H | F | H | H | Me | H | Cl | H | CH$_2$CF$_3$ | 1 | 133-134 |
| I-545 | H | H | F | H | H | H | H | Cl | H | CH$_2$CF$_3$ | 0 | |
| I-546 | H | H | F | H | H | H | H | Cl | H | CH$_2$CF$_3$ | 1 | |

TABLE 17-continued

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-547 | H | H | F | H | H | Cl | H | Me | H | $CH_2CF_3$ | 0 | 1.5599 |
| I-548 | H | H | F | H | H | Cl | H | Me | H | $CH_2CF_3$ | 1 | 136-137 |
| I-549 | H | H | F | H | H | H | H | Me | H | $CH_2CF_3$ | 0 | |
| I-550 | H | H | F | H | H | H | H | Me | H | $CH_2CF_3$ | 1 | |
| I-551 | H | H | F | H | H | Cl | H | Cl | H | $CH_2CF_3$ | 0 | |
| I-552 | H | H | F | H | H | Cl | H | Cl | H | $CH_2CF_3$ | 1 | |
| I-553 | H | H | F | H | H | F | H | Me | H | $CH_2Pr$-c | 0 | |
| I-554 | H | H | F | H | H | F | H | Me | H | $CH_2Pr$-c | 1 | |
| I-555 | H | H | F | H | H | F | H | Cl | H | $CH_2Pr$-c | 0 | |
| I-556 | H | H | F | H | H | F | H | Cl | H | $CH_2Pr$-c | 1 | |
| I-557 | H | H | F | H | H | H | H | H | H | $CH_2Pr$-c | 0 | |
| I-558 | H | H | F | H | H | H | H | H | H | $CH_2Pr$-c | 1 | |
| I-559 | H | H | F | H | H | Me | H | Cl | H | $CH_2Pr$-c | 0 | |
| I-560 | H | H | F | H | H | Me | H | Cl | H | $CH_2Pr$-c | 1 | |
| I-561 | H | H | F | H | H | H | H | Cl | H | $CH_2Pr$-c | 0 | |
| I-562 | H | H | F | H | H | H | H | Cl | H | $CH_2Pr$-c | 1 | |
| I-563 | H | H | F | H | H | Cl | H | Me | H | $CH_2Pr$-c | 0 | |
| I-564 | H | H | F | H | H | Cl | H | Me | H | $CH_2Pr$-c | 1 | |
| I-565 | H | H | F | H | H | H | H | Me | H | $CH_2Pr$-c | 0 | |
| I-566 | H | H | F | H | H | H | H | Me | H | $CH_2Pr$-c | 1 | |
| I-567 | H | H | F | H | H | Cl | H | Cl | H | $CH_2Pr$-c | 0 | |
| I-568 | H | H | F | H | H | Cl | H | Cl | H | $CH_2Pr$-c | 1 | |
| I-569 | $NH_2$ | H | $CF_3$ | H | H | Cl | H | Me | H | $CH_2CF_3$ | 0 | |

TABLE 18

| Compound No. | $A_1$ | $A_2$ | $A_3$ | $A_4$ | $A_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| I-570 | $NH_2$ | H | $CF_3$ | H | H | Cl | H | Me | H | $CH_2CF_3$ | 1 | |
| I-571 | $NH_2$ | H | $CF_3$ | H | H | F | H | Me | H | $CH_2CF_3$ | 0 | 1.5284 |
| I-572 | $NH_2$ | H | $CF_3$ | H | H | F | H | Me | H | $CH_2CF_3$ | 1 | 142-144 |
| I-573 | Cl | H | $CF_3$ | H | H | H | H | H | H | $CH_2CF_3$ | 0 | 1.5119 |
| I-574 | Cl | H | $CF_3$ | H | H | H | H | H | H | $CH_2CF_3$ | 1 | |
| I-575 | F | H | $CF_3$ | H | H | F | H | Me | H | $CH_2CF_3$ | 0 | 43-45 |
| I-576 | F | H | $CF_3$ | H | H | F | H | Me | H | $CH_2CF_3$ | 1 | 116-117 |
| I-577 | H | H | $CF_3$ | H | H | H | Cl | H | H | $CH_2CF_3$ | 0 | 1.5361 |
| I-578 | H | H | $CF_3$ | H | H | H | Cl | H | H | $CH_2CF_3$ | 1 | |
| I-579 | H | H | $CF_3$ | H | H | H | Me | H | H | $CH_2CF_3$ | 0 | 1.5268 |
| I-580 | H | H | $CF_3$ | H | H | H | Me | H | H | $CH_2CF_3$ | 1 | |
| I-581 | H | H | $CF_3$ | H | H | H | H | H | Me | $CH_2CF_3$ | 0 | 1.5247 |
| I-582 | H | H | $CF_3$ | H | H | H | H | H | Me | $CH_2CF_3$ | 1 | |
| I-583 | H | H | $CF_3$ | H | H | H | H | H | Cl | $CH_2CF_3$ | 0 | 44-47 |
| I-584 | H | H | $CF_3$ | H | H | H | H | H | Cl | $CH_2CF_3$ | 1 | |
| I-585 | H | H | $CF_3$ | H | H | Cl | H | H | H | Et | 0 | 52-55 |
| I-586 | H | H | $CF_3$ | H | H | Cl | H | H | H | Et | 1 | 1.5691 |
| I-587 | H | H | $CF_3$ | H | H | Cl | H | H | H | $CH_2CF_3$ | 0 | 1.5326 |
| I-588 | H | H | $CF_3$ | H | H | Cl | H | H | H | $CH_2CF_3$ | 1 | 84-88 |
| I-589 | H | H | $CF_3$ | H | H | Cl | H | H | H | $CH_2Pr$-c | 0 | 1.5719 |
| I-590 | H | H | $CF_3$ | H | H | Cl | H | H | H | $CH_2Pr$-c | 1 | |
| I-591 | H | H | $CF_3$ | H | H | Cl | H | H | H | Pr | 0 | 1.5601 |
| I-592 | H | H | $CF_3$ | H | H | Cl | H | H | H | Pr | 1 | |
| I-593 | H | H | $CF_3$ | H | H | F | H | Cl | H | $CHClCF_3$ | 0 | 1.5316 |
| I-594 | H | H | $CF_3$ | H | H | F | H | Cl | H | $CHClCF_3$ | 1 | |
| I-595 | H | H | $CF_3$ | H | H | F | H | Cl | H | $(CH_2)_3Cl$ | 0 | 1.5722 |
| I-596 | H | H | $CF_3$ | H | H | F | H | Cl | H | $(CH_2)_3Cl$ | 1 | |
| I-597 | H | Cl | $CF_3$ | H | H | H | H | H | H | Et | 0 | 1.5810 |
| I-598 | H | Cl | $CF_3$ | H | H | H | H | H | H | Et | 1 | |
| I-599 | H | $OCF_3$ | H | H | H | F | H | Me | H | $CH_2CF_3$ | 0 | 1.4869 |
| I-600 | H | $OCF_3$ | H | H | H | F | H | Me | H | $CH_2CF_3$ | 1 | 77-78 |
| I-601 | H | $OCHF_2$ | H | H | H | F | H | Me | H | $CH_2CF_3$ | 0 | |
| I-602 | H | $OCHF_2$ | H | H | H | F | H | Me | H | $CH_2CF_3$ | 1 | |
| I-603 | H | H | $OCF_3$ | H | H | $CF_3$ | H | H | H | Et | 0 | 1.5129 |

TABLE 19

| Compound No. | $A_1$ | $A_2$ | $A_3$ | $A_4$ | $A_5$ | $B_0$ | $B_1$ | $B_2$ | $B_3$ | R | n | m.p. (°C.) or RI ($n_D^{20}$) |
|---|---|---|---|---|---|---|---|---|---|---|---|---|
| I-604 | H | H | OCF$_3$ | H | H | CF$_3$ | H | H | H | Et | 1 | |
| I-605 | H | H | OCF$_3$ | H | H | CF$_3$ | H | H | H | CH$_2$CF$_3$ | 0 | 1.4801 |
| I-606 | H | H | OCF$_3$ | H | H | CF$_3$ | H | H | H | CH$_2$CF$_3$ | 1 | 66-67 |
| I-607 | H | H | OCF$_3$ | H | H | CF$_3$ | H | H | H | CH$_2$Pr-c | 0 | 1.5208 |
| I-608 | H | H | OCF$_3$ | H | H | CF$_3$ | H | H | H | CH$_2$Pr-c | 1 | |
| I-609 | H | H | CF$_3$ | H | H | F | H | Me | H | Pr-c | 0 | |
| I-610 | H | H | CF$_3$ | H | H | F | H | Me | H | Pr-c | 1 | |
| I-611 | H | H | CF$_3$ | H | H | F | H | Cl | H | Pr-c | 0 | |
| I-612 | H | H | CF$_3$ | H | H | F | H | Cl | H | Pr-c | 1 | |
| I-613 | H | H | CF$_3$ | H | H | Me | H | Cl | H | CF$_2$CH$_3$ | 0 | |
| I-614 | H | H | CF$_3$ | H | H | Me | H | Cl | H | CF$_2$CH$_3$ | 1 | |
| I-615 | H | H | CF$_3$ | H | H | H | H | Cl | H | CF$_2$CH$_3$ | 0 | |
| I-616 | H | H | CF$_3$ | H | H | H | H | Cl | H | CF$_2$CH$_3$ | 1 | |
| I-617 | H | H | CF$_3$ | H | H | Cl | H | Me | H | CF$_2$CH$_3$ | 0 | |
| I-618 | H | H | CF$_3$ | H | H | Cl | H | Me | H | CF$_2$CH$_3$ | 1 | |
| I-619 | H | H | CF$_3$ | H | H | H | H | Me | H | CF$_2$CH$_3$ | 0 | |
| I-620 | H | H | CF$_3$ | H | H | H | H | Me | H | CF$_2$CH$_3$ | 1 | |
| I-621 | H | H | CF$_3$ | H | H | Cl | Br | H | H | Et | 0 | 48-49 |
| I-622 | H | H | CF$_3$ | H | H | Cl | Br | H | H | Et | 1 | |
| I-623 | H | H | CF$_3$ | H | H | H | H | H | H | C$_2$F$_5$ | 0 | 1.5921 |
| I-624 | H | H | CF$_3$ | H | H | H | H | H | H | C$_2$F$_5$ | 1 | 1.5058 |
| I-625 | H | H | CF$_3$ | H | H | Me | H | Cl | H | CH$_2$CF$_3$ | 2 | 122-123 |
| I-626 | H | CF$_3$ | F | H | H | F | H | Me | H | CH$_2$CF$_3$ | 0 | 1.5089 |
| I-627 | H | CF$_3$ | F | H | H | F | H | Me | H | CH$_2$CF$_3$ | 1 | 104-105 |
| I-628 | H | H | CF$_3$ | H | H | CF$_3$ | H | H | H | Et | 0 | 1.5179 |
| I-629 | H | H | CF$_3$ | H | H | CF$_3$ | H | H | H | Et | 1 | 1.5190 |
| I-630 | H | H | CF$_3$ | H | H | H | H | H | H | Et | 0 | 1.5592 |
| I-631 | H | H | CF$_3$ | H | H | H | H | H | H | Et | 1 | 1.5576 |
| I-632 | H | H | H | H | H | Me | H | Cl | H | CH$_2$CF$_3$ | 0 | 1.5630 |
| I-633 | H | H | H | H | H | Me | H | Cl | H | CH$_2$CF$_3$ | 1 | 106-108 |
| I-634 | H | H | H | H | H | Cl | H | Me | H | CH$_2$CF$_3$ | 0 | 1.5712 |
| I-635 | H | H | H | H | H | Cl | H | Me | H | CH$_2$CF$_3$ | 1 | 126-129 |
| I-636 | H | H | H | H | H | F | H | Me | H | CH$_2$CF$_3$ | 0 | 1.5569 |
| I-637 | H | H | H | H | H | F | H | Me | H | CH$_2$CF$_3$ | 1 | 98-100 |

TABLE 20

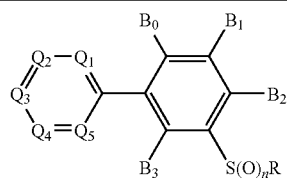

| Compound No. | $Q_1$ | $Q_2$ | $Q_3$ | $Q_4$ | $Q_5$ | $B_0$ | $B_1$ | $B_2$ | $B_3$ | R | n | m.p. (°C.) or RI ($n_n^{20}$) |
|---|---|---|---|---|---|---|---|---|---|---|---|---|
| II-1 | C—H | C—H | C—CF$_3$ | C—H | N | H | H | CN | H | Pr-i | 0 | 1.5598 |
| II-2 | C—H | C—H | C—CF$_3$ | C—H | N | H | H | CN | H | Pr-i | 1 | |
| II-3 | C—H | C—H | C—CF$_3$ | C—H | N | H | H | CN | H | Pr | 0 | 116-119 |
| II-4 | C—H | C—H | C—CF$_3$ | C—H | N | H | H | CN | H | Pr | 1 | 121-122 |
| II-5 | C—H | C—H | C—CF$_3$ | C—H | N | H | H | CN | H | CH$_2$Pr-c | 0 | 135-136 |
| II-6 | C—H | C—H | C—CF$_3$ | C—H | N | H | H | CN | H | CH$_2$Pr-c | 1 | 127-128 |
| II-7 | C—H | C—H | C—CF$_3$ | C—H | N | H | H | CN | H | CH$_2$CF$_3$ | 0 | |
| II-8 | C—H | C—H | C—CF$_3$ | C—H | N | H | H | CN | H | CH$_2$CF$_3$ | 1 | |
| II-9 | C—H | C—H | C—CF$_3$ | C—H | N | H | H | CHO | H | Pr-i | 0 | 71-73 |
| II-10 | C—H | C—H | C—CF$_3$ | C—H | N | H | H | CHO | H | Pr-i | 1 | |
| II-11 | C—H | C—H | C—CF$_3$ | C—H | N | H | H | CHO | H | CH$_2$CF$_3$ | 0 | 121-123 |
| II-12 | C—H | C—H | C—CF$_3$ | C—H | N | H | H | CHO | H | CH$_2$CF$_3$ | 1 | |
| II-13 | C—H | C—H | C—CF$_3$ | C—H | N | H | H | CN | H | Et | 0 | |
| II-14 | C—H | C—H | C—CF$_3$ | C—H | N | H | H | CN | H | Pr | 0 | |
| II-15 | C—H | C—H | C—CF$_3$ | C—H | N | H | H | CHF$_2$ | H | Pr-i | 0 | 57-59 |
| II-16 | C—H | C—H | C—CF$_3$ | C—H | N | H | H | CHF$_2$ | H | Pr-i | 1 | 73-74 |
| II-17 | C—H | C—H | C—CF$_3$ | C—H | N | H | H | CHF$_2$ | H | Pr | 0 | |
| II-18 | C—H | C—H | C—CF$_3$ | C—H | N | H | H | CHF$_2$ | H | Pr | 1 | |
| II-19 | C—H | C—H | C—CF$_3$ | C—H | N | H | H | CHF$_2$ | H | CH$_2$CF$_3$ | 0 | 1.5136 |
| II-20 | C—H | C—H | C—CF$_3$ | C—H | N | H | H | CHF$_2$ | H | CH$_2$CF$_3$ | 1 | 116-117 |

TABLE 20-continued

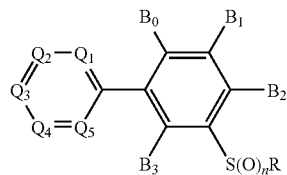

| Compound No. | $Q_1$ | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| II-21 | C—H | C—H | C—CF$_3$ | C—H | N | H | H | CHF$_2$ | H | CH$_2$Pr-c | 0 | |
| II-22 | C—H | C—H | C—CF$_3$ | C—H | N | H | H | CHF$_2$ | H | CH$_2$Pr-c | 1 | |
| II-23 | C—H | C—H | C—CF$_3$ | C—H | N | H | H | Me | H | Pr-i | 0 | |
| II-24 | C—H | C—H | C—CF$_3$ | C—H | N | H | H | Me | H | Pr-i | 1 | |
| II-25 | C—H | C—H | C—CF$_3$ | C—H | N | H | H | Me | H | Pr | 0 | |

TABLE 21

| Compound No. | $Q_1$ | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| II-26 | C—H | C—H | C—CF$_3$ | C—H | N | H | H | Me | H | Pr | 1 | |
| II-27 | C—H | C—H | C—CF$_3$ | C—H | N | H | H | Me | H | CH$_2$CF$_3$ | 0 | 58-59 |
| II-28 | C—H | C—H | C—CF$_3$ | C—H | N | H | H | Me | H | CH$_2$CF$_3$ | 1 | 139-140 |
| II-29 | C—H | C—H | C—CF$_3$ | C—H | N | H | H | Me | H | CH$_2$Pr-c | 0 | |
| II-30 | C—H | C—H | C—CF$_3$ | C—H | N | H | H | Me | H | CH$_2$Pr-c | 1 | |
| II-31 | C—H | C—H | C—CF$_3$ | C—H | N | H | H | Cl | H | Pr-i | 0 | |
| II-32 | C—H | C—H | C—CF$_3$ | C—H | N | H | H | Cl | H | Pr-i | 1 | |
| II-33 | C—H | C—H | C—CF$_3$ | C—H | N | H | H | Cl | H | Pr | 0 | |
| II-34 | C—H | C—H | C—CF$_3$ | C—H | N | H | H | Cl | H | Pr | 1 | |
| II-35 | C—H | C—H | C—CF$_3$ | C—H | N | H | H | Cl | H | CH$_2$CF$_3$ | 0 | |
| II-36 | C—H | C—H | C—CF$_3$ | C—H | N | H | H | Cl | H | CH$_2$CF$_3$ | 1 | |
| II-37 | C—H | C—H | C—CF$_3$ | C—H | N | H | H | Cl | H | CH$_2$Pr-c | 0 | |
| II-38 | C—H | C—H | C—CF$_3$ | C—H | N | H | H | Cl | H | CH$_2$Pr-c | 1 | |
| II-39 | C—H | C—H | C—CF$_3$ | C—H | N | F | H | Me | H | Pr-i | 0 | 52-53 |
| II-40 | C—H | C—H | C—CF$_3$ | C—H | N | F | H | Me | H | Pr-i | 1 | 108-109 |
| II-41 | C—H | C—H | C—CF$_3$ | C—H | N | F | H | Me | H | Pr | 0 | |
| II-42 | C—H | C—H | C—CF$_3$ | C—H | N | F | H | Me | H | Pr | 1 | |
| II-43 | C—H | C—H | C—CF$_3$ | C—H | N | F | H | Me | H | CH$_2$CF$_3$ | 0 | 60-61 |
| II-44 | C—H | C—H | C—CF$_3$ | C—H | N | F | H | Me | H | CH$_2$CF$_3$ | 1 | 138-139 |
| II-45 | C—H | C—H | C—CF$_3$ | C—H | N | F | H | Me | H | CH$_2$Pr-c | 0 | |
| II-46 | C—H | C—H | C—CF$_3$ | C—H | N | F | H | Me | H | CH$_2$Pr-c | 1 | |
| II-47 | C—H | C—H | C—CF$_3$ | C—H | N | F | H | Cl | H | Pr-i | 0 | |
| II-48 | C—H | C—H | C—CF$_3$ | C—H | N | F | H | Cl | H | Pr-i | 1 | |
| II-48 | C—H | C—H | C—CF$_3$ | C—H | N | F | H | Cl | H | Pr | 0 | |
| II-50 | C—H | C—H | C—CF$_3$ | C—H | N | F | H | Cl | H | Pr | 1 | |
| II-51 | C—H | C—H | C—CF$_3$ | C—H | N | F | H | Cl | H | CH$_2$CF$_3$ | 0 | |
| II-52 | C—H | C—H | C—CF$_3$ | C—H | N | F | H | Cl | H | CH$_2$CF$_3$ | 1 | |
| II-53 | C—H | C—H | C—CF$_3$ | C—H | N | F | H | Cl | H | CH$_2$Pr-c | 0 | |
| II-54 | C—H | C—H | C—CF$_3$ | C—H | N | F | H | Cl | H | CH$_2$Pr-c | 1 | |
| II-55 | C—H | C—H | C—H | N | C—H | H | H | CN | H | Pr | 0 | 64-65 |
| II-56 | C—H | C—H | C—H | N | C—H | H | H | CN | H | Pr | 1 | |
| II-57 | C—H | C—H | C—CF$_3$ | N | C—H | F | H | Me | H | Pr-i | 0 | 1.5446 |

TABLE 22

| Compound No. | $Q_1$ | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| II-58 | C—H | C—H | C—CF$_3$ | N | C—H | F | H | Me | H | Pr-i | 1 | 107-108 |
| II-59 | C—H | C—H | C—CF$_3$ | N | C—H | F | H | Me | H | Pr | 0 | |
| II-60 | C—H | C—H | C—CF$_3$ | N | C—H | F | H | Me | H | Pr | 1 | |
| II-61 | C—H | C—H | C—CF$_3$ | N | C—H | F | H | Me | H | CH$_2$CF$_3$ | 0 | 1.5205 |
| II-62 | C—H | C—H | C—CF$_3$ | N | C—H | F | H | Me | H | CH$_2$CF$_3$ | 1 | 103-104 |
| II-63 | C—H | C—H | C—CF$_3$ | N | C—H | F | H | Me | H | CH$_2$Pr-c | 0 | |
| II-64 | C—H | C—H | C—CF$_3$ | N | C—H | F | H | Me | H | CH$_2$Pr-c | 1 | |
| II-65 | C—H | C—H | C—Cl | N | C—H | Cl | H | Me | H | Pr-i | 0 | |
| II-66 | C—H | C—H | C—Cl | N | C—H | Cl | H | Me | H | Pr-i | 1 | |
| II-67 | C—H | C—H | C—Cl | N | C—H | Cl | H | Me | H | Pr | 0 | |

TABLE 22-continued

| Compound No. | $Q_1$ | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| II-68 | C—H | C—H | C—Cl | N | C—H | Cl | H | Me | H | Pr | 1 | |
| II-69 | C—H | C—H | C—Cl | N | C—H | Cl | H | Me | H | $CH_2CF_3$ | 0 | |
| II-70 | C—H | C—H | C—Cl | N | C—H | Cl | H | Me | H | $CH_2CF_3$ | 1 | |
| II-71 | C—H | C—H | C—Cl | N | C—H | Cl | H | Me | H | $CH_2Pr$-c | 0 | |
| II-72 | C—H | C—H | C—Cl | N | C—H | Cl | H | Me | H | $CH_2Pr$-c | 1 | |
| II-73 | N | C—$CF_3$ | C—H | C—H | N | F | H | Me | H | Pr-i | 0 | 36-37 |
| II-74 | N | C—$CF_3$ | C—H | C—H | N | F | H | Me | H | Pr-i | 1 | 135-136 |
| II-75 | N | C—$CF_3$ | C—H | C—H | N | F | H | Me | H | Pr | 0 | |
| II-76 | N | C—$CF_3$ | C—H | C—H | N | F | H | Me | H | Pr | 1 | |
| II-77 | N | C—$CF_3$ | C—H | C—H | N | F | H | Me | H | $CH_2CF_3$ | 0 | 1.5159 |
| II-78 | N | C—$CF_3$ | C—H | C—H | N | F | H | Me | H | $CH_2CF_3$ | 1 | 124-125 |
| II-79 | N | C—$CF_3$ | C—H | C—H | N | F | H | Me | H | $CH_2Pr$-c | 0 | |
| II-80 | N | C—$CF_3$ | C—H | C—H | N | F | H | Me | H | $CH_2Pr$-c | 1 | |
| II-81 | C—H | C—$CF_3$ | N | C—H | N | F | H | Me | H | Pr-i | 0 | 75-76 |
| II-82 | C—H | C—$CF_3$ | N | C—H | N | F | H | Me | H | Pr-i | 1 | 111-113 |
| II-83 | C—H | C—$CF_3$ | N | C—H | N | F | H | Me | H | Pr | 0 | |
| II-84 | C—H | C—$CF_3$ | N | C—H | N | F | H | Me | H | Pr | 1 | |
| II-85 | C—H | C—$CF_3$ | N | C—H | N | F | H | Me | H | $CH_2CF_3$ | 0 | 76-78 |
| II-86 | C—H | C—$CF_3$ | N | C—H | N | F | H | Me | H | $CH_2CF_3$ | 1 | 149-151 |
| II-87 | C—H | C—$CF_3$ | N | C—H | N | F | H | Me | H | $CH_2Pr$-c | 0 | |
| II-88 | C—H | C—$CF_3$ | N | C—H | N | F | H | Me | H | $CH_2Pr$-c | 1 | |
| II-89 | C—H | C—H | N | C—$CF_3$ | N | F | H | Me | H | Pr-i | 0 | 104-105 |

TABLE 23

| Compound No. | $Q_1$ | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|---|
| II-90 | C—H | C—H | N | C—$CF_3$ | N | F | H | Me | H | Pr-i | 1 | 90-91 |
| II-91 | C—H | C—H | N | C—$CF_3$ | N | F | H | Me | H | Pr | 0 | |
| II-92 | C—H | C—H | N | C—$CF_3$ | N | F | H | Me | H | Pr | 1 | |
| II-93 | C—H | C—H | N | C—$CF_3$ | N | F | H | Me | H | $CH_2CF_3$ | 0 | 68-69 |
| II-94 | C—H | C—H | N | C—$CF_3$ | N | F | H | Me | H | $CH_2CF_3$ | 1 | 135-136 |
| II-95 | C—H | C—H | N | C—$CF_3$ | N | F | H | Me | H | $CH_2Pr$-c | 0 | |
| II-96 | C—H | C—H | N | C—$CF_3$ | N | F | H | Me | H | $CH_2Pr$-c | 1 | |

TABLE 24

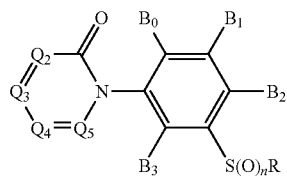

| Compound No. | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|
| III-1 | C—H | C—$CF_3$ | C—H | C—H | H | H | CN | H | Pr | 0 | 107-109 |
| III-2 | C—H | C—$CF_3$ | C—H | C—H | H | H | CN | H | Pr | 1 | |
| III-3 | C—H | C—$CF_3$ | C—H | C—H | H | H | CN | H | Pr-i | 0 | |
| III-4 | C—H | C—$CF_3$ | C—H | C—H | H | H | CN | H | Pr-i | 1 | |
| III-5 | C—H | C—$CF_3$ | C—H | C—H | H | H | CN | H | $CH_2Pr$-c | 0 | |
| III-6 | C—H | C—$CF_3$ | C—H | C—H | H | H | CN | H | $CH_2Pr$-c | 1 | |
| III-7 | C—H | C—$CF_3$ | C—H | C—H | H | H | CN | H | $CH_2CF_3$ | 0 | |
| III-8 | C—H | C—$CF_3$ | C—H | C—H | H | H | CN | H | $CH_2CF_3$ | 1 | |
| III-9 | C—H | C—$CF_3$ | N | C—H | H | H | CN | H | Pr | 0 | 157-158 |
| III-10 | C—H | C—$CF_3$ | N | C—H | H | H | CN | H | Pr | 1 | 161-163 |
| III-11 | C—H | C—$CF_3$ | N | C—H | H | H | CN | H | Pr | 2 | 197-199 |
| III-12 | C—H | C—$CF_3$ | N | C—H | H | H | CN | H | Pr-i | 0 | |
| III-13 | C—H | C—$CF_3$ | N | C—H | H | H | CN | H | Pr-i | 1 | |
| III-14 | C—H | C—$CF_3$ | N | C—H | H | H | CN | H | $CH_2Pr$-c | 0 | 147-149 |
| III-15 | C—H | C—$CF_3$ | N | C—H | H | H | CN | H | $CH_2Pr$-c | 1 | 66-68 |
| III-16 | C—H | C—$CF_3$ | N | C—H | H | H | CN | H | $CH_2Pr$-c | 2 | 179-181 |
| III-17 | C—H | C—$CF_3$ | N | C—H | H | H | CN | H | $CH_2CF_3$ | 0 | |
| III-18 | C—H | C—$CF_3$ | N | C—H | H | H | CN | H | $CH_2CF_3$ | 1 | |

TABLE 24-continued

| Compound No. | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|
| III-19 | C—H | C—CF$_3$ | C—H | C—H | H | H | CHF$_2$ | H | Pr | 0 | |
| III-20 | C—H | C—CF$_3$ | C—H | C—H | H | H | CHF$_2$ | H | Pr | 1 | |
| III-21 | C—H | C—CF$_3$ | C—H | C—H | H | H | CHF$_2$ | H | Pr | 2 | |
| III-22 | C—H | C—CF$_3$ | C—H | C—H | H | H | CHF$_2$ | H | Pr-i | 0 | |
| III-23 | C—H | C—CF$_3$ | C—H | C—H | H | H | CHF$_2$ | H | Pr-i | 1 | |
| III-24 | C—H | C—CF$_3$ | C—H | C—H | H | H | CHF$_2$ | H | CH$_2$Pr-c | 0 | |
| III-25 | C—H | C—CF$_3$ | C—H | C—H | H | H | CHF$_2$ | H | CH$_2$Pr-c | 1 | |
| III-26 | C—H | C—CF$_3$ | C—H | C—H | H | H | CHF$_2$ | H | CH$_2$Pr-c | 2 | |

TABLE 25

| Compound No. | $Q_2$ | $Q_3$ | $Q_4$ | $Q_5$ | $B_0$ | $B_1$ | $B_2$ | $B_3$ | R | n | m.p. (° C.) or RI ($n_D^{20}$) |
|---|---|---|---|---|---|---|---|---|---|---|---|
| III-27 | C—H | C—CF$_3$ | N | C—H | H | H | CHF$_2$ | H | CH$_2$CF$_3$ | 0 | |
| III-28 | C—H | C—CF$_3$ | N | C—H | H | H | CHF$_2$ | H | CH$_2$CF$_3$ | 1 | |
| III-29 | C—H | C—CF$_3$ | N | C—H | H | H | CHF$_2$ | H | Pr | 0 | |
| III-30 | C—H | C—CF$_3$ | N | C—H | H | H | CHF$_2$ | H | Pr | 1 | |
| III-31 | C—H | C—CF$_3$ | N | C—H | H | H | CHF$_2$ | H | Pr-i | 0 | |
| III-32 | C—H | C—CF$_3$ | N | C—H | H | H | CHF$_2$ | H | Pr-i | 1 | |
| III-33 | C—H | C—CF$_3$ | N | C—H | H | H | CHF$_2$ | H | CH$_2$Pr-c | 0 | |
| III-34 | C—H | C—CF$_3$ | N | C—H | H | H | CHF$_2$ | H | CH$_2$Pr-c | 1 | |
| III-35 | C—H | C—CF$_3$ | N | C—H | H | H | CHF$_2$ | H | CH$_2$CF$_3$ | 0 | |
| III-36 | C—H | C—CF$_3$ | N | C—H | H | H | CHF$_2$ | H | CH$_2$CF$_3$ | 1 | |

TABLE 26

| Compound No. | $Q_6$ | $Q_7$ | $A_6$ | $A_9$ | $B_0$ | $B_1$ | $B_2$ | $B_3$ | R | n | m.p.(° C.) or RI ($n_D^{20}$) |
|---|---|---|---|---|---|---|---|---|---|---|---|
| IV-1 | S | C—H | H | H | H | H | CN | H | Pr | 0 | 60-61 |
| IV-2 | S | C—H | H | H | H | H | CN | H | Pr | 1 | |
| IV-3 | S | C—H | H | Cl | H | H | CHO | H | Pr | 0 | 65-66 |
| IV-4 | S | C—H | H | Cl | H | H | CHO | H | Pr | 1 | |
| IV-5 | S | C—H | H | Cl | H | H | CN | H | CH$_2$Pr-c | 0 | 123-124 |
| IV-6 | S | C—H | H | Cl | H | H | CN | H | CH$_2$Pr-c | 1 | 85-87 |
| IV-7 | S | C—H | H | Cl | H | H | CN | H | CH$_2$CF$_3$ | 0 | |
| IV-8 | S | C—H | H | Cl | H | H | CN | H | CH$_2$CF$_3$ | 1 | |
| IV-9 | S | C—H | H | CF$_3$ | H | H | Me | H | CH$_2$Pr-c | 0 | |
| IV-10 | S | C—H | H | CF$_3$ | H | H | Me | H | CH$_2$Pr-c | 1 | |
| IV-11 | S | C—H | H | CF$_3$ | H | H | Me | H | CH$_2$CF$_3$ | 0 | |
| IV-12 | S | C—H | H | CF$_3$ | H | H | Me | H | CH$_2$CF$_3$ | 1 | |
| IV-13 | S | N | H | CF$_3$ | H | H | Me | H | CH$_2$Pr-c | 0 | |
| IV-14 | S | N | H | CF$_3$ | H | H | Me | H | CH$_2$Pr-c | 1 | |
| IV-15 | S | N | H | CF$_3$ | H | H | Me | H | CH$_2$CF$_3$ | 0 | |
| IV-16 | S | N | H | CF$_3$ | H | H | Me | H | CH$_2$CF$_3$ | 1 | |
| IV-17 | O | N | H | CF$_3$ | H | H | Me | H | CH$_2$Pr-c | 0 | |
| IV-18 | O | N | H | CF$_3$ | H | H | Me | H | CH$_2$Pr-c | 1 | |
| IV-19 | O | N | H | CF$_3$ | H | H | CHF$_2$ | H | CH$_2$CF$_3$ | 0 | |

TABLE 26-continued

[Structure: A6-Q7, A9-Q6 five-membered ring attached to benzene with B0, B1, B2, B3 substituents and S(O)nR group]

| Compound No. | Q6 | Q7 | A6 | A9 | B0 | B1 | B2 | B3 | R | n | m.p.(° C.) or RI ($n_D^{20}$) |
|---|---|---|---|---|---|---|---|---|---|---|---|
| IV-20 | O | N | H | CF₃ | H | H | CHF₂ | H | CH₂CF₃ | 1 | |
| IV-21 | O | C—H | H | Cl | H | H | CHF₂ | H | CH₂Pr-c | 0 | |
| IV-22 | O | C—H | H | Cl | H | H | CHF₂ | H | CH₂Pr-c | 1 | |
| IV-23 | O | C—H | H | Cl | H | H | CHF₂ | H | CH₂CF₃ | 0 | |
| IV-24 | O | C—H | H | Cl | H | H | CHF₂ | H | CH₂CF₃ | 1 | |

TABLE 27

[Structure: pyrazole ring with A8, A10, A11 substituents, N-linked to benzene with B0, B1, B2, B3 and S(O)nR]

| Compound No. | A10 | A8 | A11 | R | B0 | B1 | B2 | B3 | n | m.p. (° C.) or RI ($n_D^{20}$) |
|---|---|---|---|---|---|---|---|---|---|---|
| V-1 | H | H | H | Pr | H | H | CN | H | 0 | |
| V-2 | H | H | H | Pr | H | H | CN | H | 1 | |
| V-3 | H | H | H | Pr | H | H | Me | H | 0 | |
| V-4 | H | H | H | Pr | H | H | Me | H | 1 | |
| V-5 | H | H | H | Pr | H | H | CHF₂ | H | 0 | |
| V-6 | H | H | H | Pr | H | H | CHF₂ | H | 1 | |
| V-7 | H | H | H | Pr-c | H | H | CN | H | 0 | |
| V-8 | H | H | H | Pr-c | H | H | CN | H | 1 | |
| V-9 | H | H | H | Pr-c | H | H | Me | H | 0 | |
| V-10 | H | H | H | Pr-c | H | H | Me | H | 1 | |
| V-11 | H | H | H | Pr-c | H | H | CHF₂ | H | 0 | |
| V-12 | H | H | H | Pr-c | H | H | CHF₂ | H | 1 | |
| V-13 | H | H | H | CH₂CF₃ | H | H | CN | H | 0 | 119-120 |
| V-14 | H | H | H | CH₂CF₃ | H | H | CN | H | 1 | 155-156 |
| V-15 | H | H | H | CH₂CF₃ | H | H | Me | H | 0 | |
| V-16 | H | H | H | CH₂CF₃ | H | H | Me | H | 1 | |
| V-17 | H | H | H | CH₂CF₃ | H | H | CHF₂ | H | 0 | |
| V-18 | H | H | H | CH₂CF₃ | H | H | CHF₂ | H | 1 | |
| V-19 | CF₃ | H | H | Et | H | H | CN | H | 0 | 105-107 |
| V-20 | CF₃ | H | H | Pr | H | H | CN | H | 0 | 83-85 |
| V-21 | CF₃ | H | H | Pr-i | H | H | CN | H | 0 | 126-128 |
| V-22 | CF₃ | H | H | Bu | H | H | CN | H | 0 | |
| V-23 | CF₃ | H | H | Bu-i | H | H | CN | H | 0 | |
| V-24 | CF₃ | H | H | Bu-s | H | H | CN | H | 0 | |
| V-25 | CF₃ | H | H | Bu-t | H | H | CN | H | 0 | |

TABLE 28

| Compound No. | A10 | A6 | A11 | R | B0 | B1 | B2 | B3 | n | m.p. (° C.) or RI ($n_D^{20}$) |
|---|---|---|---|---|---|---|---|---|---|---|
| V-26 | CF₃ | H | H | CH₂CH₂Cl | H | H | CN | H | 0 | |
| V-27 | CF₃ | H | H | CH₂CF₃ | H | H | CN | H | 0 | 65-67 |
| V-28 | CF₃ | H | H | Pr-c | H | H | CN | H | 0 | |
| V-29 | CF₃ | H | H | Bu-c | H | H | CN | H | 0 | |
| V-30 | CF₃ | H | H | Pen-c | H | H | CN | H | 0 | |
| V-31 | CF₃ | H | H | Hex-c | H | H | CN | H | 0 | |
| V-32 | CF₃ | H | H | CH₂Pr-c | H | H | CN | H | 0 | 135-137 |
| V-33 | CF₃ | H | H | CH₂Bu-c | H | H | CN | H | 0 | 102-103 |
| V-34 | CF₃ | H | H | CH₂Pen-c | H | H | CN | H | 0 | 78-79 |
| V-35 | CF₃ | H | H | CH₂Hex-c | H | H | CN | H | 0 | 80-81 |
| V-36 | CF₃ | H | H | Et | H | H | CN | H | 1 | 131-134 |
| V-37 | CF₃ | H | H | Pr | H | H | CN | H | 1 | 82-83 |
| V-38 | CF₃ | H | H | Pr-i | H | H | CN | H | 1 | 134-135 |
| V-39 | CF₃ | H | H | Bu | H | H | CN | H | 1 | |
| V-40 | CF₃ | H | H | Bu-i | H | H | CN | H | 1 | |

TABLE 28-continued

| Compound No. | $A_{10}$ | $A_6$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-41 | $CF_3$ | H | H | Bu-s | H | H | CN | H | 1 | |
| V-42 | $CF_3$ | H | H | Bu-t | H | H | CN | H | 1 | |
| V-43 | $CF_3$ | H | H | $CH_2CH_2Cl$ | H | H | CN | H | 1 | |
| V-44 | $CF_3$ | H | H | $CH_2CF_3$ | H | H | CN | H | 1 | 118-120 |
| V-45 | $CF_3$ | H | H | Pr-c | H | H | CN | H | 1 | |
| V-46 | $CF_3$ | H | H | Bu-c | H | H | CN | H | 1 | |
| V-47 | $CF_3$ | H | H | Pen-c | H | H | CN | H | 1 | |
| V-48 | $CF_3$ | H | H | Hex-c | H | H | CN | H | 1 | |
| V-49 | $CF_3$ | H | H | $CH_2$Pr-c | H | H | CN | H | 0 | |
| V-50 | $CF_3$ | H | H | $CH_2$Bu-c | H | H | CN | H | 0 | |
| V-51 | $CF_3$ | H | H | $CH_2$Pen-c | H | H | CN | H | 0 | |
| V-52 | $CF_3$ | H | H | $CH_2$Hex-c | H | H | CN | H | 0 | |
| V-53 | $CF_3$ | H | H | $CH_2$Pr-c | H | H | CN | H | 1 | 98-99 |
| V-54 | $CF_3$ | H | H | $CH_2$Bu-c | H | H | CN | H | 1 | 88-91 |
| V-55 | $CF_3$ | H | H | $CH_2$Pen-c | H | H | CN | H | 1 | 108-110 |
| V-56 | $CF_3$ | H | H | $CH_2$Hex-c | H | H | CN | H | 1 | 110-112 |

TABLE 29

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-57 | $CF_3$ | H | H | Et | H | H | CN | H | 2 | |
| V-58 | $CF_3$ | H | H | Pr | H | H | CN | H | 2 | |
| V-59 | $CF_3$ | H | H | Pr-i | H | H | CN | H | 2 | |
| V-60 | $CF_3$ | H | H | Bu | H | H | CN | H | 2 | |
| V-61 | $CF_3$ | H | H | Bu-i | H | H | CN | H | 2 | |
| V-62 | $CF_3$ | H | H | Bu-s | H | H | CN | H | 2 | |
| V-63 | $CF_3$ | H | H | Bu-t | H | H | CN | H | 2 | |
| V-64 | $CF_3$ | H | H | $CH_2CH_2Cl$ | H | H | CN | H | 2 | |
| V-65 | $CF_3$ | H | H | $CH_2CF_3$ | H | H | CN | H | 2 | |
| V-66 | $CF_3$ | H | H | Pr-c | H | H | CN | H | 2 | |
| V-67 | $CF_3$ | H | H | Bu-c | H | H | CN | H | 2 | |
| V-68 | $CF_3$ | H | H | Pen-c | H | H | CN | H | 2 | |
| V-69 | $CF_3$ | H | H | Hex-c | H | H | CN | H | 2 | |
| V-70 | $CF_3$ | H | H | $CH_2$Pr-c | H | H | CN | H | 2 | 148-150 |
| V-71 | $CF_3$ | H | H | $CH_2$Bu-c | H | H | CN | H | 2 | |
| V-72 | $CF_3$ | H | H | $CH_2$Pen-c | H | H | CN | H | 2 | |
| V-73 | $CF_3$ | H | H | $CH_2$Hex-c | H | H | CN | H | 2 | |
| V-74 | $CF_3$ | Me | H | Et | H | H | CN | H | 0 | |
| V-75 | $CF_3$ | Me | H | Pr | H | H | CN | H | 0 | |
| V-76 | $CF_3$ | Me | H | Pr-i | H | H | CN | H | 0 | |
| V-77 | $CF_3$ | Me | H | Bu | H | H | CN | H | 0 | |
| V-78 | $CF_3$ | Me | H | Bu-i | H | H | CN | H | 0 | |
| V-79 | $CF_3$ | Me | H | Bu-s | H | H | CN | H | 0 | |
| V-80 | $CF_3$ | Me | H | Bu-t | H | H | CN | H | 0 | |
| V-81 | $CF_3$ | Me | H | $CH_2CH_2Cl$ | H | H | CN | H | 0 | |
| V-82 | $CF_3$ | Me | H | $CH_2CF_3$ | H | H | CN | H | 0 | 87-88 |
| V-83 | $CF_3$ | Me | H | $CH_2$Pr-c | H | H | CN | H | 0 | 105-107 |
| V-84 | $CF_3$ | Me | H | Et | H | H | CN | H | 1 | |
| V-85 | $CF_3$ | Me | H | Pr | H | H | CN | H | 1 | |
| V-86 | $CF_3$ | Me | H | Pr-i | H | H | CN | H | 1 | |
| V-87 | $CF_3$ | Me | H | Bu | H | H | CN | H | 1 | |

TABLE 30

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-88 | $CF_3$ | Me | H | Bu-i | H | H | CN | H | 1 | |
| V-89 | $CF_3$ | Me | H | Bu-s | H | H | CN | H | 1 | |
| V-90 | $CF_3$ | Me | H | Bu-t | H | H | CN | H | 1 | |
| V-91 | $CF_3$ | Me | H | $CH_2CH_2Cl$ | H | H | CN | H | 1 | |
| V-92 | $CF_3$ | Me | H | $CH_2CF_3$ | H | H | CN | H | 1 | 142-144 |
| V-93 | $CF_3$ | Me | H | $CH_2$Pr-c | H | H | CN | H | 1 | 125-126 |
| V-94 | $CF_3$ | Cl | H | Et | H | H | CN | H | 0 | |
| V-95 | $CF_3$ | Cl | H | Pr | H | H | CN | H | 0 | 90-91 |

TABLE 30-continued

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-96 | $CF_3$ | Cl | H | Pr-i | H | H | CN | H | 0 | |
| V-97 | $CF_3$ | Cl | H | Bu | H | H | CN | H | 0 | |
| V-98 | $CF_3$ | Cl | H | Bu-i | H | H | CN | H | 0 | |
| V-99 | $CF_3$ | Cl | H | Bu-s | H | H | CN | H | 0 | |
| V-100 | $CF_3$ | Cl | H | Bu-t | H | H | CN | H | 0 | |
| V-101 | $CF_3$ | Cl | H | $CH_2CH_2Cl$ | H | H | CN | H | 0 | |
| V-102 | $CF_3$ | Cl | H | $CH_2CF_3$ | H | H | CN | H | 0 | 73-75 |
| V-103 | $CF_3$ | Cl | H | $CH_2Pr$-c | H | H | CN | H | 0 | 129-130 |
| V-104 | $CF_3$ | Cl | H | Et | H | H | CN | H | 1 | |
| V-105 | $CF_3$ | Cl | H | Pr | H | H | CN | H | 1 | 144-146 |
| V-106 | $CF_3$ | Cl | H | Pr-i | H | H | CN | H | 1 | |
| V-107 | $CF_3$ | Cl | H | Bu | H | H | CN | H | 1 | |
| V-105 | $CF_3$ | Cl | H | Bu-i | H | H | CN | H | 1 | |
| V-109 | $CF_3$ | Cl | H | Bu-s | H | H | CN | H | 1 | |
| V-110 | $CF_3$ | Cl | H | Bu-t | H | H | CN | H | 1 | |
| V-111 | $CF_3$ | Cl | H | $CH_2CH_2Cl$ | H | H | CN | H | 1 | |
| V-112 | $CF_3$ | Cl | H | $CH_2CF_3$ | H | H | CN | H | 1 | |
| V-113 | $CF_3$ | Cl | H | $CH_2Pr$-c | H | H | CN | H | 1 | 128-131 |
| V-114 | $CF_3$ | Br | H | Pr | H | H | CN | H | 0 | 107-109 |
| V-115 | $CF_3$ | I | H | Pr | H | H | CN | H | 0 | |
| V-116 | $CF_3$ | Me | H | Pr | H | H | CN | H | 0 | 87-89 |
| V-117 | $CF_3$ | Br | H | Pr | H | H | CN | H | 1 | |
| V-118 | $CF_3$ | I | H | Pr | H | H | CN | H | 1 | |

TABLE 31

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-119 | $CF_3$ | $NH_2$ | H | Pr | H | H | CN | H | 1 | 153-155 |
| V-120 | $CF_3$ | Me | H | Pr | H | H | CN | H | 1 | 140-142 |
| V-121 | $CF_3$ | Br | H | $CH_2Pr$-c | H | H | CN | H | 0 | 138-139 |
| V-122 | $CF_3$ | I | H | $CH_2Pr$-c | H | H | CN | H | 0 | |
| V-123 | $CF_3$ | Me | H | $CH_2Pr$-c | H | H | CN | H | 0 | |
| V-124 | $CF_3$ | Br | H | $CH_2Pr$-c | H | H | CN | H | 1 | 158-159 |
| V-125 | $CF_3$ | I | H | $CH_2Pr$-c | H | H | CN | H | 1 | |
| V-126 | $CF_3$ | Me | H | $CH_2Pr$-c | H | H | CN | H | 1 | |
| V-127 | $CF_3$ | Br | H | $CH_2CF_3$ | H | H | CN | H | 0 | |
| V-128 | $CF_3$ | I | H | $CH_2CF_3$ | H | H | CN | H | 0 | |
| V-129 | $CF_3$ | $NH_2$ | H | $CH_2CF_3$ | H | H | CN | H | 0 | |
| V-130 | $CF_3$ | NHMe | H | $CH_2CF_3$ | H | H | CN | H | 0 | |
| V-131 | $CF_3$ | $N(Me)_2$ | H | $CH_2CF_3$ | H | H | CN | H | 0 | |
| V-132 | $CF_3$ | NHCOMe | H | $CH_2CF_3$ | H | H | CN | H | 0 | |
| V-133 | $CF_3$ | $NHCO_2Me$ | H | $CH_2CF_3$ | H | H | CN | H | 0 | |
| V-134 | $CF_3$ | $NHCO_2Bu$-t | H | $CH_2CF_3$ | H | H | CN | H | 0 | |
| V-135 | $CF_3$ | Me | H | $CH_2CF_3$ | H | H | CN | H | 0 | |
| V-136 | $CF_3$ | Br | H | $CH_2CF_3$ | H | H | CN | H | 1 | |
| V-137 | $CF_3$ | I | H | $CH_2CF_3$ | H | H | CN | H | 1 | |
| V-138 | $CF_3$ | $NH_2$ | H | $CH_2CF_3$ | H | H | CN | H | 1 | |
| V-139 | $CF_3$ | NHMe | H | $CH_2CF_3$ | H | H | CN | H | 1 | |
| V-140 | $CF_3$ | $N(Me)_2$ | H | $CH_2CF_3$ | H | H | CN | H | 1 | |
| V-141 | $CF_3$ | NHCOMe | H | $CH_2CF_3$ | H | H | CN | H | 1 | |
| V-142 | $CF_3$ | $NHCO_2Me$ | H | $CH_2CF_3$ | H | H | CN | H | 1 | |
| V-143 | $CF_3$ | $NHCO_2Bu$-t | H | $CH_2CF_3$ | H | H | CN | H | 1 | |
| V-144 | $CF_3$ | Me | H | $CH_2CF_3$ | H | H | CN | H | 1 | |
| V-145 | $CF_3$ | H | $CF_3$ | Pr | H | H | CN | H | 0 | 1.5161 |
| V-146 | $CF_3$ | H | $CF_3$ | Pr | H | H | CN | H | 1 | 1.5070 |
| V-147 | $CF_3$ | H | $CF_3$ | $CH_2Pr$-c | H | H | CN | H | 0 | 1.5252 |
| V-148 | $CF_3$ | H | $CF_3$ | $CH_2Pr$-c | H | H | CN | H | 1 | 1.5148 |
| V-149 | $CF_3$ | H | $CF_3$ | $CH_2CF_3$ | H | H | CN | H | 0 | |

TABLE 32

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-150 | $CF_3$ | H | OMe | $CH_2CF_3$ | H | H | CN | H | 0 | |
| V-151 | $CF_3$ | H | $CF_3$ | $CH_2CF_3$ | H | H | CN | H | 1 | |
| V-152 | $CF_3$ | H | OMe | $CH_2CF_3$ | H | H | CN | H | 1 | |
| V-153 | H | H | $CF_3$ | Pr | H | H | CN | H | 0 | 1.5562 |
| V-154 | H | H | $CF_3$ | Pr | H | H | CN | H | 1 | 57-58 |
| V-155 | H | H | $CF_3$ | $CH_3$Pr-c | H | H | CN | H | 0 | 1.5691 |
| V-156 | H | H | $CF_3$ | $CH_2$Pr-c | H | H | CN | H | 1 | 94-95 |
| V-157 | H | H | $CF_3$ | $CH_2CF_3$ | H | H | CN | H | 0 | |
| V-158 | H | H | $CF_3$ | $CH_2CF_3$ | H | H | CN | H | 1 | |
| V-159 | $CF_3$ | H | H | Pr | H | H | CHO | H | 0 | 59-60 |
| V-160 | $CF_3$ | H | H | Pr | H | H | $CH_2OH$ | H | 0 | |
| V-161 | $CF_3$ | H | H | Pr | H | H | $CH_2OMe$ | H | 0 | |
| V-162 | $CF_3$ | H | H | Pr | H | H | $CH=CH_2$ | H | 0 | |
| V-163 | $CF_3$ | H | H | Pr | H | H | $CHBrCHBr_2$ | H | 0 | |
| V-164 | $CF_3$ | H | H | Pr | H | H | C≡CH | H | 0 | |
| V-165 | $CF_3$ | H | H | Pr | H | H | $CH_2Cl$ | H | 0 | |
| V-166 | $CF_3$ | H | H | Pr | H | H | $NO_2$ | H | 0 | 1.5741 |
| V-167 | $CF_3$ | H | H | Pr | H | H | $NH_2$ | H | 0 | 1.5639 |
| V-168 | $CF_3$ | H | H | Pr | H | H | NHMe | H | 0 | |
| V-169 | $CF_3$ | H | H | Pr | H | H | $N(Me)_2$ | H | 0 | |
| V-170 | $CF_3$ | H | H | Pr | H | H | NHCOMe | H | 0 | |
| V-171 | $CF_3$ | H | H | Pr | H | H | NHCOBu-t | H | 0 | |
| V-172 | $CF_3$ | H | H | Pr | H | H | $NHCO_2Me$ | H | 0 | |
| V-173 | $CF_3$ | H | H | Pr | H | H | $NHCO_2$Bu-t | H | 0 | 95-97 |
| V-174 | $CF_3$ | H | H | Pr | H | H | $CO_2H$ | H | 0 | 156-158 |
| V-175 | $CF_3$ | H | H | Pr | H | H | $CO_2Me$ | H | 0 | 114-116 |
| V-176 | $CF_3$ | H | H | Pr | H | H | Me | H | 0 | Unmeasurable |
| V-177 | $CF_3$ | H | H | Pr | H | H | Et | H | 0 | |
| V-178 | $CF_3$ | H | H | Pr | H | H | $CH_2F$ | H | 0 | |
| V-179 | $CF_3$ | H | H | Pr | H | H | $CHF_2$ | H | 0 | 1.5259 |
| V-180 | $CF_3$ | H | H | Pr | H | H | $CF_3$ | H | 0 | |

TABLE 33

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-181 | $CF_3$ | H | H | Pr | H | H | CH=NOH | H | 0 | |
| V-182 | $CF_3$ | H | H | Pr | H | H | CH=NOMe | H | 0 | |
| V-183 | $CF_3$ | H | H | Pr | H | H | CH(OH)Me | H | 0 | |
| V-184 | $CF_3$ | H | H | Pr | H | H | COMe | H | 0 | |
| V-185 | $CF_3$ | H | H | Pr | H | H | Cl | H | 0 | |
| V-186 | $CF_3$ | H | H | Pr | H | H | Br | H | 0 | |
| V-187 | $CF_3$ | H | H | Pr | H | H | I | H | 0 | |
| V-188 | $CF_3$ | H | H | Pr | H | H | CHO | H | 1 | 99-100 |
| V-189 | $CF_3$ | H | H | Pr | H | H | $CH_2OH$ | H | 1 | |
| V-190 | $CF_3$ | H | H | Pr | H | H | $CH_2OMe$ | H | 1 | |
| V-191 | $CF_3$ | H | H | Pr | H | H | $CH=CH_2$ | H | 1 | |
| V-192 | $CF_3$ | H | H | Pr | H | H | $CHBrCHBr_2$ | H | 1 | |
| V-193 | $CF_3$ | H | H | Pr | H | H | C≡CH | H | 1 | |
| V-194 | $CF_3$ | H | H | Pr | H | H | $CH_2Cl$ | H | 1 | |
| V-195 | $CF_3$ | H | H | Pr | H | H | $NO_2$ | H | 1 | 93-95 |
| V-196 | $CF_3$ | H | H | Pr | H | H | $NH_2$ | H | 1 | 1.5491 |
| V-197 | $CF_3$ | H | H | Pr | H | H | NHMe | H | 1 | |
| V-198 | $CF_3$ | H | H | Pr | H | H | $N(Me)_2$ | H | 1 | |
| V-199 | $CF_3$ | H | H | Pr | H | H | NHCOMe | H | 1 | |
| V-200 | $CF_3$ | H | H | Pr | H | H | NHCOBu-t | H | 1 | |
| V-201 | $CF_3$ | H | H | Pr | H | H | $NHCO_2Me$ | H | 1 | |
| V-202 | $CF_3$ | H | H | Pr | H | H | $NHCO_2$Bu-t | H | 1 | |
| V-203 | $CF_3$ | H | H | Pr | H | H | $CO_2H$ | H | 1 | |
| V-204 | $CF_3$ | H | H | Pr | H | H | $CO_2Me$ | H | 1 | 132-133 |
| V-205 | $CF_3$ | H | H | Pr | H | H | Me | H | 1 | |
| V-206 | $CF_3$ | H | H | Pr | H | H | Et | H | 1 | |
| V-207 | $CF_3$ | H | H | Pr | H | H | $CH_2F$ | H | 1 | |
| V-208 | $CF_3$ | H | H | Pr | H | H | $CHF_2$ | H | 1 | 1.5138 |
| V-209 | $CF_3$ | H | H | Pr | H | H | $CF_3$ | H | 1 | |
| V-210 | $CF_3$ | H | H | Pr | H | H | CH=NOH | H | 1 | |
| V-211 | $CF_3$ | H | H | Pr | H | H | CH=NOMe | H | 1 | |

TABLE 34

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-212 | $CF_3$ | H | H | Pr | H | H | CH(OH)Me | H | 1 | |
| V-213 | $CF_3$ | H | H | Pr | H | H | COMe | H | 1 | |
| V-214 | $CF_3$ | H | H | Pr | H | H | Cl | H | 1 | |
| V-215 | $CF_3$ | H | H | Pr | H | H | Br | H | 1 | |
| V-216 | $CF_3$ | H | H | Pr | H | H | I | H | 1 | |
| V-217 | $CF_3$ | H | H | $CH_2$Pr-c | H | H | CHO | H | 0 | |
| V-218 | $CF_3$ | H | H | $CH_2$Pr-c | H | H | $CH_2OH$ | H | 0 | |
| V-219 | $CF_3$ | H | H | $CH_2$Pr-c | H | H | $CH_2OMe$ | H | 0 | |
| V-220 | $CF_3$ | H | H | $CH_2$Pr-c | H | H | $CH=CH_2$ | H | 0 | |
| V-221 | $CF_3$ | H | H | $CH_2$Pr-c | H | H | $CHBrCHBr_2$ | H | 0 | |
| V-222 | $CF_3$ | H | H | $CH_2$Pr-c | H | H | C≡CH | H | 0 | |
| V-223 | $CF_3$ | H | H | $CH_2$Pr-c | H | H | $CH_2Cl$ | H | 0 | |
| V-224 | $CF_3$ | H | H | $CH_2$Pr-c | H | H | $NO_2$ | H | 0 | 1.5518 |
| V-225 | $CF_3$ | H | H | $CH_2$Pr-c | H | H | $NH_2$ | H | 0 | |
| V-226 | $CF_3$ | H | H | $CH_2$Pr-c | H | H | NHMe | H | 0 | |
| V-227 | $CF_3$ | H | H | $CH_2$Pr-c | H | H | $N(Me)_2$ | H | 0 | |
| V-228 | $CF_3$ | H | H | $CH_2$Pr-c | H | H | NHCOMe | H | 0 | |
| V-229 | $CF_3$ | H | H | $CH_2$Pr-c | H | H | NHCOBu-t | H | 0 | |
| V-230 | $CF_3$ | H | H | $CH_2$Pr-c | H | H | $NHCO_2Me$ | H | 0 | |
| V-231 | $CF_3$ | H | H | $CH_2$Pr-c | H | H | $NHCO_2Bu$-t | H | 0 | |
| V-232 | H | H | H | $CH_2$Pr-c | H | H | $CO_2H$ | H | 0 | |
| V-233 | H | H | H | $CH_2$Pr-c | H | H | $CO_2Me$ | H | 0 | |
| V-234 | H | H | H | $CH_2$Pr-c | H | H | Me | H | 0 | |
| V-235 | H | H | H | $CH_2$Pr-c | H | H | Et | H | 0 | |
| V-236 | H | H | H | $CH_2$Pr-c | H | H | $CH_2F$ | H | 0 | |
| V-237 | $CF_3$ | H | H | $CH_2$Pr-c | H | H | $CHF_2$ | H | 0 | 1.5245 |
| V-238 | $CF_3$ | H | H | $CH_2$Pr-c | H | H | $CF_3$ | H | 0 | |
| V-239 | $CF_3$ | H | H | $CH_2$Pr-c | H | H | CH=NOH | H | 0 | |
| V-240 | $CF_3$ | H | H | $CH_2$Pr-c | H | H | CH=NOMe | H | 0 | |
| V-241 | $CF_3$ | H | H | $CH_2$Pr-c | H | H | CH(OH)Me | H | 0 | |
| V-242 | $CF_3$ | H | H | $CH_2$Pr-c | H | H | COMe | H | 0 | |

TABLE 35

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-243 | $CF_3$ | H | H | $CH_2$Pr-c | H | H | Cl | H | 0 | |
| V-244 | $CF_3$ | H | H | $CH_2$Pr-c | H | H | Br | H | 0 | |
| V-245 | $CF_3$ | H | H | $CH_2$Pr-c | H | H | I | H | 0 | |
| V-246 | $CF_3$ | H | H | $CH_2$Pr-c | H | H | CHO | H | 1 | |
| V-247 | $CF_3$ | H | H | $CH_2$Pr-c | H | H | $CH_2OH$ | H | 1 | |
| V-248 | $CF_3$ | H | H | $CH_2$Pr-c | H | H | $CH_2OMe$ | H | 1 | |
| V-249 | $CF_3$ | H | H | $CH_2$Pr-c | H | H | $CH=CH_2$ | H | 1 | |
| V-250 | $CF_3$ | H | H | $CH_2$Pr-c | H | H | $CHBrCHBr_2$ | H | 1 | |
| V-251 | $CF_3$ | H | H | $CH_2$Pr-c | H | H | C≡CH | H | 1 | |
| V-252 | $CF_3$ | H | H | $CH_2$Pr-c | H | H | $CH_2Cl$ | H | 1 | |
| V-253 | $CF_3$ | H | H | $CH_2$Pr-c | H | H | $NO_2$ | H | 1 | 59-61 |
| V-254 | $CF_3$ | H | H | $CH_2$Pr-c | H | H | $NH_2$ | H | 1 | |
| V-255 | $CF_3$ | H | H | $CH_2$Pr-c | H | H | NHMe | H | 1 | |
| V-256 | $CF_3$ | H | H | $CH_2$Pr-c | H | H | $N(Me)_2$ | H | 1 | |
| V-257 | $CF_3$ | H | H | $CH_2$Pr-c | H | H | NHCOMe | H | 1 | |
| V-258 | $CF_3$ | H | H | $CH_2$Pr-c | H | H | NHCOBu-t | H | 1 | |
| V-259 | $CF_3$ | H | H | $CH_2$Pr-c | H | H | $NHCO_2Me$ | H | 1 | |
| V-260 | $CF_3$ | H | H | $CH_2$Pr-c | H | H | $NHCO_2Bu$-t | H | 1 | |
| V-261 | $CF_3$ | H | H | $CH_2$Pr-c | H | H | $CO_2H$ | H | 1 | |
| V-262 | $CF_3$ | H | H | $CH_2$Pr-c | H | H | $CO_2Me$ | H | 1 | |
| V-263 | $CF_3$ | H | H | $CH_2$Pr-c | H | H | Me | H | 1 | |
| V-264 | $CF_3$ | H | H | $CH_2$Pr-c | H | H | Et | H | 1 | |
| V-265 | $CF_3$ | H | H | $CH_2$Pr-c | H | H | $CH_2F$ | H | 1 | |
| V-266 | $CF_3$ | H | H | $CH_2$Pr-c | H | H | $CHF_2$ | H | 1 | 1.5189 |
| V-267 | $CF_3$ | H | H | $CH_2$Pr-c | H | H | $CF_3$ | H | 1 | |
| V-268 | $CF_3$ | H | H | $CH_2$Pr-c | H | H | CH=NOH | H | 1 | |
| V-269 | $CF_3$ | H | H | $CH_2$Pr-c | H | H | CH=NOMe | H | 1 | |
| V-270 | $CF_3$ | H | H | $CH_2$Pr-c | H | H | CH(OH)Me | H | 1 | |
| V-271 | $CF_3$ | H | H | $CH_2$Pr-c | H | H | COMe | H | 1 | |
| V-272 | $CF_3$ | H | H | $CH_2$Pr-c | H | H | Cl | H | 1 | |
| V-273 | $CF_3$ | H | H | $CH_2$Pr-c | H | H | Br | H | 1 | |

TABLE 36

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-274 | $CF_3$ | H | H | $CH_2$Pr-c | H | H | I | H | 1 | |
| V-275 | $CF_3$ | H | H | $CH_2CF_3$ | H | H | CHO | H | 0 | 113-114 |
| V-276 | $CF_3$ | H | H | $CH_2CF_3$ | H | H | $CH_2OH$ | H | 0 | 68-70 |
| V-277 | $CF_3$ | H | H | $CH_2CF_3$ | H | H | $CH_2OMe$ | H | 0 | |
| V-278 | $CF_3$ | H | H | $CH_2CF_3$ | H | H | $CH=CH_2$ | H | 0 | 1.5328 |
| V-279 | $CF_3$ | H | H | $CH_2CF_3$ | H | H | $CHBrCHBr_2$ | H | 0 | |
| V-280 | $CF_3$ | H | H | $CH_2CF_3$ | H | H | C≡CH | H | 0 | Unmeasurable |
| V-281 | $CF_3$ | H | H | $CH_2CF_3$ | H | H | $CH_2Cl$ | H | 0 | |
| V-282 | $CF_3$ | H | H | $CH_2CF_3$ | H | H | $NO_2$ | H | 0 | |
| V-283 | $CF_3$ | H | H | $CH_2CF_3$ | H | H | $NH_2$ | H | 0 | 1.5205 |
| V-284 | $CF_3$ | H | H | $CH_2CF_3$ | H | H | NHMe | H | 0 | 1.5215 |
| V-285 | $CF_3$ | H | H | $CH_2CF_3$ | H | H | $N(Me)_2$ | H | 0 | 1.5056 |
| V-286 | $CF_3$ | H | H | $CH_2CF_3$ | H | H | NHCOMe | H | 0 | 79-80 |
| V-287 | $CF_3$ | H | H | $CH_2CF_3$ | H | H | NHCOBu-t | H | 0 | |
| V-288 | $CF_3$ | H | H | $CH_2CF_3$ | H | H | $NHCO_2Me$ | H | 0 | |
| V-289 | $CF_3$ | H | H | $CH_2CF_3$ | H | H | $NHCO_2Bu$-t | H | 0 | |
| V-290 | $CF_3$ | H | H | $CH_2CF_3$ | H | H | $CO_2H$ | H | 0 | |
| V-291 | $CF_3$ | H | H | $CH_2CF_3$ | H | H | $CO_2Me$ | H | 0 | |
| V-292 | $CF_3$ | H | H | $CH_2CF_3$ | H | H | Me | H | 0 | 1.5052 |
| V-293 | $CF_3$ | H | H | $CH_2CF_3$ | H | H | Et | H | 0 | |
| V-294 | $CF_3$ | H | H | $CH_2CF_3$ | H | H | $CH_2F$ | H | 0 | Unmeasurable |
| V-295 | $CF_3$ | H | H | $CH_2CF_3$ | H | H | $CHF_2$ | H | 0 | 1.4951 |
| V-296 | $CF_3$ | H | H | $CH_2CF_3$ | H | H | $CF_3$ | H | 0 | |
| V-297 | $CF_3$ | H | H | $CH_2CF_3$ | H | H | CH=NOH | H | 0 | 96-97 |
| V-298 | $CF_3$ | H | H | $CH_2CF_3$ | H | H | CH=NOMe | H | 0 | |
| V-299 | $CF_3$ | H | H | $CH_2CF_3$ | H | H | CH(OH)Me | H | 0 | |
| V-300 | $CF_3$ | H | H | $CH_2CF_3$ | H | H | COMe | H | 0 | |
| V-301 | $CF_3$ | H | H | $CH_2CF_3$ | H | H | Cl | H | 0 | 1.4981 |
| V-302 | $CF_3$ | H | H | $CH_2CF_3$ | H | H | Br | H | 0 | 1.5221 |
| V-303 | $CF_3$ | H | H | $CH_2CF_3$ | H | H | I | H | 0 | |
| V-304 | $CF_3$ | H | H | $CH_2CF_3$ | H | H | CHO | H | 1 | 198-200 |

TABLE 37

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-305 | $CF_3$ | H | H | $CH_2CF_3$ | H | H | $CH_2OH$ | H | 1 | 151-154 |
| V-306 | $CF_3$ | H | H | $CH_2CF_3$ | H | H | $CH_2OMe$ | H | 1 | |
| V-307 | $CF_3$ | H | H | $CH_2CF_3$ | H | H | $CH=CH_2$ | H | 1 | 89-90 |
| V-308 | $CF_3$ | H | H | $CH_2CF_3$ | H | H | $CHBrCHBr_2$ | H | 1 | |
| V-309 | $CF_3$ | H | H | $CH_2CF_3$ | H | H | C≡CH | H | 1 | 96-99 |
| V-310 | $CF_3$ | H | H | $CH_2CF_3$ | H | H | $CH_2Cl$ | H | 1 | |
| V-311 | $CF_3$ | H | H | $CH_2CF_3$ | H | H | $NO_2$ | H | 1 | |
| V-312 | $CF_3$ | H | H | $CH_2CF_3$ | H | H | $NH_2$ | H | 1 | 132-133 |
| V-313 | $CF_3$ | H | H | $CH_2CF_3$ | H | H | NHMe | H | 1 | |
| V-314 | $CF_3$ | H | H | $CH_2CF_3$ | H | H | $N(Me)_2$ | H | 1 | |
| V-315 | $CF_3$ | H | H | $CH_2CF_3$ | H | H | NHCOMe | H | 1 | |
| V-316 | $CF_3$ | H | H | $CH_2CF_3$ | H | H | NHCOBu-t | H | 1 | |
| V-317 | $CF_3$ | H | H | $CH_2CF_3$ | H | H | $NHCO_2Me$ | H | 1 | |
| V-318 | $CF_3$ | H | H | $CH_2CF_3$ | H | H | $NHCO_2Bu$-t | H | 1 | |
| V-319 | $CF_3$ | H | H | $CH_2CF_3$ | H | H | $CO_2H$ | H | 1 | |
| V-320 | $CF_3$ | H | H | $CH_2CF_3$ | H | H | $CO_2Me$ | H | 1 | |
| V-321 | $CF_3$ | H | H | $CH_2CF_3$ | H | H | Me | H | 1 | 109-110 |
| V-322 | $CF_3$ | H | H | $CH_2CF_3$ | H | H | Et | H | 1 | |
| V-323 | $CF_3$ | H | H | $CH_2CF_3$ | H | H | $CH_2F$ | H | 1 | 117-119 |
| V-324 | $CF_3$ | H | H | $CH_2CF_3$ | H | H | $CHF_2$ | H | 1 | 1.4909 |
| V-325 | $CF_3$ | H | H | $CH_2CF_3$ | H | H | $CF_3$ | H | 1 | |
| V-326 | $CF_3$ | H | H | $CH_2CF_3$ | H | H | CH=NOH | H | 1 | 191-192 |
| V-327 | $CF_3$ | H | H | $CH_2CF_3$ | H | H | CH=NOMe | H | 1 | |
| V-328 | $CF_3$ | H | H | $CH_2CF_3$ | H | H | CH(OH)Me | H | 1 | |
| V-329 | $CF_3$ | H | H | $CH_2CF_3$ | H | H | COMe | H | 1 | |
| V-330 | $CF_3$ | H | H | $CH_2CF_3$ | H | H | Cl | H | 1 | 97-98 |
| V-331 | $CF_3$ | H | H | $CH_2CF_3$ | H | H | Br | H | 1 | Unmeasurable |
| V-332 | $CF_3$ | H | H | $CH_2CF_3$ | H | H | I | H | 1 | |
| V-333 | $CF_3$ | Me | H | Pr | H | H | Me | H | 0 | 1.5292 |
| V-334 | $CF_3$ | Cl | H | Pr | H | H | Me | H | 0 | |
| V-335 | $CF_3$ | Br | H | Pr | H | H | Me | H | 0 | |

TABLE 38

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-336 | $CF_3$ | $NH_2$ | H | Pr | H | H | Me | H | 0 | |
| V-337 | $CF_3$ | NHMe | H | Pr | H | H | Me | H | 0 | |
| V-338 | $CF_3$ | $N(Me)_2$ | H | Pr | H | H | Me | H | 0 | |
| V-339 | $CF_3$ | NHCOMe | H | Pr | H | H | Me | H | 0 | |
| V-340 | $CF_3$ | $NHCO_2Me$ | H | Pr | H | H | Me | H | 0 | |
| V-341 | $CF_3$ | Me | H | Pr | H | H | Me | H | 1 | 1.5460 |
| V-342 | $CF_3$ | Cl | H | Pr | H | H | Me | H | 1 | |
| V-343 | $CF_3$ | Br | H | Pr | H | H | Me | H | 1 | |
| V-344 | $CF_3$ | $NH_2$ | H | Pr | H | H | Me | H | 1 | |
| V-345 | $CF_3$ | NHMe | H | Pr | H | H | Me | H | 1 | |
| V-346 | $CF_3$ | $N(Me)_2$ | H | Pr | H | H | Me | H | 1 | |
| V-347 | $CF_3$ | NHCOMe | H | Pr | H | H | Me | H | 1 | |
| V-348 | $CF_3$ | $NHCO_2Me$ | H | Pr | H | H | Me | H | 1 | |
| V-349 | $CF_3$ | Me | H | $CH_2Pr$-c | H | H | Me | H | 0 | |
| V-350 | $CF_3$ | Cl | H | $CH_2Pr$-c | H | H | Me | H | 0 | |
| V-351 | $CF_3$ | Br | H | $CH_2Pr$-c | H | H | Me | H | 0 | |
| V-352 | $CF_3$ | $NH_2$ | H | $CH_2Pr$-c | H | H | Me | H | 0 | |
| V-353 | $CF_3$ | NHMe | H | $CH_2Pr$-c | H | H | Me | H | 0 | |
| V-354 | $CF_3$ | $N(Me)_2$ | H | $CH_2Pr$-c | H | H | Me | H | 0 | |
| V-355 | $CF_3$ | NHCOMe | H | $CH_2Pr$-c | H | H | Me | H | 0 | |
| V-356 | $CF_3$ | $NHCO_2Me$ | H | $CH_2Pr$-c | H | H | Me | H | 0 | |
| V-357 | $CF_3$ | Me | H | $CH_2Pr$-c | H | H | Me | H | 1 | |
| V-358 | $CF_3$ | Cl | H | $CH_2Pr$-c | H | H | Me | H | 1 | |
| V-359 | $CF_3$ | Br | H | $CH_2Pr$-c | H | H | Me | H | 1 | |
| V-360 | $CF_3$ | $NH_2$ | H | $CH_2Pr$-c | H | H | Me | H | 1 | |
| V-361 | $CF_3$ | NHMe | H | $CH_2Pr$-c | H | H | Me | H | 1 | |
| V-362 | $CF_3$ | $N(Me)_2$ | H | $CH_2Pr$-c | H | H | Me | H | 1 | |
| V-363 | $CF_3$ | NHCOMe | H | $CH_2Pr$-c | H | H | Me | H | 1 | |
| V-364 | $CF_3$ | $NHCO_2Me$ | H | $CH_2Pr$-c | H | H | Me | H | 1 | |
| V-365 | $CF_3$ | Me | H | $CH_2CF_3$ | H | H | Me | H | 0 | 1.5090 |
| V-366 | $CF_3$ | Cl | H | $CH_2CF_3$ | H | H | Me | H | 0 | 50-52 |

TABLE 39

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-367 | $CF_3$ | Br | H | $CH_2CF_3$ | H | H | Me | H | 0 | |
| V-368 | $CF_3$ | $NH_2$ | H | $CH_2CF_3$ | H | H | Me | H | 0 | |
| V-369 | $CF_3$ | NHMe | H | $CH_2CF_3$ | H | H | Me | H | 0 | |
| V-370 | $CF_3$ | $N(Me)_2$ | H | $CH_2CF_3$ | H | H | Me | H | 0 | |
| V-371 | $CF_3$ | NHCOMe | H | $CH_2CF_3$ | H | H | Me | H | 0 | |
| V-372 | $CF_3$ | $NHCO_2Me$ | H | $CH_2CF_3$ | H | H | Me | H | 0 | |
| V-373 | $CF_3$ | Me | H | $CH_2CF_3$ | H | H | Me | H | 1 | 107-108 |
| V-374 | $CF_3$ | Cl | H | $CH_2CF_3$ | H | H | Me | H | 1 | |
| V-375 | $CF_3$ | Br | H | $CH_2CF_3$ | H | H | Me | H | 1 | |
| V-376 | $CF_3$ | $NH_2$ | H | $CH_2CF_3$ | H | H | Me | H | 1 | |
| V-377 | $CF_3$ | NHMe | H | $CH_2CF_3$ | H | H | Me | H | 1 | |
| V-378 | $CF_3$ | $N(Me)_2$ | H | $CH_2CF_3$ | H | H | Me | H | 1 | |
| V-379 | $CF_3$ | NHCOMe | H | $CH_2CF_3$ | H | H | Me | H | 1 | |
| V-380 | $CF_3$ | $NHCO_2Me$ | H | $CH_2CF_3$ | H | H | Me | H | 1 | |
| V-381 | $CF_3$ | Me | H | Pr | H | H | CHO | H | 0 | 1.5726 |
| V-382 | $CF_3$ | Me | H | Pr | H | H | $CH_2OH$ | H | 0 | |
| V-383 | $CF_3$ | Me | H | Pr | H | H | $CH_2OMe$ | H | 0 | |
| V-384 | $CF_3$ | Me | H | Pr | H | H | $CH=CH_2$ | H | 0 | |
| V-385 | $CF_3$ | Me | H | Pr | H | H | $CHBrCHBr_2$ | H | 0 | |
| V-386 | $CF_3$ | Me | H | Pr | H | H | C≡CH | H | 0 | |
| V-387 | $CF_3$ | Me | H | Pr | H | H | $CH_2Cl$ | H | 0 | |
| V-388 | $CF_3$ | Me | H | Pr | H | H | $NO_2$ | H | 0 | |
| V-389 | $CF_3$ | Me | H | Pr | H | H | $NH_2$ | H | 0 | |
| V-390 | $CF_3$ | Me | H | Pr | H | H | NHMe | H | 0 | |
| V-391 | $CF_3$ | Me | H | Pr | H | H | $N(Me)_2$ | H | 0 | |
| V-392 | $CF_3$ | Me | H | Pr | H | H | NHCOMe | H | 0 | |
| V-393 | $CF_3$ | Me | H | Pr | H | H | NHCOBu-t | H | 0 | |
| V-394 | $CF_3$ | Me | H | Pr | H | H | $NHCO_2Me$ | H | 0 | |
| V-395 | $CF_3$ | Me | H | Pr | H | H | $NHCO_2Bu$-t | H | 0 | |
| V-396 | $CF_3$ | Me | H | Pr | H | H | $CO_2H$ | H | 0 | |
| V-397 | $CF_3$ | Me | H | Pr | H | H | $CO_2Me$ | H | 0 | |

TABLE 40

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-398 | $CF_3$ | Me | H | Pr | H | H | Et | H | 0 | |
| V-399 | $CF_3$ | Me | H | Pr | H | H | $CH_2F$ | H | 0 | |
| V-400 | $CF_3$ | Me | H | Pr | H | H | $CHF_2$ | H | 0 | |
| V-401 | $CF_3$ | Me | H | Pr | H | H | $CF_3$ | H | 0 | |
| V-402 | $CF_3$ | Me | H | Pr | H | H | CH=NOH | H | 0 | |
| V-403 | $CF_3$ | Me | H | Pr | H | H | CH=NOMe | H | 0 | |
| V-404 | $CF_3$ | Me | H | Pr | H | H | CH(OH)Me | H | 0 | |
| V-405 | $CF_3$ | Me | H | Pr | H | H | COMe | H | 0 | |
| V-406 | $CF_3$ | Me | H | Pr | H | H | Cl | H | 0 | |
| V-407 | $CF_3$ | Me | H | Pr | H | H | Br | H | 0 | |
| V-408 | $CF_3$ | Me | H | Pr | H | H | I | H | 0 | |
| V-409 | $CF_3$ | Me | H | Pr | H | H | CHO | H | 1 | |
| V-410 | $CF_3$ | Me | H | Pr | H | H | $CH_2OH$ | H | 1 | |
| V-411 | $CF_3$ | Me | H | Pr | H | H | $CH_2OMe$ | H | 1 | |
| V-412 | $CF_3$ | Me | H | Pr | H | H | $CH=CH_2$ | H | 1 | |
| V-413 | $CF_3$ | Me | H | Pr | H | H | $CHBrCHBr_2$ | H | 1 | |
| V-414 | $CF_3$ | Me | H | Pr | H | H | C≡CH | H | 1 | |
| V-415 | $CF_3$ | Me | H | Pr | H | H | $CH_2Cl$ | H | 1 | |
| V-416 | $CF_3$ | Me | H | Pr | H | H | $NO_2$ | H | 1 | |
| V-417 | $CF_3$ | Me | H | Pr | H | H | $NH_2$ | H | 1 | |
| V-418 | $CF_3$ | Me | H | Pr | H | H | NHMe | H | 1 | |
| V-419 | $CF_3$ | Me | H | Pr | H | H | $N(Me)_2$ | H | 1 | |
| V-420 | $CF_3$ | Me | H | Pr | H | H | NHCOMe | H | 1 | |
| V-421 | $CF_3$ | Me | H | Pr | H | H | NHCOBu-t | H | 1 | |
| V-422 | $CF_3$ | Me | H | Pr | H | H | $NHCO_2Me$ | H | 1 | |
| V-423 | $CF_3$ | Me | H | Pr | H | H | $NHCO_2Bu-t$ | H | 1 | |
| V-424 | $CF_3$ | Me | H | Pr | H | H | $CO_2H$ | H | 1 | |
| V-425 | $CF_3$ | Me | H | Pr | H | H | $CO_2Me$ | H | 1 | |
| V-426 | $CF_3$ | Me | H | Pr | H | H | Et | H | 1 | |
| V-427 | $CF_3$ | Me | H | Pr | H | H | $CH_2F$ | H | 1 | |
| V-428 | $CF_3$ | Me | H | Pr | H | H | $CHF_2$ | H | 1 | |

TABLE 41

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-429 | $CF_3$ | Me | H | Pr | H | H | $CF_3$ | H | 1 | |
| V-430 | $CF_3$ | Me | H | Pr | H | H | CH=NOH | H | 1 | |
| V-431 | $CF_3$ | Me | H | Pr | H | H | CH=NOMe | H | 1 | |
| V-432 | $CF_3$ | Me | H | Pr | H | H | CH(OH)Me | H | 1 | |
| V-433 | $CF_3$ | Me | H | Pr | H | H | COMe | H | 1 | |
| V-434 | $CF_3$ | Me | H | Pr | H | H | Cl | H | 1 | |
| V-435 | $CF_3$ | Me | H | Pr | H | H | Br | H | 1 | |
| V-436 | $CF_3$ | Me | H | Pr | H | H | I | H | 1 | |
| V-437 | $CF_3$ | Me | H | $CH_2Pr-c$ | H | H | CHO | H | 0 | |
| V-438 | $CF_3$ | Me | H | $CH_2Pr-c$ | H | H | $CH_2OH$ | H | 0 | |
| V-439 | $CF_3$ | Me | H | $CH_2Pr-c$ | H | H | $CH_2OMe$ | H | 0 | |
| V-440 | $CF_3$ | Me | H | $CH_2Pr-c$ | H | H | $CH=CH_2$ | H | 0 | |
| V-441 | $CF_3$ | Me | H | $CH_2Pr-c$ | H | H | $CHBrCHBr_2$ | H | 0 | |
| V-442 | $CF_3$ | Me | H | $CH_2Pr-c$ | H | H | C≡CH | H | 0 | |
| V-443 | $CF_3$ | Me | H | $CH_2Pr-c$ | H | H | $CH_2Cl$ | H | 0 | |
| V-444 | $CF_3$ | Me | H | $CH_2Pr-c$ | H | H | $NO_2$ | H | 0 | |
| V-445 | $CF_3$ | Me | H | $CH_2Pr-c$ | H | H | $NH_2$ | H | 0 | |
| V-446 | $CF_3$ | Me | H | $CH_2Pr-c$ | H | H | NHMe | H | 0 | |
| V-447 | $CF_3$ | Me | H | $CH_2Pr-c$ | H | H | $N(Me)_2$ | H | 0 | |
| V-448 | $CF_3$ | Me | H | $CH_2Pr-c$ | H | H | NHCOMe | H | 0 | |
| V-449 | $CF_3$ | Me | H | $CH_2Pr-c$ | H | H | NHCOBu-t | H | 0 | |
| V-450 | $CF_3$ | Me | H | $CH_2Pr-c$ | H | H | $NHCO_2Me$ | H | 0 | |
| V-451 | $CF_3$ | Me | H | $CH_2Pr-c$ | H | H | $NHCO_2Bu-t$ | H | 0 | |
| V-452 | $CF_3$ | Me | H | $CH_2Pr-c$ | H | H | $CO_2H$ | H | 0 | |
| V-453 | $CF_3$ | Me | H | $CH_2Pr-c$ | H | H | $CO_2Me$ | H | 0 | |
| V-454 | $CF_3$ | Me | H | $CH_2Pr-c$ | H | H | Et | H | 0 | |
| V-455 | $CF_3$ | Me | H | $CH_2Pr-c$ | H | H | $CH_2F$ | H | 0 | |
| V-456 | $CF_3$ | Me | H | $CH_2Pr-c$ | H | H | $CHF_2$ | H | 0 | |
| V-457 | $CF_3$ | Me | H | $CH_2Pr-c$ | H | H | $CF_3$ | H | 0 | |
| V-458 | $CF_3$ | Me | H | $CH_2Pr-c$ | H | H | CH=NOH | H | 0 | |
| V-459 | $CF_3$ | Me | H | $CH_2Pr-c$ | H | H | CH=NOMe | H | 0 | |

TABLE 42

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-460 | $CF_3$ | Me | H | $CH_2Pr$-c | H | H | CH(OH)Me | H | 0 | |
| V-461 | $CF_3$ | Me | H | $CH_2Pr$-c | H | H | COMe | H | 0 | |
| V-462 | $CF_3$ | Me | H | $CH_2Pr$-c | H | H | Cl | H | 0 | |
| V-463 | $CF_3$ | Me | H | $CH_2Pr$-c | H | H | Br | H | 0 | |
| V-464 | $CF_3$ | Me | H | $CH_2Pr$-c | H | H | I | H | 0 | |
| V-465 | $CF_3$ | Me | H | $CH_2Pr$-c | H | H | CHO | H | 1 | |
| V-466 | $CF_3$ | Me | H | $CH_2Pr$-c | H | H | $CH_2OH$ | H | 1 | |
| V-467 | $CF_3$ | Me | H | $CH_2Pr$-c | H | H | $CH_2OMe$ | H | 1 | |
| V-468 | $CF_3$ | Me | H | $CH_2Pr$-c | H | H | $CH=CH_2$ | H | 1 | |
| V-469 | $CF_3$ | Me | H | $CH_2Pr$-c | H | H | $CHBrCHBr_2$ | H | 1 | |
| V-470 | $CF_3$ | Me | H | $CH_2Pr$-c | H | H | $C\equiv CH$ | H | 1 | |
| V-471 | $CF_3$ | Me | H | $CH_2Pr$-c | H | H | $CH_2Cl$ | H | 1 | |
| V-472 | $CF_3$ | Me | H | $CH_2Pr$-c | H | H | $NO_2$ | H | 1 | |
| V-473 | $CF_3$ | Me | H | $CH_2Pr$-c | H | H | $NH_2$ | H | 1 | |
| V-474 | $CF_3$ | Me | H | $CH_2Pr$-c | H | H | NHMe | H | 1 | |
| V-475 | $CF_3$ | Me | H | $CH_2Pr$-c | H | H | $N(Me)_2$ | H | 1 | |
| V-476 | $CF_3$ | Me | H | $CH_2Pr$-c | H | H | NHCOMe | H | 1 | |
| V-477 | $CF_3$ | Me | H | $CH_2Pr$-c | H | H | NHCOBu-t | H | 1 | |
| V-478 | $CF_3$ | Me | H | $CH_2Pr$-c | H | H | $NHCO_2Me$ | H | 1 | |
| V-479 | $CF_3$ | Me | H | $CH_2Pr$-c | H | H | $NHCO_2Bu$-t | H | 1 | |
| V-480 | $CF_3$ | Me | H | $CH_2Pr$-c | H | H | $CO_2H$ | H | 1 | |
| V-481 | $CF_3$ | Me | H | $CH_2Pr$-c | H | H | $CO_2Me$ | H | 1 | |
| V-482 | $CF_3$ | Me | H | $CH_2Pr$-c | H | H | Et | H | 1 | |
| V-483 | $CF_3$ | Me | H | $CH_2Pr$-c | H | H | $CH_2F$ | H | 1 | |
| V-484 | $CF_3$ | Me | H | $CH_2Pr$-c | H | H | $CHF_2$ | H | 1 | |
| V-485 | $CF_3$ | Me | H | $CH_2Pr$-c | H | H | $CF_3$ | H | 1 | |
| V-486 | $CF_3$ | Me | H | $CH_2Pr$-c | H | H | CH=NOH | H | 1 | |
| V-487 | $CF_3$ | Me | H | $CH_2Pr$-c | H | H | CH=NOMe | H | 1 | |
| V-488 | $CF_3$ | Me | H | $CH_2Pr$-c | H | H | CH(OH)Me | H | 1 | |
| V-489 | $CF_3$ | Me | H | $CH_2Pr$-c | H | H | COMe | H | 1 | |
| V-490 | $CF_3$ | Me | H | $CH_2Pr$-c | H | H | Cl | H | 1 | |

TABLE 43

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-491 | $CF_3$ | Me | H | $CH_2Pr$-c | H | H | Br | H | 1 | |
| V-492 | $CF_3$ | Me | H | $CH_2Pr$-c | H | H | I | H | 1 | |
| V-493 | $CF_3$ | Me | H | $CH_2CF_3$ | H | H | CHO | H | 0 | 63-65 |
| V-494 | $CF_3$ | Me | H | $CH_2CF_3$ | H | H | $CH_2OH$ | H | 0 | |
| V-495 | $CF_3$ | Me | H | $CH_2CF_3$ | H | H | $CH_2OMe$ | H | 0 | |
| V-496 | $CF_3$ | Me | H | $CH_2CF_3$ | H | H | $CH=CH_2$ | H | 0 | |
| V-497 | $CF_3$ | Me | H | $CH_2CF_3$ | H | H | $CHBrCHBr_2$ | H | 0 | |
| V-498 | $CF_3$ | Me | H | $CH_2CF_3$ | H | H | $C\equiv CH$ | H | 0 | |
| V-499 | $CF_3$ | Me | H | $CH_2CF_3$ | H | H | $CH_2Cl$ | H | 0 | |
| V-500 | $CF_3$ | Me | H | $CH_2CF_3$ | H | H | $NO_2$ | H | 0 | |
| V-501 | $CF_3$ | Me | H | $CH_2CF_3$ | H | H | $NH_2$ | H | 0 | |
| V-502 | $CF_3$ | Me | H | $CH_2CF_3$ | H | H | NHMe | H | 0 | |
| V-503 | $CF_3$ | Me | H | $CH_2CF_3$ | H | H | $N(Me)_2$ | H | 0 | |
| V-504 | $CF_3$ | Me | H | $CH_2CF_3$ | H | H | NHCOMe | H | 0 | |
| V-505 | $CF_3$ | Me | H | $CH_2CF_3$ | H | H | NHCOBu-t | H | 0 | |
| V-506 | $CF_3$ | Me | H | $CH_2CF_3$ | H | H | $NHCO_2Me$ | H | 0 | |
| V-507 | $CF_3$ | Me | H | $CH_2CF_3$ | H | H | $NHCO_2Bu$-t | H | 0 | |
| V-508 | $CF_3$ | Me | H | $CH_2CF_3$ | H | H | $CO_2H$ | H | 0 | |
| V-509 | $CF_3$ | Me | H | $CH_2CF_3$ | H | H | $CO_2Me$ | H | 0 | |
| V-510 | $CF_3$ | Me | H | $CH_2CF_3$ | H | H | Et | H | 0 | |
| V-511 | $CF_3$ | Me | H | $CH_2CF_3$ | H | H | $CH_2F$ | H | 0 | |
| V-512 | $CF_3$ | Me | H | $CH_2CF_3$ | H | H | $CHF_2$ | H | 0 | |
| V-513 | $CF_3$ | Me | H | $CH_2CF_3$ | H | H | $CF_3$ | H | 0 | |
| V-514 | $CF_3$ | Me | H | $CH_2CF_3$ | H | H | CH=NOH | H | 0 | |
| V-515 | $CF_3$ | Me | H | $CH_2CF_3$ | H | H | CH=NOMe | H | 0 | |
| V-516 | $CF_3$ | Me | H | $CH_2CF_3$ | H | H | CH(OH)Me | H | 0 | |
| V-517 | $CF_3$ | Me | H | $CH_2CF_3$ | H | H | COMe | H | 0 | |
| V-518 | $CF_3$ | Me | H | $CH_2CF_3$ | H | H | Cl | H | 0 | |
| V-519 | $CF_3$ | Me | H | $CH_2CF_3$ | H | H | Br | H | 0 | |
| V-520 | $CF_3$ | Me | H | $CH_2CF_3$ | H | H | I | H | 0 | |
| V-521 | $CF_3$ | Me | H | $CH_2CF_3$ | H | H | CHO | H | 1 | |

TABLE 44

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-522 | $CF_3$ | Me | H | $CH_2CF_3$ | H | H | $CH_2OH$ | H | 1 | |
| V-523 | $CF_3$ | Me | H | $CH_2CF_3$ | H | H | $CH_2OMe$ | H | 1 | |
| V-524 | $CF_3$ | Me | H | $CH_2CF_3$ | H | H | $CH=CH_2$ | H | 1 | |
| V-525 | $CF_3$ | Me | H | $CH_2CF_3$ | H | H | $CHBrCHBr_2$ | H | 1 | |
| V-526 | $CF_3$ | Me | H | $CH_2CF_3$ | H | H | $C\equiv CH$ | H | 1 | |
| V-527 | $CF_3$ | Me | H | $CH_2CF_3$ | H | H | $CH_2Cl$ | H | 1 | |
| V-528 | $CF_3$ | Me | H | $CH_2CF_3$ | H | H | $NO_2$ | H | 1 | |
| V-529 | $CF_3$ | Me | H | $CH_2CF_3$ | H | H | $NH_2$ | H | 1 | |
| V-530 | $CF_3$ | Me | H | $CH_2CF_3$ | H | H | NHMe | H | 1 | |
| V-531 | $CF_3$ | Me | H | $CH_2CF_3$ | H | H | $N(Me)_2$ | H | 1 | |
| V-532 | $CF_3$ | Me | H | $CH_2CF_3$ | H | H | NHCOMe | H | 1 | |
| V-533 | $CF_3$ | Me | H | $CH_2CF_3$ | H | H | NHCOBu-t | H | 1 | |
| V-534 | $CF_3$ | Me | H | $CH_2CF_3$ | H | H | $NHCO_2Me$ | H | 1 | |
| V-535 | $CF_3$ | Me | H | $CH_2CF_3$ | H | H | $NHCO_2Bu$-t | H | 1 | |
| V-536 | $CF_3$ | Me | H | $CH_2CF_3$ | H | H | $CO_2H$ | H | 1 | |
| V-537 | $CF_3$ | Me | H | $CH_2CF_3$ | H | H | $CO_2Me$ | H | 1 | |
| V-538 | $CF_3$ | Me | H | $CH_2CF_3$ | H | H | Et | H | 1 | |
| V-539 | $CF_3$ | Me | H | $CH_2CF_3$ | H | H | $CH_2F$ | H | 1 | |
| V-540 | $CF_3$ | Me | H | $CH_2CF_3$ | H | H | $CHF_2$ | H | 1 | |
| V-541 | $CF_3$ | Me | H | $CH_2CF_3$ | H | H | $CF_3$ | H | 1 | |
| V-542 | $CF_3$ | Me | H | $CH_2CF_3$ | H | H | CH=NOH | H | 1 | |
| V-543 | $CF_3$ | Me | H | $CH_2CF_3$ | H | H | CH=NOMe | H | 1 | |
| V-544 | $CF_3$ | Me | H | $CH_2CF_3$ | H | H | CH(OH)Me | H | 1 | |
| V-545 | $CF_3$ | Me | H | $CH_2CF_3$ | H | H | COMe | H | 1 | |
| V-546 | $CF_3$ | Me | H | $CH_2CF_3$ | H | H | Cl | H | 1 | |
| V-547 | $CF_3$ | Me | H | $CH_2CF_3$ | H | H | Br | H | 1 | |
| V-548 | $CF_3$ | Me | H | $CH_2CF_3$ | H | H | I | H | 1 | |
| V-549 | $CF_3$ | H | H | Pr | H | H | OMe | H | 0 | |
| V-550 | $CF_3$ | H | H | Pr | H | H | OEt | H | 0 | |
| V-551 | $CF_3$ | H | H | Pr | H | H | OPr-i | H | 0 | |
| V-552 | $CF_3$ | H | H | Pr | H | H | $OCHF_2$ | H | 0 | |

TABLE 45

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-553 | $CF_3$ | H | H | Pr | H | H | $OCF_3$ | H | 0 | |
| V-554 | $CF_3$ | Me | H | Pr | H | H | OMe | H | 0 | |
| V-555 | $CF_3$ | Me | H | Pr | H | H | OEt | H | 0 | |
| V-556 | $CF_3$ | Me | H | Pr | H | H | OPr-i | H | 0 | |
| V-557 | $CF_3$ | Me | H | Pr | H | H | $OCHF_2$ | H | 0 | |
| V-558 | $CF_3$ | Me | H | Pr | H | H | $OCF_3$ | H | 0 | |
| V-559 | $CF_3$ | H | H | Pr | H | H | OMe | H | 1 | |
| V-560 | $CF_3$ | H | H | Pr | H | H | OEt | H | 1 | |
| V-561 | $CF_3$ | H | H | Pr | H | H | OPr-i | H | 1 | |
| V-562 | $CF_3$ | H | H | Pr | H | H | $OCHF_2$ | H | 1 | |
| V-563 | $CF_3$ | H | H | Pr | H | H | $OCF_3$ | H | 1 | |
| V-564 | $CF_3$ | Me | H | Pr | H | H | OMe | H | 1 | |
| V-565 | $CF_3$ | Me | H | Pr | H | H | OEt | H | 1 | |
| V-566 | $CF_3$ | Me | H | Pr | H | H | OPr-i | H | 1 | |
| V-567 | $CF_3$ | Me | H | Pr | H | H | $OCHF_2$ | H | 1 | |
| V-568 | $CF_3$ | Me | H | Pr | H | H | $OCF_3$ | H | 1 | |
| V-569 | $CF_3$ | H | H | $CH_2Pr$-c | H | H | OMe | H | 0 | |
| V-570 | $CF_3$ | H | H | $CH_2Pr$-c | H | H | OEt | H | 0 | |
| V-571 | $CF_3$ | H | H | $CH_2Pr$-c | H | H | OPr-i | H | 0 | |
| V-572 | $CF_3$ | H | H | $CH_2Pr$-c | H | H | $OCHF_2$ | H | 0 | |
| V-573 | $CF_3$ | H | H | $CH_2Pr$-c | H | H | $OCF_3$ | H | 0 | |
| V-574 | $CF_3$ | Me | H | $CH_2Pr$-c | H | H | OMe | H | 0 | |
| V-575 | $CF_3$ | Me | H | $CH_2Pr$-c | H | H | OEt | H | 0 | |
| V-576 | $CF_3$ | Me | H | $CH_2Pr$-c | H | H | OPr-i | H | 0 | |
| V-577 | $CF_3$ | Me | H | $CH_2Pr$-c | H | H | $OCHF_2$ | H | 0 | |
| V-578 | $CF_3$ | Me | H | $CH_2Pr$-c | H | H | $OCF_3$ | H | 0 | |
| V-579 | $CF_3$ | H | H | $CH_2Pr$-c | H | H | OMe | H | 1 | |
| V-580 | $CF_3$ | H | H | $CH_2Pr$-c | H | H | OEt | H | 1 | |
| V-581 | $CF_3$ | H | H | $CH_2Pr$-c | H | H | OPr-i | H | 1 | |
| V-582 | $CF_3$ | H | H | $CH_2Pr$-c | H | H | $OCHF_2$ | H | 1 | |
| V-583 | $CF_3$ | H | H | $CH_2Pr$-c | H | H | $OCF_3$ | H | 1 | |

TABLE 46

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-584 | $CF_3$ | Me | H | $CH_2Pr$-c | H | H | OMe | H | 1 | |
| V-585 | $CF_3$ | Me | H | $CH_2Pr$-c | H | H | OEt | H | 1 | |
| V-586 | $CF_3$ | Me | H | $CH_2Pr$-c | H | H | OPr-i | H | 1 | |
| V-587 | $CF_3$ | Me | H | $CH_2Pr$-c | H | H | $OCHF_2$ | H | 1 | |
| V-588 | $CF_3$ | Me | H | $CH_2Pr$-c | H | H | $OCF_3$ | H | 1 | |
| V-589 | $CF_3$ | H | H | $CH_2CF_3$ | H | H | OMe | H | 0 | |
| V-590 | $CF_3$ | H | H | $CH_2CF_3$ | H | H | OEt | H | 0 | |
| V-591 | $CF_3$ | H | H | $CH_2CF_3$ | H | H | OPr-i | H | 0 | |
| V-592 | $CF_3$ | H | H | $CH_2CF_3$ | H | H | $OCHF_2$ | H | 0 | |
| V-593 | $CF_3$ | H | H | $CH_2CF_3$ | H | H | $OCF_3$ | H | 0 | |
| V-594 | $CF_3$ | Me | H | $CH_2CF_3$ | H | H | OMe | H | 0 | |
| V-595 | $CF_3$ | Me | H | $CH_2CF_3$ | H | H | OEt | H | 0 | |
| V-596 | $CF_3$ | Me | H | $CH_2CF_3$ | H | H | OPr-i | H | 0 | |
| V-597 | $CF_3$ | Me | H | $CH_2CF_3$ | H | H | $OCHF_2$ | H | 1 | |
| V-598 | $CF_3$ | Me | H | $CH_2CF_3$ | H | H | $OCF_3$ | H | 1 | |
| V-599 | $CF_3$ | H | H | $CH_2CF_3$ | H | H | OMe | H | 1 | |
| V-600 | $CF_3$ | H | H | $CH_2CF_3$ | H | H | OEt | H | 1 | |
| V-601 | $CF_3$ | H | H | $CH_2CF_3$ | H | H | OPr-i | H | 1 | |
| V-602 | $CF_3$ | H | H | $CH_2CF_3$ | H | H | $OCHF_2$ | H | 1 | |
| V-603 | $CF_3$ | H | H | $CH_2CF_3$ | H | H | $OCF_3$ | H | 1 | |
| V-604 | $CF_3$ | Me | H | $CH_2CF_3$ | H | H | OMe | H | 1 | |
| V-605 | $CF_3$ | Me | H | $CH_2CF_3$ | H | H | OEt | H | 1 | |
| V-606 | $CF_3$ | Me | H | $CH_2CF_3$ | H | H | OPr-i | H | 1 | |
| V-607 | $CF_3$ | Me | H | $CH_2CF_3$ | H | H | $OCHF_2$ | H | 1 | |
| V-608 | $CF_3$ | Me | H | $CH_2CF_3$ | H | H | $OCF_3$ | H | 1 | |
| V-609 | $CF_3$ | H | H | Pr | F | H | Me | H | 0 | |
| V-610 | $CF_3$ | H | H | Pr | F | H | Me | H | 1 | |
| V-611 | $CF_3$ | H | H | $CH_2Pr$-c | F | H | Me | H | 0 | |
| V-612 | $CF_3$ | H | H | $CH_2Pr$-c | F | H | Me | H | 1 | |
| V-613 | $CF_3$ | H | H | $CH_2CF_3$ | F | H | Me | H | 0 | 1.4998 |
| V-614 | $CF_3$ | H | H | $CH_2CF_3$ | F | H | Me | H | 1 | 85-88 |

TABLE 47

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-615 | $CF_3$ | H | H | Pr | F | H | $CHF_2$ | H | 0 | |
| V-616 | $CF_3$ | H | H | Pr | F | H | $CHF_2$ | H | 1 | |
| V-617 | $CF_3$ | H | H | $CH_2Pr$-c | F | H | $CHF_2$ | H | 0 | |
| V-618 | $CF_3$ | H | H | $CH_2Pr$-c | F | H | $CHF_2$ | H | 1 | |
| V-619 | $CF_3$ | H | H | $CH_2CF_3$ | F | H | $CHF_2$ | H | 0 | |
| V-620 | $CF_3$ | H | H | $CH_2CF_3$ | F | H | $CHF_2$ | H | 1 | |
| V-621 | $CF_3$ | H | H | Pr | Cl | H | Me | H | 0 | |
| V-622 | $CF_3$ | H | H | Pr | Cl | H | Me | H | 1 | |
| V-623 | $CF_3$ | H | H | $CH_2Pr$-c | Cl | H | Me | H | 0 | |
| V-624 | $CF_3$ | H | H | $CH_2Pr$-c | Cl | H | Me | H | 1 | |
| V-625 | $CF_3$ | H | H | $CH_2CF_3$ | Cl | H | Me | H | 0 | |
| V-626 | $CF_3$ | H | H | $CH_2CF_3$ | Cl | H | Me | H | 1 | |
| V-627 | $CF_3$ | H | H | Pr | Cl | H | $CHF_2$ | H | 0 | |
| V-628 | $CF_3$ | H | H | Pr | Cl | H | $CHF_2$ | H | 1 | |
| V-629 | $CF_3$ | H | H | $CH_2Pr$-c | Cl | H | $CHF_2$ | H | 0 | |
| V-630 | $CF_3$ | H | H | $CH_2Pr$-c | Cl | H | $CHF_2$ | H | 1 | |
| V-631 | $CF_3$ | H | H | $CH_2CF_3$ | Cl | H | $CHF_2$ | H | 0 | |
| V-632 | $CF_3$ | H | H | $CH_2CF_3$ | Cl | H | $CHF_2$ | H | 1 | |
| V-633 | Me | H | H | $CH_2CF_3$ | H | H | CN | H | 0 | |
| V-634 | Me | H | H | $CH_2CF_3$ | H | H | CN | H | 1 | |
| V-635 | H | $CF_3$ | H | Pr | H | H | CN | H | 0 | 80-81 |
| V-636 | H | $CF_3$ | H | Pr | H | H | CN | H | 1 | 169-170 |
| V-637 | H | $CF_3$ | H | $CH_2Pr$-c | H | H | CN | H | 0 | |
| V-638 | H | $CF_3$ | H | $CH_2Pr$-c | H | H | CN | H | 1 | |
| V-639 | H | $CF_3$ | H | $CH_2CF_3$ | H | H | CN | H | 0 | 90-91 |
| V-640 | H | $CF_3$ | H | $CH_2CF_3$ | H | H | CN | H | 1 | 141-142 |
| V-641 | H | $CF_3$ | H | Pr | H | H | Me | H | 0 | |
| V-642 | H | $CF_3$ | H | Pr | H | H | Me | H | 1 | |
| V-643 | H | $CF_3$ | H | $CH_2Pr$-c | H | H | Me | H | 0 | |
| V-644 | H | $CF_3$ | H | $CH_2Pr$-c | H | H | Me | H | 1 | |
| V-645 | H | $CF_3$ | H | $CH_2CF_3$ | H | H | Me | H | 0 | 1.5052 |

TABLE 48

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-646 | H | $CF_3$ | H | $CH_2CF_3$ | H | H | Me | H | 1 | 90-93 |
| V-647 | H | $CF_3$ | H | Pr | H | H | $CHF_2$ | H | 0 | |
| V-648 | H | $CF_3$ | H | Pr | H | H | $CHF_2$ | H | 1 | |
| V-649 | H | $CF_3$ | H | $CH_2$Pr-c | H | H | $CHF_2$ | H | 0 | |
| V-650 | H | $CF_3$ | H | $CH_2$Pr-c | H | H | $CHF_2$ | H | 1 | |
| V-651 | H | $CF_3$ | H | $CH_2CF_3$ | H | H | $CHF_2$ | H | 0 | 1.5012 |
| V-652 | H | $CF_3$ | H | $CH_2CF_3$ | H | H | $CHF_2$ | H | 1 | 113-115 |
| V-653 | H | I | H | $CH_2CF_3$ | H | H | CN | H | 0 | 131-132 |
| V-654 | H | I | H | $CH_2CF_3$ | H | H | CN | H | 1 | |
| V-655 | H | $CF_3$ | H | Pr | F | H | Me | H | 0 | |
| V-656 | H | $CF_3$ | H | Pr | F | H | Me | H | 1 | |
| V-657 | H | $CF_3$ | H | $CH_2$Pr-c | F | H | Me | H | 0 | 1.5391 |
| V-658 | H | $CF_3$ | H | $CH_2$Pr-c | F | H | Me | H | 1 | 78-80 |
| V-659 | H | $CF_3$ | H | $CH_2CF_3$ | F | H | Me | H | 0 | 37-38 |
| V-660 | H | $CF_3$ | H | $CH_2CF_3$ | F | H | Me | H | 1 | 97-98 |
| V-661 | H | $CF_3$ | H | Pr | F | H | $CHF_2$ | H | 0 | |
| V-662 | H | $CF_3$ | H | Pr | F | H | $CHF_2$ | H | 1 | |
| V-663 | H | $CF_3$ | H | $CH_2$Pr-c | F | H | $CHF_2$ | H | 0 | |
| V-664 | H | $CF_3$ | H | $CH_2$Pr-c | F | H | $CHF_2$ | H | 1 | |
| V-665 | H | $CF_3$ | H | $CH_2CF_3$ | F | H | $CHF_2$ | H | 0 | |
| V-666 | H | $CF_3$ | H | $CH_2CF_3$ | F | H | $CHF_2$ | H | 1 | |
| V-667 | H | $CF_3$ | H | Pr | Cl | H | Me | H | 0 | |
| V-668 | H | $CF_3$ | H | Pr | Cl | H | Me | H | 1 | |
| V-669 | H | $CF_3$ | H | $CH_2$Pr-c | Cl | H | Me | H | 0 | |
| V-670 | H | $CF_3$ | H | $CH_2$Pr-c | Cl | H | Me | H | 1 | |
| V-671 | H | $CF_3$ | H | $CH_2CF_3$ | Cl | H | Me | H | 0 | |
| V-672 | H | $CF_3$ | H | $CH_2CF_3$ | Cl | H | Me | H | 1 | |
| V-673 | H | $CF_3$ | H | Pr | Cl | H | $CHF_2$ | H | 0 | |
| V-674 | H | $CF_3$ | H | Pr | Cl | H | $CHF_2$ | H | 1 | |
| V-675 | H | $CF_3$ | H | $CH_2$Pr-c | Cl | H | $CHF_2$ | H | 0 | |
| V-676 | H | $CF_3$ | H | $CH_2$Pr-c | Cl | H | $CHF_2$ | H | 1 | |

TABLE 49

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-677 | H | $CF_3$ | H | $CH_2CF_3$ | Cl | H | $CHF_2$ | H | 0 | |
| V-678 | H | $CF_3$ | H | $CH_2CF_3$ | Cl | H | $CHF_2$ | H | 1 | |
| V-679 | H | $CF_3$ | H | Pr | Cl | H | $CH=CH_2$ | H | 0 | |
| V-680 | H | $CF_3$ | H | Pr | Cl | H | $CH=CH_2$ | H | 1 | |
| V-681 | H | $CF_3$ | H | $CH_2$Pr-c | Cl | H | $CH=CH_2$ | H | 0 | |
| V-682 | H | $CF_3$ | H | $CH_2$Pr-c | Cl | H | $CH=CH_2$ | H | 1 | |
| V-683 | H | $CF_3$ | H | $CH_2CF_3$ | Cl | H | $CH=CH_2$ | H | 0 | |
| V-684 | H | $CF_3$ | H | $CH_2CF_3$ | Cl | H | $CH=CH_2$ | H | 1 | |
| V-685 | $CF_3$ | Cl | H | $CH_2CF_3$ | H | H | CHO | H | 0 | 88-89 |
| V-686 | $CF_3$ | Cl | H | $CH_2CF_3$ | H | H | $CH_2OH$ | H | 0 | 90-91 |
| V-687 | H | $CF_3$ | H | $CH_2CF_3$ | H | H | CHO | H | 0 | 88-89 |
| V-688 | $CF_3$ | H | H | $CH_2CF_3$ | $SCH_2CF_3$ | H | CN | H | 0 | 112-113 |
| V-689 | H | $CF_3$ | H | $CH_2CF_3$ | H | H | CHO | H | 1 | 162-164 |
| V-690 | H | $CF_3$ | H | Pr | H | H | Cl | H | 0 | |
| V-691 | H | $CF_3$ | H | Pr | H | H | Cl | H | 1 | |
| V-692 | H | $CF_3$ | H | $CH_2$Pr-c | H | H | Cl | H | 0 | 1.5691 |
| V-693 | H | $CF_3$ | H | $CH_2$Pr-c | H | H | Cl | H | 1 | 113-114 |
| V-694 | H | $CF_3$ | H | $CH_2CF_3$ | H | H | Cl | H | 0 | 1.5216 |
| V-695 | H | $CF_3$ | H | $CH_2CF_3$ | H | H | Cl | H | 1 | 109-111 |
| V-696 | $CF_3$ | H | H | Pr | F | H | Cl | H | 0 | |
| V-697 | $CF_3$ | H | H | Pr | F | H | Cl | H | 1 | |
| V-698 | $CF_3$ | H | H | $CH_2$Pr-c | F | H | Cl | H | 0 | 36-39 |
| V-699 | $CF_3$ | H | H | $CH_2$Pr-c | F | H | Cl | H | 1 | 1.5539 |
| V-700 | $CF_3$ | H | H | $CH_2CF_3$ | F | H | Cl | H | 0 | 1.5180 |
| V-701 | $CF_3$ | H | H | $CH_2CF_3$ | F | H | Cl | H | 1 | 150-153 |
| V-702 | H | $CF_3$ | H | Pr | F | H | Cl | H | 0 | |
| V-703 | H | $CF_3$ | H | Pr | F | H | Cl | H | 1 | |
| V-704 | H | $CF_3$ | H | $CH_2$Pr-c | F | H | Cl | H | 0 | |
| V-705 | H | $CF_3$ | H | $CH_2$Pr-c | F | H | Cl | H | 1 | |
| V-706 | H | $CF_3$ | H | $CH_2CF_3$ | F | H | Cl | H | 0 | |
| V-707 | H | $CF_3$ | H | $CH_2CF_3$ | F | H | Cl | H | 1 | 138-140 |

TABLE 50

| Compound No. | $A_{10}$ | $A_8$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|---|
| V-708 | H | $CF_3$ | H | $CH_2CF_3$ | H | H | $CH_2OH$ | H | 0 | 1.5160 |
| V-709 | H | $CF_3$ | H | $CH_2CF_3$ | H | H | $CH_2OH$ | H | 1 | |
| V-710 | $CF_3$ | H | H | $CH_2CF_3$ | H | H | H | H | 0 | 1.5186 |
| V-711 | $CF_3$ | H | H | $CH_2CF_3$ | H | H | H | H | 1 | |
| V-712 | $CF_3$ | H | H | $CH_2CF_3$ | H | H | H | H | 2 | 102-103 |
| V-713 | H | $CF_3$ | H | Pr | Cl | H | Cl | H | 0 | |
| V-714 | H | $CF_3$ | H | Pr | Cl | H | Cl | H | 1 | |
| V-715 | H | $CF_3$ | H | $CH_2Pr$-c | Cl | H | Cl | H | 0 | |
| V-716 | H | $CF_3$ | H | $CH_2Pr$-c | Cl | H | Cl | H | 1 | |
| V-717 | H | $CF_3$ | H | $CH_2CF_3$ | Cl | H | Cl | H | 0 | 1.5291 |
| V-718 | H | $CF_3$ | H | $CH_2CF_3$ | Cl | H | Cl | H | 1 | 118-119 |

TABLE 51

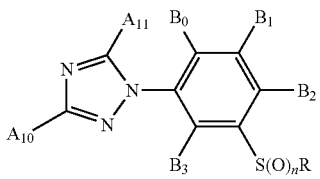

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-1 | $CF_3$ | H | Pr | H | H | CN | H | 0 | 143-144 |
| VI-2 | $CF_3$ | H | Pr | H | H | CN | H | 1 | 159-160 |
| VI-3 | $CF_3$ | H | $CH_2Pr$-c | H | H | CN | H | 0 | 145-146 |
| VI-4 | $CF_3$ | H | $CH_2Pr$-c | H | H | CN | H | 1 | 181-183 |
| VI-5 | $CF_3$ | H | $CH_2CF_3$ | H | H | CN | H | 0 | |
| VI-6 | $CF_3$ | H | $CH_2CF_3$ | H | H | CN | H | 1 | |
| VI-7 | $CF_3$ | H | Pr | H | H | Me | H | 0 | |
| VI-8 | $CF_3$ | H | Pr | H | H | Me | H | 1 | |
| VI-9 | $CF_3$ | H | $CH_2Pr$-c | H | H | Me | H | 0 | |
| VI-10 | $CF_3$ | H | $CH_2Pr$-c | H | H | Me | H | 1 | |
| VI-11 | $CF_3$ | H | $CH_2CF_3$ | H | H | Me | H | 0 | |
| VI-12 | $CF_3$ | H | $CH_2CF_3$ | H | H | Me | H | 1 | |
| VI-13 | $CF_3$ | H | Pr | H | H | $CHF_2$ | H | 0 | |
| VI-14 | $CF_3$ | H | Pr | H | H | $CHF_2$ | H | 1 | |
| VI-15 | $CF_3$ | H | $CH_2Pr$-c | H | H | $CHF_2$ | H | 0 | |
| VI-16 | $CF_3$ | H | $CH_2Pr$-c | H | H | $CHF_2$ | H | 1 | |
| VI-17 | $CF_3$ | H | $CH_2CF_3$ | H | H | $CHF_2$ | H | 0 | 1.5002 |
| VI-18 | $CF_3$ | H | $CH_2CF_3$ | H | H | $CHF_2$ | H | 1 | 1.4982 |
| VI-19 | $CF_3$ | H | Pr | F | H | CN | H | 0 | |
| VI-20 | $CF_3$ | H | Pr | F | H | CN | H | 1 | |
| VI-21 | $CF_3$ | H | $CH_2Pr$-c | F | H | CN | H | 0 | |
| VI-22 | $CF_3$ | H | $CH_2Pr$-c | F | H | CN | H | 1 | |
| VI-23 | $CF_3$ | H | $CH_2CF_3$ | F | H | CN | H | 0 | |

TABLE 52

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-24 | $CF_3$ | H | $CH_2CF_3$ | F | H | CN | H | 1 | |
| VI-25 | $CF_3$ | H | Pr | F | H | Me | H | 0 | |
| VI-26 | $CF_3$ | H | Pr | F | H | Me | H | 1 | |
| VI-27 | $CF_3$ | H | $CH_2Pr$-c | F | H | Me | H | 0 | |
| VI-28 | $CF_3$ | H | $CH_2Pr$-c | F | H | Me | H | 1 | |
| VI-29 | $CF_3$ | H | $CH_2CF_3$ | F | H | Me | H | 0 | |
| VI-30 | $CF_3$ | H | $CH_2CF_3$ | F | H | Me | H | 1 | |
| VI-31 | $CF_3$ | H | Pr | F | H | $CHF_2$ | H | 0 | |
| VI-32 | $CF_3$ | H | Pr | F | H | $CHF_2$ | H | 1 | |
| VI-33 | $CF_3$ | H | $CH_2Pr$-c | F | H | $CHF_2$ | H | 0 | |
| VI-34 | $CF_3$ | H | $CH_2Pr$-c | F | H | $CHF_2$ | H | 1 | |
| VI-35 | $CF_3$ | H | $CH_2CF_3$ | F | H | $CHF_2$ | H | 0 | |
| VI-36 | $CF_3$ | H | $CH_2CF_3$ | F | H | $CHF_2$ | H | 1 | |
| VI-37 | $CF_3$ | H | Pr | Cl | H | CN | H | 0 | |
| VI-38 | $CF_3$ | H | Pr | Cl | H | CN | H | 1 | |
| VI-39 | $CF_3$ | H | $CH_2Pr$-c | Cl | H | CN | H | 0 | |
| VI-40 | $CF_3$ | H | $CH_2Pr$-c | Cl | H | CN | H | 1 | |
| VI-41 | $CF_3$ | H | $CH_2CF_3$ | Cl | H | CN | H | 0 | |
| VI-42 | $CF_3$ | H | $CH_2CF_3$ | Cl | H | CN | H | 1 | |
| VI-43 | $CF_3$ | H | Pr | Cl | H | Me | H | 0 | |
| VI-44 | $CF_3$ | H | Pr | Cl | H | Me | H | 1 | |
| VI-45 | $CF_3$ | H | $CH_2Pr$-c | Cl | H | Me | H | 0 | |
| VI-46 | $CF_3$ | H | $CH_2Pr$-c | Cl | H | Me | H | 1 | |
| VI-47 | $CF_3$ | H | $CH_2CF_3$ | Cl | H | Me | H | 0 | |
| VI-48 | $CF_3$ | H | $CH_2CF_3$ | Cl | H | Me | H | 1 | |
| VI-49 | $CF_3$ | H | Pr | Cl | H | $CHF_2$ | H | 0 | |
| VI-50 | $CF_3$ | H | Pr | Cl | H | $CHF_2$ | H | 1 | |
| VI-51 | $CF_3$ | H | $CH_2Pr$-c | Cl | H | $CHF_2$ | H | 0 | |
| VI-52 | $CF_3$ | H | $CH_2Pr$-c | Cl | H | $CHF_2$ | H | 1 | |
| VI-53 | $CF_3$ | H | $CH_2CF_3$ | Cl | H | $CHF_2$ | H | 0 | |
| VI-54 | $CF_3$ | H | $CH_2CF_3$ | Cl | H | $CHF_2$ | H | 1 | |

TABLE 53

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-55 | $CF_3$ | $NH_2$ | Pr | H | H | CN | H | 0 | |
| VI-56 | $CF_3$ | $NH_2$ | Pr | H | H | CN | H | 1 | |
| VI-57 | $CF_3$ | $NH_2$ | $CH_2Pr$-c | H | H | CN | H | 0 | |
| VI-58 | $CF_3$ | $NH_2$ | $CH_2Pr$-c | H | H | CN | H | 1 | |
| VI-59 | $CF_3$ | $NH_2$ | $CH_2CF_3$ | H | H | CN | H | 0 | |
| VI-60 | $CF_3$ | $NH_2$ | $CH_2CF_3$ | H | H | CN | H | 1 | |
| VI-61 | $CF_3$ | $NH_2$ | Pr | H | H | Me | H | 0 | |

TABLE 53-continued

| Compound No. | $A_{10}$ | $A_{11}$ | R | $B_0$ | $B_1$ | $B_2$ | $B_3$ | n | m.p. (°C.) or RI ($n_D^{20}$) |
|---|---|---|---|---|---|---|---|---|---|
| VI-62 | $CF_3$ | $NH_2$ | Pr | H | H | Me | H | 1 | |
| VI-63 | $CF_3$ | $NH_2$ | $CH_2Pr$-c | H | H | Me | H | 0 | |
| VI-64 | $CF_3$ | $NH_2$ | $CH_2Pr$-c | H | H | Me | H | 1 | |
| VI-65 | $CF_3$ | $NH_2$ | $CH_2CF_3$ | H | H | Me | H | 0 | |
| VI-66 | $CF_3$ | $NH_2$ | $CH_2CF_3$ | H | H | Me | H | 1 | |
| VI-67 | $CF_3$ | $NH_2$ | Pr | H | H | $CHF_2$ | H | 0 | |
| VI-68 | $CF_3$ | $NH_2$ | Pr | H | H | $CHF_2$ | H | 1 | |
| VI-69 | $CF_3$ | $NH_2$ | $CH_2Pr$-c | H | H | $CHF_2$ | H | 0 | |
| VI-70 | $CF_3$ | $NH_2$ | $CH_2Pr$-c | H | H | $CHF_2$ | H | 1 | |
| VI-71 | $CF_3$ | $NH_2$ | $CH_2CF_3$ | H | H | $CHF_2$ | H | 0 | |
| VI-72 | $CF_3$ | $NH_2$ | $CH_2CF_3$ | H | H | $CHF_2$ | H | 1 | |
| VI-73 | $CF_3$ | H | Pr | H | H | CHO | H | 0 | |
| VI-74 | $CF_3$ | H | Pr | H | H | $CH_2OH$ | H | 0 | |
| VI-75 | $CF_3$ | H | Pr | H | H | $CH_2OMe$ | H | 0 | |
| VI-76 | $CF_3$ | H | Pr | H | H | $CH=CH_2$ | H | 0 | |
| VI-77 | $CF_3$ | H | Pr | H | H | $CHBrCHBr_2$ | H | 0 | |
| VI-78 | $CF_3$ | H | Pr | H | H | $C\equiv CH$ | H | 0 | |
| VI-79 | $CF_3$ | H | Pr | H | H | $CH_2Cl$ | H | 0 | |
| VI-80 | $CF_3$ | H | Pr | H | H | $NO_2$ | H | 0 | |
| VI-81 | $CF_3$ | H | Pr | H | H | $NH_2$ | H | 0 | |
| VI-82 | $CF_3$ | H | Pr | H | H | NHMe | H | 0 | |
| VI-83 | $CF_3$ | H | Pr | H | H | $N(Me)_2$ | H | 0 | |
| VI-84 | $CF_3$ | H | Pr | H | H | NHCOMe | H | 0 | |
| VI-85 | $CF_3$ | H | Pr | H | H | NHCOBu-t | H | 0 | |

TABLE 54

| Compound No. | $A_{10}$ | $A_{11}$ | R | $B_0$ | $B_1$ | $B_2$ | $B_3$ | n | m.p. (°C.) or RI ($n_D^{20}$) |
|---|---|---|---|---|---|---|---|---|---|
| VI-86 | $CF_3$ | H | Pr | H | H | $NHCO_2Me$ | H | 0 | |
| VI-87 | $CF_3$ | H | Pr | H | H | $NHCO_2Bu$-t | H | 0 | |
| VI-88 | $CF_3$ | H | Pr | H | H | $CO_2H$ | H | 0 | |
| VI-89 | $CF_3$ | H | Pr | H | H | $CO_2Me$ | H | 0 | |
| VI-90 | $CF_3$ | H | Pr | H | H | Et | H | 0 | |
| VI-91 | $CF_3$ | H | Pr | H | H | $CH_2F$ | H | 0 | |
| VI-92 | $CF_3$ | H | Pr | H | H | $CF_3$ | H | 0 | |
| VI-93 | $CF_3$ | H | Pr | H | H | CH=NOH | H | 0 | |
| VI-94 | $CF_3$ | H | Pr | H | H | CH=NOMe | H | 0 | |
| VI-95 | $CF_3$ | H | Pr | H | H | CH(OH)Me | H | 0 | |
| VI-96 | $CF_3$ | H | Pr | H | H | COMe | H | 0 | |
| VI-97 | $CF_3$ | H | Pr | H | H | Cl | H | 0 | |
| VI-98 | $CF_3$ | H | Pr | H | H | Br | H | 0 | |
| VI-99 | $CF_3$ | H | Pr | H | H | I | H | 0 | |
| VI-100 | $CF_3$ | H | Pr | H | H | CHO | H | 1 | |
| VI-101 | $CF_3$ | H | Pr | H | H | $CH_2OH$ | H | 1 | |
| VI-102 | $CF_3$ | H | Pr | H | H | $CH_2OMe$ | H | 1 | |
| VI-103 | $CF_3$ | H | Pr | H | H | $CH=CH_2$ | H | 1 | |
| VI-104 | $CF_3$ | H | Pr | H | H | $CHBrCHBr_2$ | H | 1 | |
| VI-105 | $CF_3$ | H | Pr | H | H | $C\equiv CH$ | H | 1 | |
| VI-106 | $CF_3$ | H | Pr | H | H | $CH_2Cl$ | H | 1 | |
| VI-107 | $CF_3$ | H | Pr | H | H | $NO_2$ | H | 1 | |
| VI-108 | $CF_3$ | H | Pr | H | H | $NH_2$ | H | 1 | |
| VI-109 | $CF_3$ | H | Pr | H | H | NHMe | H | 1 | |
| VI-110 | $CF_3$ | H | Pr | H | H | $N(Me)_2$ | H | 1 | |
| VI-111 | $CF_3$ | H | Pr | H | H | NHCOMe | H | 1 | |
| VI-112 | $CF_3$ | H | Pr | H | H | NHCOBu-t | H | 1 | |
| VI-113 | $CF_3$ | H | Pr | H | H | $NHCO_2Me$ | H | 1 | |
| VI-114 | $CF_3$ | H | Pr | H | H | $NHCO_2Bu$-t | H | 1 | |
| VI-115 | $CF_3$ | H | Pr | H | H | $CO_2H$ | H | 1 | |
| VI-116 | $CF_3$ | H | Pr | H | H | $CO_2Me$ | H | 1 | |

TABLE 55

| Compound No. | $A_{10}$ | $A_{11}$ | R | $B_0$ | $B_1$ | $B_2$ | $B_3$ | n | m.p. (°C.) or RI ($n_D^{20}$) |
|---|---|---|---|---|---|---|---|---|---|
| VI-117 | $CF_3$ | H | Pr | H | H | Et | H | 1 | |
| VI-118 | $CF_3$ | H | Pr | H | H | $CH_2F$ | H | 1 | |
| VI-119 | $CF_3$ | H | Pr | H | H | $CF_3$ | H | 1 | |
| VI-120 | $CF_3$ | H | Pr | H | H | CH=NOH | H | 1 | |
| VI-121 | $CF_3$ | H | Pr | H | H | CH=NOMe | H | 1 | |
| VI-122 | $CF_3$ | H | Pr | H | H | CH(OH)Me | H | 1 | |
| VI-123 | $CF_3$ | H | Pr | H | H | COMe | H | 1 | |
| VI-124 | $CF_3$ | H | Pr | H | H | Cl | H | 1 | |
| VI-125 | $CF_3$ | H | Pr | H | H | Br | H | 1 | |
| VI-126 | $CF_3$ | H | Pr | H | H | I | H | 1 | |
| VI-127 | $CF_3$ | H | $CH_2Pr$-c | H | H | CHO | H | 0 | |

TABLE 55-continued

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-128 | $CF_3$ | H | $CH_2Pr$-c | H | H | $CH_2OH$ | H | 0 | |
| VI-129 | $CF_3$ | H | $CH_2Pr$-c | H | H | $CH_2OMe$ | H | 0 | |
| VI-130 | $CF_3$ | H | $CH_2Pr$-c | H | H | $CH=CH_2$ | H | 0 | |
| VI-131 | $CF_3$ | H | $CH_2Pr$-c | H | H | $CHBrCHBr_2$ | H | 0 | |
| VI-132 | $CF_3$ | H | $CH_2Pr$-c | H | H | $C\equiv CH$ | H | 0 | |
| VI-133 | $CF_3$ | H | $CH_2Pr$-c | H | H | $CH_2Cl$ | H | 0 | |
| VI-134 | $CF_3$ | H | $CH_2Pr$-c | H | H | $NO_2$ | H | 0 | |
| VI-135 | $CF_3$ | H | $CH_2Pr$-c | H | H | $NH_2$ | H | 0 | |
| VI-136 | $CF_3$ | H | $CH_2Pr$-c | H | H | NHMe | H | 0 | |
| VI-137 | $CF_3$ | H | $CH_2Pr$-c | H | H | $N(Me)_2$ | H | 0 | |
| VI-138 | $CF_3$ | H | $CH_2Pr$-c | H | H | NHCOMe | H | 0 | |
| VI-139 | $CF_3$ | H | $CH_2Pr$-c | H | H | NHCOBu-t | H | 0 | |
| VI-140 | $CF_3$ | H | $CH_2Pr$-c | H | H | $NHCO_2Me$ | H | 0 | |
| VI-141 | $CF_3$ | H | $CH_2Pr$-c | H | H | $NHCO_2Bu$-t | H | 0 | |
| VI-142 | $CF_3$ | H | $CH_2Pr$-c | H | H | $CO_2H$ | H | 0 | |
| VI-143 | $CF_3$ | H | $CH_2Pr$-c | H | H | $CO_2Me$ | H | 0 | |
| VI-144 | $CF_3$ | H | $CH_2Pr$-c | H | H | Et | H | 0 | |
| VI-145 | $CF_3$ | H | $CH_2Pr$-c | H | H | $CH_2F$ | H | 0 | |
| VI-146 | $CF_3$ | H | $CH_2Pr$-c | H | H | $CF_3$ | H | 0 | |
| VI-147 | $CF_3$ | H | $CH_2Pr$-c | H | H | CH=NOH | H | 0 | |

TABLE 56

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-148 | $CF_3$ | H | $CH_2Pr$-c | H | H | CH=NOMe | H | 0 | |
| VI-149 | $CF_3$ | H | $CH_2Pr$-c | H | H | CH(OH)Me | H | 0 | |
| VI-150 | $CF_3$ | H | $CH_2Pr$-c | H | H | COMe | H | 0 | |
| VI-151 | $CF_3$ | H | $CH_2Pr$-c | H | H | Cl | H | 0 | |
| VI-152 | $CF_3$ | H | $CH_2Pr$-c | H | H | Br | H | 0 | |
| VI-153 | $CF_3$ | H | $CH_2Pr$-c | H | H | I | H | 0 | |
| VI-154 | $CF_3$ | H | $CH_2Pr$-c | H | H | CHO | H | 1 | |
| VI-155 | $CF_3$ | H | $CH_2Pr$-c | H | H | $CH_2OH$ | H | 1 | |
| VI-156 | $CF_3$ | H | $CH_2Pr$-c | H | H | $CH_2OMe$ | H | 1 | |
| VI-157 | $CF_3$ | H | $CH_2Pr$-c | H | H | $CH=CH_2$ | H | 1 | |
| VI-158 | $CF_3$ | H | $CH_2Pr$-c | H | H | $CHBrCHBr_2$ | H | 1 | |
| VI-159 | $CF_3$ | H | $CH_2Pr$-c | H | H | $C\equiv CH$ | H | 1 | |
| VI-160 | $CF_3$ | H | $CH_2Pr$-c | H | H | $CH_2Cl$ | H | 1 | |
| VI-161 | $CF_3$ | H | $CH_2Pr$-c | H | H | $NO_2$ | H | 1 | |
| VI-162 | $CF_3$ | H | $CH_2Pr$-c | H | H | $NH_2$ | H | 1 | |
| VI-163 | $CF_3$ | H | $CH_2Pr$-c | H | H | NHMe | H | 1 | |
| VI-164 | $CF_3$ | H | $CH_2Pr$-c | H | H | $N(Me)_2$ | H | 1 | |
| VI-165 | $CF_3$ | H | $CH_2Pr$-c | H | H | NHCOMe | H | 1 | |
| VI-166 | $CF_3$ | H | $CH_2Pr$-c | H | H | NHCOBu-t | H | 1 | |
| VI-167 | $CF_3$ | H | $CH_2Pr$-c | H | H | $NHCO_2Me$ | H | 1 | |
| VI-168 | $CF_3$ | H | $CH_2Pr$-c | H | H | $NHCO_2Bu$-t | H | 1 | |
| VI-169 | $CF_3$ | H | $CH_2Pr$-c | H | H | $CO_2H$ | H | 1 | |
| VI-170 | $CF_3$ | H | $CH_2Pr$-c | H | H | $CO_2Me$ | H | 1 | |
| VI-171 | $CF_3$ | H | $CH_2Pr$-c | H | H | Et | H | 1 | |
| VI-172 | $CF_3$ | H | $CH_2Pr$-c | H | H | $CH_2F$ | H | 1 | |
| VI-173 | $CF_3$ | H | $CH_2Pr$-c | H | H | $CF_3$ | H | 1 | |
| VI-174 | $CF_3$ | H | $CH_2Pr$-c | H | H | CH=NOH | H | 1 | |
| VI-175 | $CF_3$ | H | $CH_2Pr$-c | H | H | CH=NOMe | H | 1 | |
| VI-176 | $CF_3$ | H | $CH_2Pr$-c | H | H | CH(OH)Me | H | 1 | |
| VI-177 | $CF_3$ | H | $CH_2Pr$-c | H | H | COMe | H | 1 | |
| VI-178 | $CF_3$ | H | $CH_2Pr$-c | H | H | Cl | H | 1 | |

TABLE 57

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-179 | $CF_3$ | H | $CH_2Pr$-c | H | H | Br | H | 1 | |
| VI-180 | $CF_3$ | H | $CH_2Pr$-c | H | H | I | H | 1 | |

TABLE 57-continued

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-181 | $CF_3$ | H | $CH_2CF_3$ | H | H | CHO | H | 0 | 67-68 |
| VI-182 | $CF_3$ | H | $CH_2CF_3$ | H | H | $CH_2OH$ | H | 0 | 96-100 |
| VI-183 | $CF_3$ | H | $CH_2CF_3$ | H | H | $CH_2OMe$ | H | 0 | |
| VI-184 | $CF_3$ | H | $CH_2CF_3$ | H | H | $CH=CH_2$ | H | 0 | |
| VI-185 | $CF_3$ | H | $CH_2CF_3$ | H | H | $CHBrCHBr_2$ | H | 0 | |
| VI-186 | $CF_3$ | H | $CH_2CF_3$ | H | H | C≡CH | H | 0 | |
| VI-187 | $CF_3$ | H | $CH_2CF_3$ | H | H | $CH_2Cl$ | H | 0 | |
| VI-188 | $CF_3$ | H | $CH_2CF_3$ | H | H | $NO_2$ | H | 0 | |
| VI-189 | $CF_3$ | H | $CH_2CF_3$ | H | H | $NH_2$ | H | 0 | |
| VI-190 | $CF_3$ | H | $CH_2CF_3$ | H | H | NHMe | H | 0 | |
| VI-191 | $CF_3$ | H | $CH_2CF_3$ | H | H | $N(Me)_2$ | H | 0 | |
| VI-192 | $CF_3$ | H | $CH_2CF_3$ | H | H | NHCOMe | H | 0 | |
| VI-193 | $CF_3$ | H | $CH_2CF_3$ | H | H | NHCOBu-t | H | 0 | |
| VI-194 | $CF_3$ | H | $CH_2CF_3$ | H | H | $NHCO_2Me$ | H | 0 | |
| VI-195 | $CF_3$ | H | $CH_2CF_3$ | H | H | $NHCO_2Bu$-t | H | 0 | |
| VI-196 | $CF_3$ | H | $CH_2CF_3$ | H | H | $CO_2H$ | H | 0 | |
| VI-197 | $CF_3$ | H | $CH_2CF_3$ | H | H | $CO_2Me$ | H | 0 | |
| VI-198 | $CF_3$ | H | $CH_2CF_3$ | H | H | Et | H | 0 | |
| VI-199 | $CF_3$ | H | $CH_2CF_3$ | H | H | $CH_2F$ | H | 0 | 1.5258 |
| VI-200 | $CF_3$ | H | $CH_2CF_3$ | H | H | $CF_3$ | H | 0 | |
| VI-201 | $CF_3$ | H | $CH_2CF_3$ | H | H | CH=NOH | H | 0 | |
| VI-202 | $CF_3$ | H | $CH_2CF_3$ | H | H | CH=NOMe | H | 0 | |
| VI-203 | $CF_3$ | H | $CH_2CF_3$ | H | H | CH(OH)Me | H | 0 | |
| VI-204 | $CF_3$ | H | $CH_2CF_3$ | H | H | COMe | H | 0 | |
| VI-205 | $CF_3$ | H | $CH_2CF_3$ | H | H | Cl | H | 0 | |
| VI-206 | $CF_3$ | H | $CH_2CF_3$ | H | H | Br | H | 0 | |
| VI-207 | $CF_3$ | H | $CH_2CF_3$ | H | H | I | H | 0 | |
| VI-208 | $CF_3$ | H | $CH_2CF_3$ | H | H | CHO | H | 1 | 142-143 |
| VI-209 | $CF_3$ | H | $CH_2CF_3$ | H | H | $CH_2OH$ | H | 1 | |

TABLE 58

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-210 | $CF_3$ | H | $CH_2CF_3$ | H | H | $CH_2OMe$ | H | 1 | |
| VI-211 | $CF_3$ | H | $CH_2CF_3$ | H | H | $CH=CH_2$ | H | 1 | |
| VI-212 | $CF_3$ | H | $CH_2CF_3$ | H | H | $CHBrCHBr_2$ | H | 1 | |
| VI-213 | $CF_3$ | H | $CH_2CF_3$ | H | H | C≡CH | H | 1 | |
| VI-214 | $CF_3$ | H | $CH_2CF_3$ | H | H | $CH_2Cl$ | H | 1 | |
| VI-215 | $CF_3$ | H | $CH_2CF_3$ | H | H | $NO_2$ | H | 1 | |
| VI-216 | $CF_3$ | H | $CH_2CF_3$ | H | H | $NH_2$ | H | 1 | |
| VI-217 | $CF_3$ | H | $CH_2CF_3$ | H | H | NHMe | H | 1 | |
| VI-218 | $CF_3$ | H | $CH_2CF_3$ | H | H | $N(Me)_2$ | H | 1 | |
| VI-219 | $CF_3$ | H | $CH_2CF_3$ | H | H | NHCOMe | H | 1 | |
| VI-220 | $CF_3$ | H | $CH_2CF_3$ | H | H | NHCOBu-t | H | 1 | |
| VI-221 | $CF_3$ | H | $CH_2CF_3$ | H | H | $NHCO_2Me$ | H | 1 | |
| VI-222 | $CF_3$ | H | $CH_2CF_3$ | H | H | $NHCO_2Bu$-t | H | 1 | |
| VI-223 | $CF_3$ | H | $CH_2CF_3$ | H | H | $CO_2H$ | H | 1 | |
| VI-224 | $CF_3$ | H | $CH_2CF_3$ | H | H | $CO_2Me$ | H | 1 | |
| VI-225 | $CF_3$ | H | $CH_2CF_3$ | H | H | Et | H | 1 | |
| VI-226 | $CF_3$ | H | $CH_2CF_3$ | H | H | $CH_2F$ | H | 1 | 1.5041 |
| VI-227 | $CF_3$ | H | $CH_2CF_3$ | H | H | $CF_3$ | H | 1 | |
| VI-228 | $CF_3$ | H | $CH_2CF_3$ | H | H | CH=NOH | H | 1 | |
| VI-229 | $CF_3$ | H | $CH_2CF_3$ | H | H | CH=NOMe | H | 1 | |
| VI-230 | $CF_3$ | H | $CH_2CF_3$ | H | H | CH(OH)Me | H | 1 | |
| VI-231 | $CF_3$ | H | $CH_2CF_3$ | H | H | COMe | H | 1 | |
| VI-232 | $CF_3$ | H | $CH_2CF_3$ | H | H | Cl | H | 1 | |
| VI-233 | $CF_3$ | H | $CH_2CF_3$ | H | H | Br | H | 1 | |
| VI-234 | $CF_3$ | H | $CH_2CF_3$ | H | H | I | H | 1 | |
| VI-235 | $CF_3$ | H | Et | H | H | Me | H | 0 | |
| VI-236 | $CF_3$ | H | Pr-i | H | H | Me | H | 0 | |
| VI-237 | $CF_3$ | H | Bu | H | H | Me | H | 0 | |
| VI-238 | $CF_3$ | H | Bu-i | H | H | Me | H | 0 | |
| VI-239 | $CF_3$ | H | Bu-s | H | H | Me | H | 0 | |
| VI-240 | $CF_3$ | H | Bu-t | H | H | Me | H | 0 | |

TABLE 59

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-241 | $CF_3$ | H | $CH_2CH_2Cl$ | H | H | Me | H | 0 | |
| VI-242 | $CF_3$ | H | Pr-c | H | H | Me | H | 0 | |
| VI-243 | $CF_3$ | H | Bu-c | H | H | Me | H | 0 | |
| VI-244 | $CF_3$ | H | Pen-c | H | H | Me | H | 0 | |
| VI-245 | $CF_3$ | H | Hex-c | H | H | Me | H | 0 | |
| VI-246 | $CF_3$ | H | $CH_2$Bu-c | H | H | Me | H | 0 | |
| VI-247 | $CF_3$ | H | $CH_2$Pen-c | H | H | Me | H | 0 | |
| VI-248 | $CF_3$ | H | $CH_2$Hex-c | H | H | Me | H | 0 | |
| VI-249 | $CF_3$ | H | Et | H | H | Me | H | 1 | |
| VI-250 | $CF_3$ | H | Pr-i | H | H | Me | H | 1 | |
| VI-251 | $CF_3$ | H | Bu | H | H | Me | H | 1 | |
| VI-252 | $CF_3$ | H | Bu-i | H | H | Me | H | 1 | |
| VI-253 | $CF_3$ | H | Bu-s | H | H | Me | H | 1 | |
| VI-254 | $CF_3$ | H | Bu-t | H | H | Me | H | 1 | |
| VI-255 | $CF_3$ | H | $CH_2CH_2Cl$ | H | H | Me | H | 1 | |
| VI-256 | $CF_3$ | H | Pr-c | H | H | Me | H | 1 | |
| VI-257 | $CF_3$ | H | Bu-c | H | H | Me | H | 1 | |
| VI-258 | $CF_3$ | H | Pen-c | H | H | Me | H | 1 | |
| VI-259 | $CF_3$ | H | Hex-c | H | H | Me | H | 1 | |
| VI-260 | $CF_3$ | H | $CH_2$Bu-c | H | H | Me | H | 1 | |
| VI-261 | $CF_3$ | H | $CH_2$Pen-c | H | H | Me | H | 1 | |
| VI-262 | $CF_3$ | H | $CH_2$Hex-c | H | H | Me | H | 1 | |
| VI-263 | $CF_3$ | H | Et | H | H | $CHF_2$ | H | 0 | |
| VI-264 | $CF_3$ | H | Pr-i | H | H | $CHF_2$ | H | 0 | |
| VI-265 | $CF_3$ | H | Bu | H | H | $CHF_2$ | H | 0 | |
| VI-266 | $CF_3$ | H | Bu-i | H | H | $CHF_2$ | H | 0 | |
| VI-267 | $CF_3$ | H | Bu-s | H | H | $CHF_2$ | H | 0 | |
| VI-268 | $CF_3$ | H | Bu-t | H | H | $CHF_2$ | H | 0 | |
| VI-269 | $CF_3$ | H | $CH_2CH_2Cl$ | H | H | $CHF_2$ | H | 0 | |
| VI-270 | $CF_3$ | H | Pr-c | H | H | $CHF_2$ | H | 0 | |
| VI-271 | $CF_3$ | H | Bu-c | H | H | $CHF_2$ | H | 0 | |

TABLE 60

| Compound No. | $A_{10}$ | $A_{11}$ | R | $B_0$ | $B_1$ | $B_2$ | $B_3$ | n | m.p. (° C.) or RI ($n_D^{20}$) |
|---|---|---|---|---|---|---|---|---|---|
| VI-272 | $CF_3$ | H | Pen-c | H | H | $CHF_2$ | H | 0 | |
| VI-273 | $CF_3$ | H | Hex-c | H | H | $CHF_2$ | H | 0 | |
| VI-274 | $CF_3$ | H | $CH_2$Bu-c | H | H | $CHF_2$ | H | 0 | |
| VI-275 | $CF_3$ | H | $CH_2$Pen-c | H | H | $CHF_2$ | H | 0 | |
| VI-276 | $CF_3$ | H | $CH_2$Hex-c | H | H | $CHF_2$ | H | 0 | |
| VI-277 | $CF_3$ | H | Et | H | H | $CHF_2$ | H | 1 | |
| VI-278 | $CF_3$ | H | Pr-i | H | H | $CHF_2$ | H | 1 | |
| VI-279 | $CF_3$ | H | Bu | H | H | $CHF_2$ | H | 1 | |
| VI-280 | $CF_3$ | H | Bu-i | H | H | $CHF_2$ | H | 1 | |
| VI-281 | $CF_3$ | H | Bu-s | H | H | $CHF_2$ | H | 1 | |
| VI-282 | $CF_3$ | H | Bu-t | H | H | $CHF_2$ | H | 1 | |
| VI-283 | $CF_3$ | H | $CH_2CH_2Cl$ | H | H | $CHF_2$ | H | 1 | |
| VI-284 | $CF_3$ | H | Pr-c | H | H | $CHF_2$ | H | 1 | |
| VI-285 | $CF_3$ | H | Bu-c | H | H | $CHF_2$ | H | 1 | |
| VI-286 | $CF_3$ | H | Pen-c | H | H | $CHF_2$ | H | 1 | |
| VI-287 | $CF_3$ | H | Hex-c | H | H | $CHF_2$ | H | 1 | |
| VI-288 | $CF_3$ | H | $CH_2$Bu-c | H | H | $CHF_2$ | H | 1 | |
| VI-289 | $CF_3$ | H | $CH_2$Pen-c | H | H | $CHF_2$ | H | 1 | |
| VI-290 | $CF_3$ | H | $CH_2$Hex-c | H | H | $CHF_2$ | H | 1 | |
| VI-291 | $CF_3$ | H | $CH_2CF_3$ | F | H | Cl | H | 0 | 56-58 |
| VI-292 | $CF_3$ | H | $CH_2CF_3$ | F | H | Cl | H | 1 | 130-132 |
| VI-293 | $CF_3$ | H | $CH_2CF_3$ | F | H | Me | H | 0 | |
| VI-294 | $CF_3$ | H | $CH_2CF_3$ | F | H | Me | H | 1 | |
| VI-295 | $CF_3$ | H | $CH_2CF_3$ | Cl | H | Me | H | 0 | |
| VI-296 | $CF_3$ | H | $CH_2CF_3$ | Cl | H | Me | H | 1 | |
| VI-297 | $CF_3$ | H | $CH_2CF_3$ | Me | H | Me | H | 0 | |
| VI-298 | $CF_3$ | H | $CH_2CF_3$ | Me | H | Me | H | 1 | |
| VI-299 | $CF_3$ | H | $CH_2CF_3$ | Me | H | Cl | H | 0 | |
| VI-300 | $CF_3$ | H | $CH_2CF_3$ | Me | H | Cl | H | 1 | |

The compounds represented by general formula (I) are obtainable by the processes described below, but their production is not restricted to these processes.

<Process 1>

A compound (I) represented by general formula (I) of the present invention having a phenyl group substituted with an $RS(O)_n$ group can be obtained by using a 3-arylphenylthiol as the starting material.

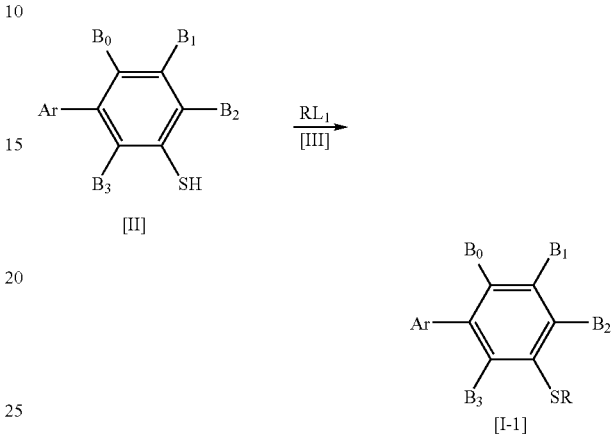

(wherein $L_1$ is a halogen atom, an alkylsulfonyloxy group, a phenylsulfonyloxy group or $SO_2M$, and M is an alkali metal or an alkaline earth metal [preferably sodium or potassium].)

That is, a compound represented by general formula (II) yields a 3-arylphenyl sulfide derivative represented by general formula (I-1) as intended when reacted with from 1 to 5 moles of a compound represented by general formula (III) in from 0.5 to 10 l of a solvent in the presence of from 1 to 5 moles of a base or from 1 to 5 moles of a radical initiator, in relation to 1 mole of the compound represented by general formula (II).

The solvent may, for example, be an ether such as diethyl ether, tetrahydrofuran or dioxane, an aromatic hydrocarbon such as benzene, toluene, xylene or chlorobenzene, a halogenated hydrocarbon such as dichloromethane, chloroform or dichloroethane, an aprotic polar solvent such as N,N-dimethylformamide, N,N-dimethylacetamide, N-methyl-2-pyrrolidone, dimethyl sulfoxide or sulforane, an alcohol such as methanol, ethanol or isopropyl alcohol, a nitrile such acetonitrile or propionitrile, an ester such as ethyl acetate or ethyl propionate, an aliphatic hydrocarbon such as pentane, hexane, cyclohexane or heptane, a pyridine such as pyridine or picoline or water, or a solvent mixture thereof.

The base may, for example, be an inorganic base, e.g. an alkali metal hydroxide such as sodium hydroxide or potassium hydroxide, an alkaline earth metal hydroxide such as calcium hydroxide or magnesium hydroxide, an alkali metal carbonate such as sodium carbonate or potassium carbonate or an alkali metal bicarbonate such as sodium hydrogen carbonate or potassium hydrogen carbonate, a metal hydride such as sodium hydride or potassium hydride, a metal salt of an alcohol such as sodium methoxide, sodium ethoxide or potassium tert-butoxide or an organic base such as tiethylamine, N,N-dimethylaniline, pyridine, 4-N,N-dimethylaminopyridine or 1,8-diazabicyclo[5.4.0]-7-undecene.

The radical initiator may, for example, be sulfurous acid, a sulfite salt or a sulfite adduct such as Rongalite (sodium formaldehyde sulfoxylate). The base and the radical initiator may be used together.

The reaction is carried out at an arbitrary temperature within the range of from −30° C. to the reflux temperature of the reaction system, preferably from 0° C. to 150° C., and completed in from 10 minutes to 20 hours, depending on the compound.

<Process 2>

A compound represented by general formula (I-1) of the present invention is also obtainable by using a compound represented by general formula (IV), which is the oxidative dimer of a compound represented by general is formula (II) used in Process 1, as the starting material.

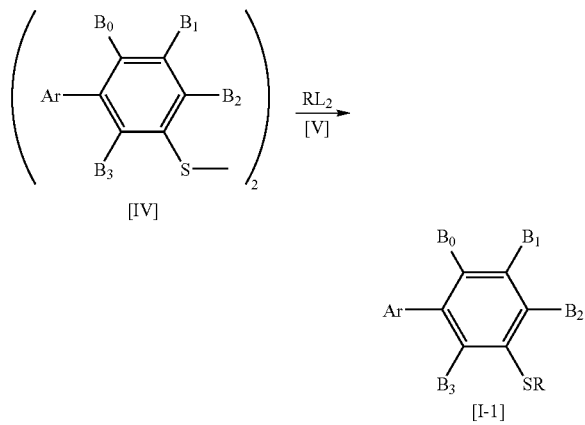

(wherein $L_2$ is a halogen atom or a sulfinate salt, and Ar, $B_0$ to $B_3$ and R are as defined above.)

That is, a compound represented by general formula (IV) yields a 3-arylphenyl sulfide derivative represented by general formula (I-1) as intended when reacted with from 1 to 5 moles of a compound represented by general formula (V) in from 0.5 to 10 l of a solvent in the presence of from 1 to 5 moles of a radical initiator (the same as defined for Process 1), in relation to 1 mole of the compound represented by general formula (IV).

The solvent may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethyl sulfoxide or sulforane, a nitrile such acetonitrile or propionitrile, an ester such as ethyl acetate or ethyl propionate, an aliphatic hydrocarbon such as pentane, hexane, cyclohexane or heptane, a pyridine such as pyridine or picoline or water, or a solvent mixture thereof.

The radical initiator may be used in combination with the base described for Process 1.

The reaction is carried out at an arbitrary temperature within the range of from –30° C. to the reflux temperature of the reaction system, preferably from 0° C. to 150° C., and completed in from 10 minutes to 20 hours, depending on the compound.

<Process 3>

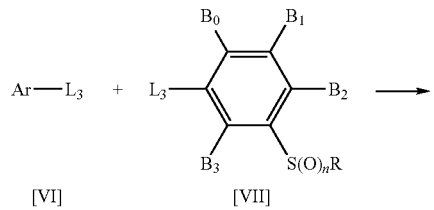

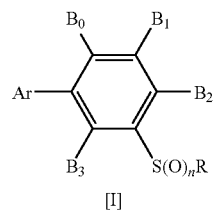

(wherein $L_3$ is a halogen atom, and Ar is a group represented by general formula (Ar-1) or general formula (Ar-3), and $B_0$ to $B_3$, R and n are the same as defined above.)

That is, a compound represented by general formula (VI) or general formula (VII) yields a 3-arylphenyl sulfide derivative represented by general formula (I) as intended when reacted with from 1 to 2 moles of a metal (such as lithium, magnesium or zinc) or an organometal compound (such as n-butyllithium) in from 0.5 to 10 l of a solvent and then with from 1 to 5 moles of the other compound represented by general formula (VI) or general formula (VII) in the presence or absence of from 0.01 to 1 mole of a transition metal catalyst.

The solvent may, for example, be an ether such as diethyl ether, tetrahydrofuran or dioxane, an aromatic hydrocarbon such as benzene, toluene, xylene or chlorobenzene, an aliphatic hydrocarbon such as pentane, hexane, cyclohexane or heptane, a pyridine such as pyridine or picoline, or a solvent mixture thereof.

The transition metal catalyst may, for example, be a palladium compound such as palladium acetate, dichlorobis(triphenylphosphine) palladium, tetrakis(triphenylphosphine)palladium or tris(dibenzalacetone) palladium or a nickel compound such as bis(triphenylphosphine) nickel chloride or tetrakis (triphenylphosphine) nickel.

The reaction is carried out at an arbitrary temperature within the range of from –90° C. to the reflux temperature of the reaction system, preferably from –78° C. to 60° C., and completed in from 10 minutes to 20 hours, depending on the compound.

As $L_3$ as defined above, a bromine atom or an iodine atom is generally preferable, but when the reaction of a compound represented by general formula (VII) with a metal or an organometal compound is followed by treatment with a benzene derivative of general formula (VI) wherein neither $A_1$ nor $A_5$ is a hydrogen atom, $L_3$ is preferably a fluorine atom.

<Process 4>

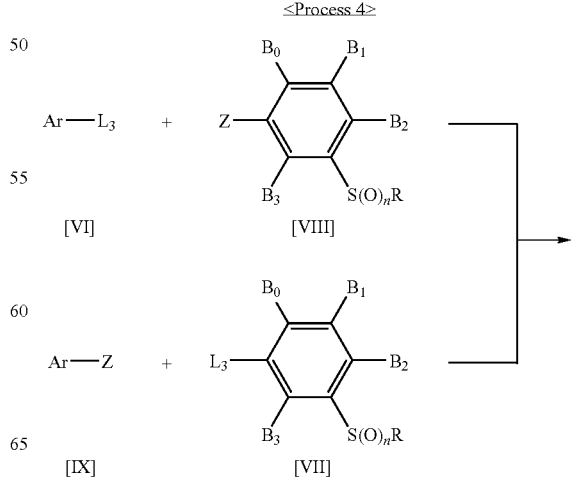

-continued

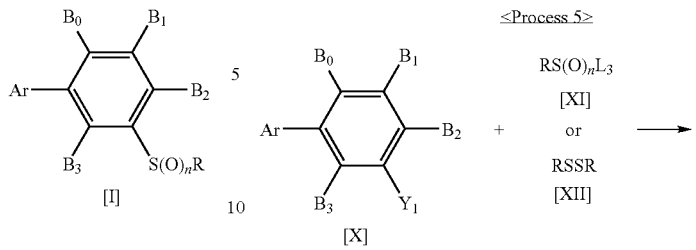

[I]

(wherein Z is a trialkylstannyl group [preferably a trimethylstannyl group], a dihydroxyboranyl group or a dialkoxyboranyl group [preferably a 1,3-dioxobororan-2-yl group or a dimethoxyboranyl group], Ar is a group represented by general formula (Ar-1) or general formula (Ar-3), and $B_0$ to $B_3$, $L_3$ [preferably being a bromine atom or an iodine atom], R and n are the same as defined above.)

That is, a compound represented by general formula (VIII) or (IX) yields a 3-arylphenyl sulfide derivative represented by general formula (I) as intended when reacted with from 1 to 5 moles of a compound represented by general formula (VI) or (VII) in from 0.5 to 10 l of a solvent (as defined for Process 1) in the presence of from 1 to 5 moles of a base (the same as defined for Process 1) and from 0.01 to 1 mole of a transition metal catalyst (the same as defined for Process 3), in relation to 1 mole of the compound represented by general formula (VIII) or (IX).

When Z mentioned above is a dihydroxyboranyl group, instead of a compound represented by general formula (VIII) or (IX), its dehydrated trimer, which is a boroxine represented by general formula (VIII-1) or (IX-1), may be used.

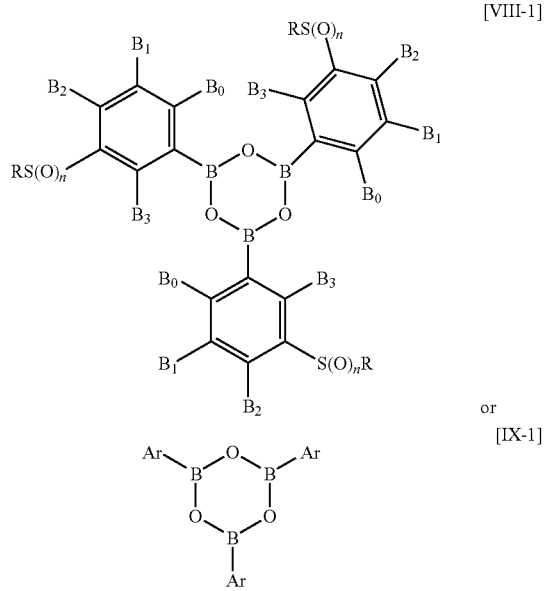

(wherein Ar is represented by general formula (Ar-1) or general formula (Ar-3), and $B_0$ to $B_3$, R and n are the same as defined above.)

The reaction is carried out at an arbitrary temperature within the range of from −70° C. to the reflux temperature of the reaction system, preferably from −20° C. to 100° C., and completed in from 10 minutes to 20 hours, depending on the compound.

<Process 5>

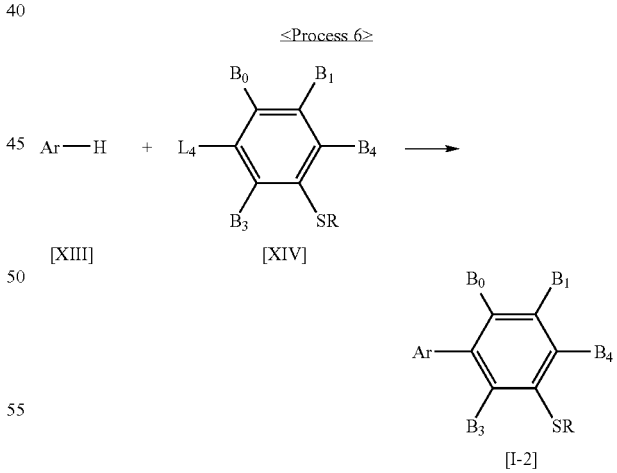

(wherein $Y_1$ is a hydrogen atom or a halogen atom, Ar is a group represented by general formula (Ar-1), (Ar-3) or (Ar-4), and $L_3$, $B_0$ to $B_3$, R and n are the same as defined above.)

That is, a compound represented by general formula (X) yields a 3-arylphenyl sulfide derivative represented by general formula (I) as intended when reacted with from 1 to 3 moles of a metal (such as lithium or magnesium) or an organometal compound (such as n-butyllithium) in from 0.5 to 10 l of a solvent (as defined for Process 3) and then with from 1 to 5 moles of a compound represented by general formula (XI) or general formula (XII), in relation to 1 mole of the compound represented by general formula (X).

The reaction is carried out at an arbitrary temperature within the range of from −90° C. to the reflux temperature of the reaction system, preferably from −78° C. to 70° C., and completed in from 10 minutes to 20 hours, depending on the compound.

<Process 6>

(wherein Ar is a group represented by general formula (Ar-2) or general formula (Ar-4), $B_4$ is an electron-withdrawing group within the above definition of $B_2$ [such as a cyano group, a nitro group or an alkoxycarbonyl group], $B_0$, $B_1$, $B_3$ and R are the same as defined above, and $L_4$ is a halogen atom, an alkylsulfonyloxy group or a phenylsulfonyloxy group.)

That is, a compound represented by general formula (XIII) yields a 3-arylphenyl sulfide derivative represented by general formula (I-2) as intended when reacted with from 1 to 5 moles of a compound represented by general formula (XIV) in from 0.5 to 10 l of a solvent in the presence of from 1 to 5 moles of a base (the same as defined for Process 1), in relation to 1 mole of the compound represented by general formula (XIII).

The solvent may be any solvent that does not inhibit the reaction and may, for example, be an aromatic hydrocarbon such as benzene, toluene or xylene, an ether such as diethyl ether, tetrahydrofuran, 1,2-dimethoxyethane or dioxane, a ketone such as acetone or methyl ethyl ketone, a nitrile such acetonitrile or propionitrile, an aprotic polar solvent such as dimethyl sulfoxide, N,N-dimethylformamide or N,N-dimethylacetamide, an aliphatic hydrocarbon such as pentane, hexane, cyclohexane or heptane, a pyridine such as pyridine or picoline, or a solvent mixture thereof.

The reaction is carried out at an arbitrary temperature within the range of from –70° C. to the reflux temperature of the reaction system, preferably from –20° C. to 150° C., and completed in from 10 minutes to 20 hours, depending on the compound.

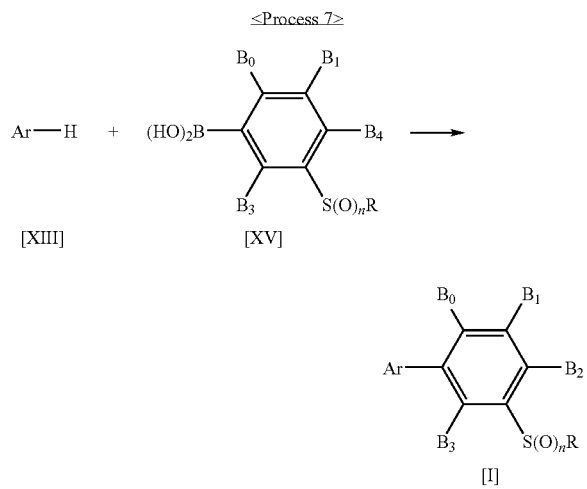

[XIII]  [XV]

[I]

(wherein Ar is a group represented by general formula (Ar-2) or general formula (Ar-4), and $B_0$ to $B_3$, R and n are the same as defined above.)

That is, a compound represented by general formula (XIII) yields a 3-arylphenyl sulfide derivative represented by general formula (I) as intended when reacted with from 1 to 5 moles of a compound represented by general formula (XV) and an anhydrous copper salt (such as anhydrous copper acetate) in from 0.5 to 10 l of a solvent in the presence or absence of from 5 to 50 g of 3 to a 4 Å-molecular sieve in the presence of from 1 to 5 moles of an organic base (such as triethylamine, N,N-dimethylaniline, pyridine, 4-N,N-dimethylaminopyridine or 1,8-diazabicyclo[5.4.0]-7-undecene), in relation to 1 mole of the compound represented by general (XIII).

The solvent may be any solvent that does not inhibit the reaction and may, for example, be a haloalkane such as chloroform or dichloromethane, an aromatic hydrocarbon such as benzene, toluene or xylene, an ether such as diethyl ether, tetrahydrofuran, 1,2-dimethoxyethane or dioxane, a ketone such as acetone or methyl ethyl ketone, a nitrile such as acetonitrile or propionitrile, an aprotic polar solvent such as N,N-dimethylformamide or N,N-dimethylacetamide, an aliphatic hydrocarbon such as pentane, hexane, cyclohexane or heptane, a pyridine such as pyridine or picoline, or a solvent mixture thereof.

The reaction is carried out at an arbitrary temperature within the range of from –70° C. to the reflux temperature of the reaction system, preferably from –20° C. to 150° C., and completed in from 10 minutes to 72 hours, depending on the compound.

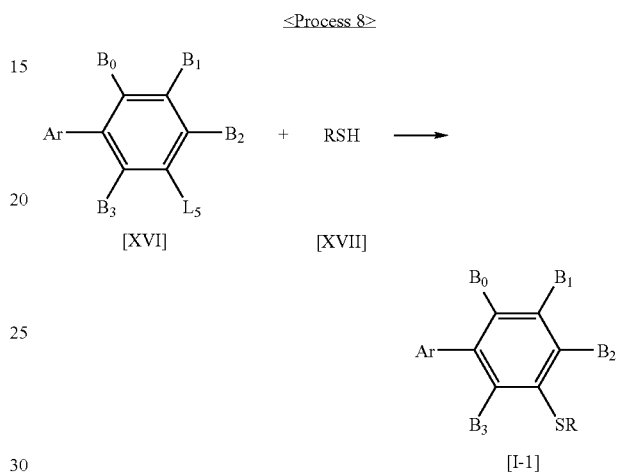

[XVI]  [XVII]

[I-1]

(wherein Ar is a group represented by any one of general formulae (Ar-1) to (Ar-4), $B_0$ to $B_3$ and R are the same as defined above, $L_5$ is a halogen atom, an alkylsulfonyloxy group, a phenylsulfonyloxy group, an alkylsulfonyl group, a phenylsulfonyl group or a nitro group.)

That is, a compound represented by general formula (XVI) yields a 3-arylphenyl sulfide derivative represented by general formula (I-1) as intended when reacted with from 1 to 5 moles of a compound represented by general formula (XVII) (which is also produced from a mineral acid salt of isothiourea having an R group on the sulfur atom as a substituent and an alkali hydroxide or an alkali carbonate) in from 0.5 to 10 l of a solvent in the presence of from 1 to 5 moles of a base, in relation to 1 mole of the compound represented by general (XVI).

The solvent may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethyl sulfoxide or sulforane, an alcohol such as methanol, ethanol or methyl cellosolve, an aliphatic hydrocarbon such as pentane, hexane, cyclohexane or heptane, a pyridine such as pyridine or picoline or water, or a solvent mixture thereof.

The base may be the base as described for Process 1 or copper monoxide.

The reaction is carried out at an arbitrary temperature within the range of from –70° C. to the reflux temperature of the reaction system, preferably from 0° C. to 150° C., and completed in from 10 minutes to 20 hours, depending on the compound.

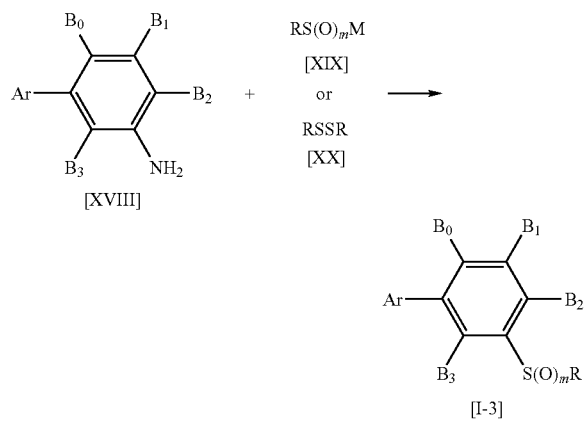

(wherein Ar, $B_0$ to $B_3$, R and M are the same as defined above, and m is 0 or 2.)

That is, a compound represented by general formula (XVIII) yields a 3-arylphenyl sulfide derivative represented by general formula (I-3) as intended when converted into the diazonium salt in from 0.5 to 10 l of a solvent (the same as defined for Process 1) by a conventional method [using a mineral acid (such as hydrochloric acid or sulfuric acid) and a sulfite salt or an alkyl sulfite] and then reacted with from 1 to 5 moles of a mercaptan salt or a sulfinate salt represented by general formula (XIX), or a disulfide represented by general formula (XX), in relation to 1 mole of the compound represented by general formula (XVIII).

The reaction is carried out at an arbitrary temperature within the range of from −30° C. to the reflux temperature of the reaction system, preferably from −10° C. to 100° C., and completed in from 10 minutes to 20 hours, depending on the compound.

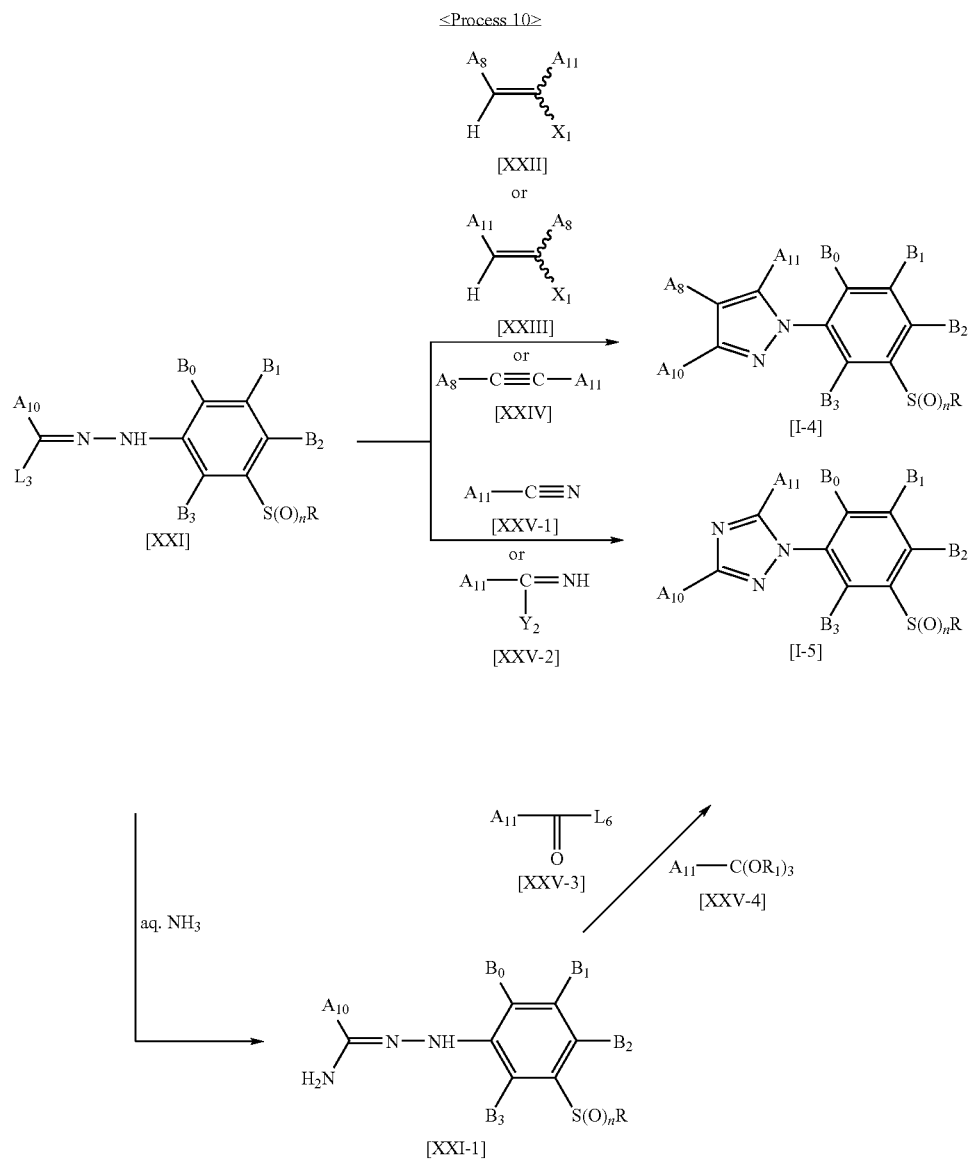

(wherein $X_1$ is a halogen atom, an alkoxy group, an acyloxy group, an alkylsulfonyloxy group or a phenylsulfonyloxy group, $Y_2$ is an alkoxy group or an alkylthio group, $L_6$ is a halogen atom, an acyloxy group, an alkylsulfonyloxy group or a phenylsulfonyloxy group, $R_1$ is an alkyl group, and $L_3$, $A_8$, $A_{10}$, $A_{11}$, $B_0$ to $B_3$, R and n are the same as defined above.)

A compound of the present invention represented by general formula (I-4) is also obtainable by a common 1,3-ring-forming dipolar addition reaction (disclosed, for example, in JP-A-63-287768 or Comprehensive Heterocyclic Chemistry vol. 10, p. 283), and a compound of the present invention represented by general formula (I-5) is also obtainable by a cyclization reaction with a nitrile derivative (disclosed, for example, in JP-A-1-230562 or comprehensive Heterocyclic Chemistry vol. 5, p. 769).

That is, a compound represented by general formula (XXI) yields a pyrazolylphenyl sulfide derivative represented by general formula (I-4) as intended when reacted with from 1 to 5 moles of a compound represented by general formula (XXII), general formula (XXIII) or general formula (XXIV) in from 0.5 to 10 l of a solvent (the same as defined for Process 1) in the presence of from 1 to 5 moles of a base (as defined for Process 1), in relation to 1 mole of the compound represented by general formula (XXI).

A compound represented by general formula (XXI) yields a triazolylphenyl sulfide represented by general formula (I-5) as intended when reacted with from 1 to 5 moles of a compound represented by general formula (XXV-1) or a compound represented by general formula (XXV-2) in from 0.5 to 10 l of a solvent (the same as defined for Process 1) in the presence of from 1 to 5 moles of a base (the same as defined for Process 1), in relation to 1 mole of the compound represented by general formula (XXI).

Alternatively, a compound represented by general formula (XXI) also yields a triazolylphenyl sulfide represented by general formula (I-5) as intended when converted into an amidrazone (XXI-1) by treatment with from 1 to 3 moles of aqueous ammonia and then reacted in from 0.5 to 10 l of a solvent (the same as defined for Process 1) with an acid halide represented by general formula (XXV-3) in the presence of from 1 to 5 moles of a base (the same as defined for Process 1) or with from 1 to 5 moles of an orthoester represented by general formula (XXV-4) in the presence of from 1 to 5 moles of an acid catalyst (such as a sulfonic acid like p-toluenesulfonic acid or a Lewis acid like titanium tetrachloride), in relation to 1 mole of the compound represented by general formula (XXI).

The reaction is carried out at an arbitrary temperature within the range of from −30° C. to the reflux temperature of the reaction system, preferably from −10° C. to 100° C., and completed in from 10 minutes to 20 hours, depending on the compound.

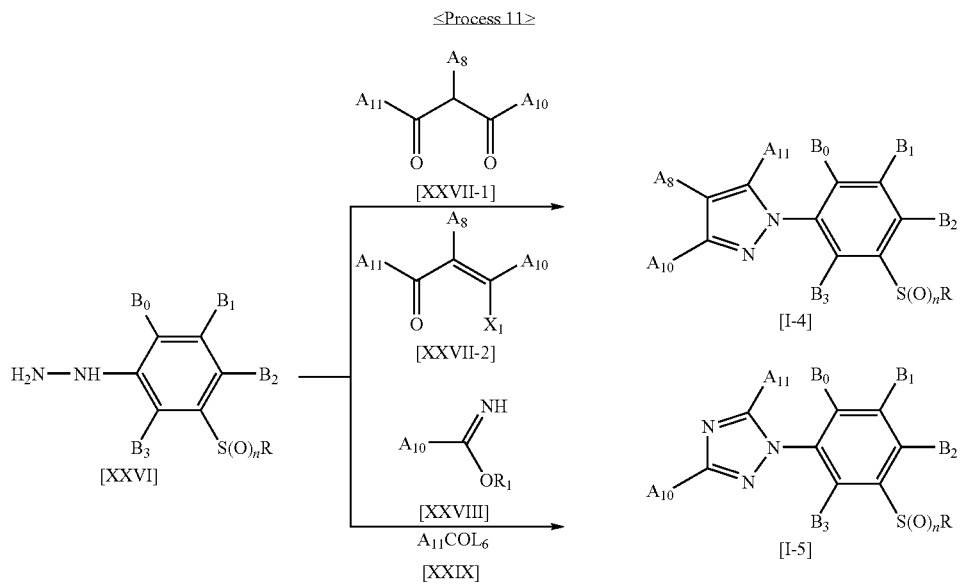

<Process 11>

(wherein $L_6$, $R_1$, $X_1$, $A_8$, $A_{10}$, $A_{11}$, $B_0$ to $B_3$, R and n are the same as defined above.)

That is, a compound represented by general formula (XXVI) yields a 3-pyrazolylphenyl sulfide derivative represented by general formula (I-4) as intended when reacted with from 1 to 5 moles of a compound represented by general formula (XXVII-1) or a compound represented by general formula (XXVII-2) in from 0.5 to 10 l of a solvent (the same as defined for Process 1) in the presence of from 1 to 5 moles of a base (the same as defined for Process 1), in relation to 1 mole of the compound represented by general formula (XXVI).

Also, a compound represented by general formula (XXVI) yields a 3-triazolylphenyl sulfide derivative represented by general formula (I-5) as intended when reacted with from 1 to 5 moles of a compound represented by general formula (XXVIII) or a mineral acid salt thereof and compound represented by general formula (XXIX) in from 0.5 to 10 l of a solvent (the same as defined for Process 1) in the presence of from 1 to 5 moles of a base (the same as defined for Process 1), in relation to 1 mole of the compound represented by general formula (XXVI).

The reaction is carried out at an arbitrary temperature within the range of from −30° C. to the reflux temperature of the reaction system, preferably from −10° C. to 100° C., and completed in from 10 minutes to 20 hours, depending on the compound.

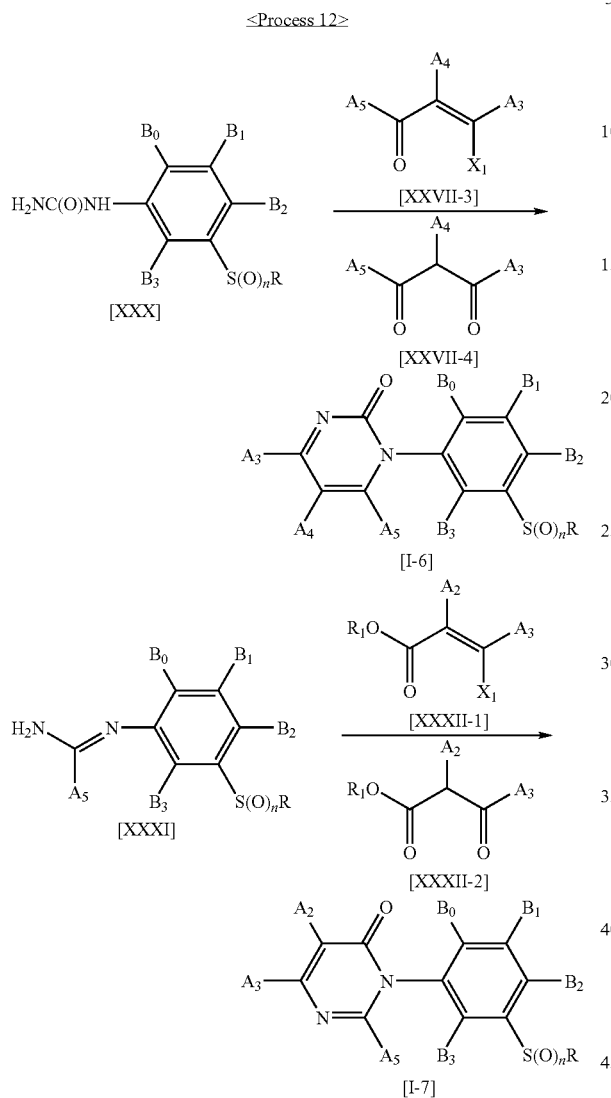

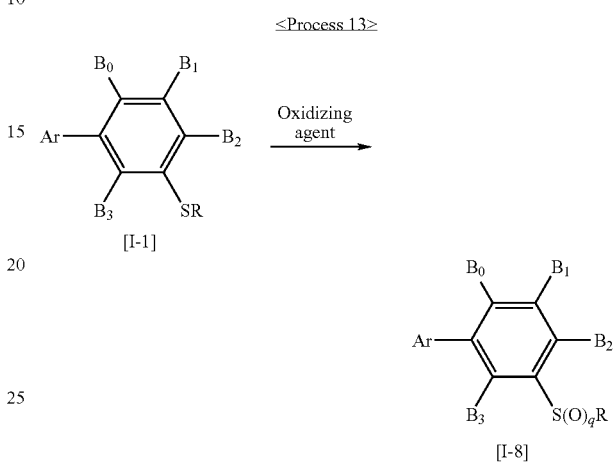

(Wherein $R_1$, $X_1$, $A_2$ to $A_5$, $B_0$ to $B_3$, R and n are the same as defined above.)

That is, a compound represented by general formula (XXX) yields a 3-(2-oxopyrimidinyl)phenyl sulfide derivative represented by general formula (I-6) as intended when reacted with from 1 to 5 moles of a compound represented by general formula (XXVII-3) or a compound represented by general formula (XXVII-4) in from 0.5 to 10 l of a solvent (the same as defined for Process 1) in the presence of from 1 to 5 moles of a base (the same as defined for Process 1), in relation to 1 mole of the compound represented by general formula (XXX).

Also, a compound represented by general formula (XXXI) yields a 3-(6-oxopyrimidinyl)phenyl sulfide derivative represented by general formula (I-7) as intended when reacted with from 1 to 5 moles of a compound represented by general formula (XXXII-1) or a compound represented by general formula (XXXII-2) in from 0.5 to 10 l of a solvent (the same as defined for Process 1) in the presence of from 1 to 5 moles of a base (the same as defined for Process 1), in relation to 1 mole of the compound represented by general formula (XXXI).

The reaction is carried out at an arbitrary temperature within the range of from −30° C. to the reflux temperature of the reaction system, preferably from −10° C. to 100° C., and completed in from 10 minutes to 20 hours, depending on the compound.

(wherein Ar, $B_0$ to $B_3$ and R are the same as defined above and q is 1 or 2.)

That is, a compound of the present invention represented by general formula (I-1) yields a 3-arylphenyl sulfide derivative represented by general formula (I-8) as intended when oxidized with from 1 to 6 moles of an oxidizing agent in from 0.5 to 10 l of a solvent, optionally in the presence of a catalyst (such as sodium tungstate), in relation to 1 mole of the compound represented by general formula (I-1).

The oxidizing agent may, for example, be hydrogen peroxide, m-chloroperbenzoic acid, sodium periodate, OXONE (trade name, manufactured by E.I. du Pont; containing potassium hydrogenperoxosulfate), N-chlorosuccinimide, N-bromosuccinimide, hypochlorous acid, tert-butylsodium or sodium hypochlorite.

The solvent may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethyl sulfoxide or sulforane, an alcohol such as methanol, ethanol or isopropyl alcohol, a halogenated hydrocarbon such as methylene chloride, chloroform or dichloroethane, an aliphatic hydrocarbon such as pentane, hexane, cyclohexane or heptane, a ketone such as acetone, methyl ethyl ketone or cyclohexanone, acetic acid or water, or a solvent mixture thereof.

The reaction is carried out at an arbitrary temperature within the range of from −30° C. to the reflux temperature of the reaction system, preferably from −10° C. to 100° C., and completed in from 10 minutes to 20 hours, depending on the compound.

Compounds of the present invention represented by general formula (I) are obtainable by using other compounds of the present invention, as in Process 13. Namely, a compound of the present invention represented by general formula (I) can be obtained from another compound of the present invention by introducing or converting a functional group by generally known methods (see. Examples 13 to 17; however, such processes are not limited thereto).

Now, syntheses of the precursors of the compounds of the present invention are described below in detail.

<Process 14> Syntheses of Precursors Represented by General Formulae (II) and (IV)

Compound represented by general formulae (II) and (IV) can be synthesized as follows and are interconvertible through oxidation-reduction reaction. Especially, a compound represented by general formula (II) can be easily oxidized by atmospheric oxygen into a compound represented by general formula (IV).

Also, a compound represented by general formula (XXXV) yields a precursor represented by general formula (II) as intended when converted into a sulfonyl chloride (XXXVI) with from 1 to 5 moles of chlorosulfonic acid and reduced with from 1 to 5 moles of lithium aluminum hydride, zinc and an acid, tin and an acid or red phosphorus and iodine, in relation to 1 mole of the compound represented by general formula (XXXV).

Further, a compound represented by general formula (XXXV) yields a precursor represented by general formula (IV) when reacted with from 0.4 to 1.0 mole of sulfur monochloride in from 0.5 to 10 l of an inert solvent such as

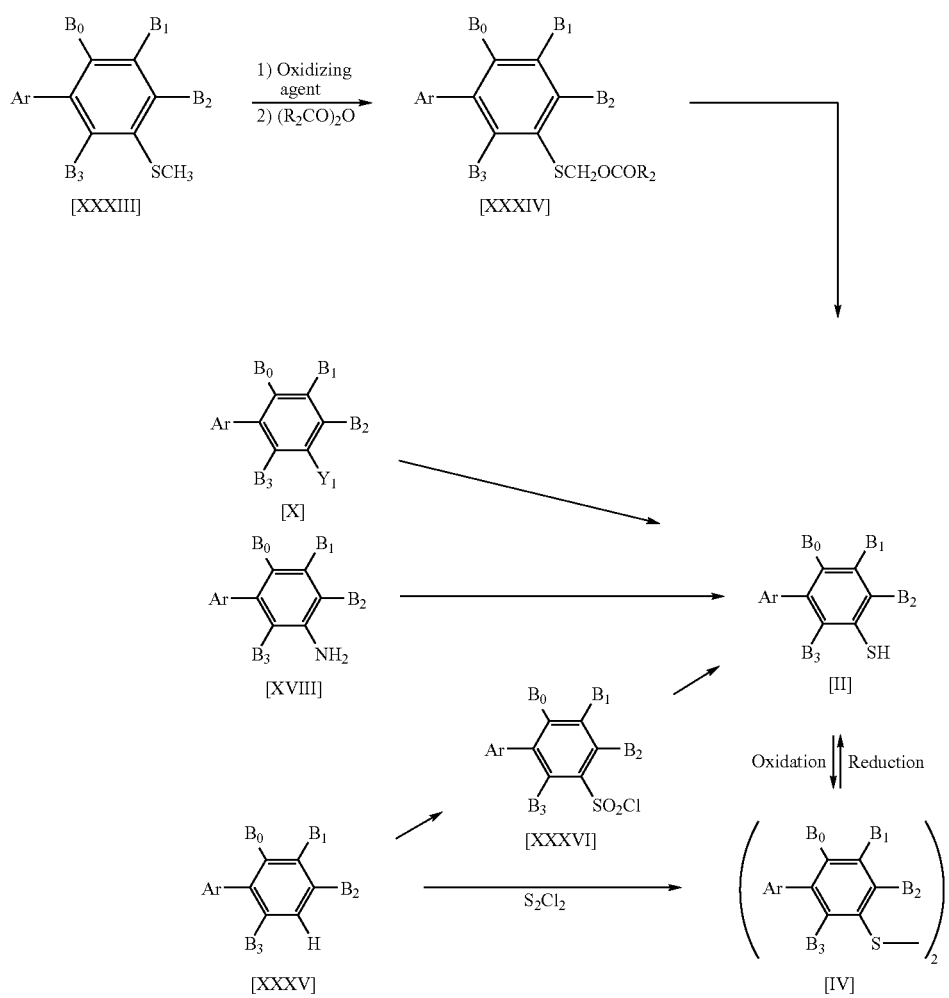

(wherein $R_2$ is a methyl group or a trifluoromethyl group, and Ar, $B_0$ to $B_3$ and $Y_1$ are the same as defined above.)

That is, a compound represented by general formula (XXXIII) yields a compound represented by general formula (II) or (IV) as intended after oxidation into a methyl sulfoxide in from 0.5 to 10 l of a solvent (the same as defined for Process 13) with from 1 to 3 moles of an oxidizing agent (the same as defined for Process 13) followed by the Pummere rearrangement reaction into the corresponding alkyloxymethyl sulfide (XXIV) with from 1 to 5 moles of acetic anhydride or trifluoroacetic anhydride and hydrolysis, in relation to the compound represented by general formula (XXXIII).

carbon disulfide, nitrobenzene or o-dichlorobenzene in the presence of from 0.01 to 2.0 moles of a Lewis acid such as aluminum chloride, in relation to 1 mole of the compound represented by general formula (XXXV).

Still further, a compound represented by general formula (X) yields a compound represented by general formula (II) as intended when treated with from 1 to 3 moles of a metal or an organometal compound (the same as defined for Process 3) in from 0.5 to 10 l of a solvent (the same as defined for Process 3) and then reacted with from 1 to 5 moles of sulfur, in relation to 1 mole of the compound represented by general formula (X).

Also, a compound represented by general formula (XVIII) yields a compound represented by general formula (II) as intended after conversion into the diazonium salt as in Process 9 and treatment with from 1 to 3 moles of a xanthate salt or a thiocyanate salt followed by alkali hydrolysis.

Each reaction is carried out at an arbitrary temperature within the range of from $-70°$ C. to the reflux temperature of the reaction system, preferably from $-20°$ C to $100°$ C., and completed in from 10 minutes to 20 hours, depending on the compound.

Further, when $B_2$ is an electron-withdrawing group, $B_4$, a precursor represented by general formula (II-1) is available by substitution reaction.

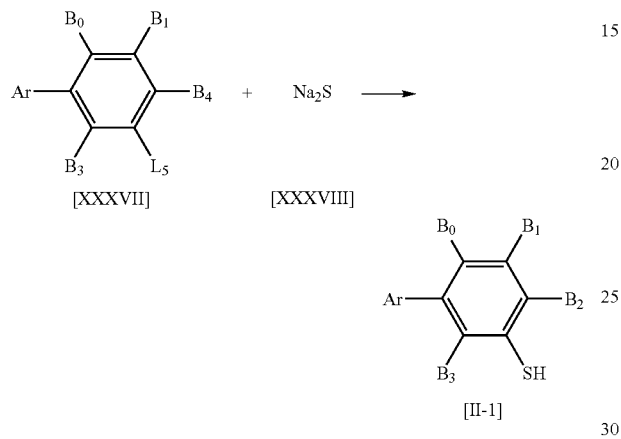

(wherein Ar, $L_5$ and $B_0$ to $B_4$ are the same as defined above.)

That is, a compound represented by general formula (XXXVII) yields a 3-arylphenylthiol represented by general formula (II-1) as intended when reacted with from 1 to 3 moles of sodium sulfate (XXXVIII) in from 0.5 to 10 l of a solvent (the same as defined for Process 1) in the presence of from 1 to 5 moles of a base (the same as defined for Process 1), in relation to 1 mole of the compound represented by general formula (XXXVII), and then neutralized with a mineral acid or the like.

The reaction is carried out at an arbitrary temperature within the range of from $-30°$ C. to the reflux temperature of the reaction system, preferably from $-20°$ C. to $100°$ C., and completed in from 10 minutes to 20 hours, depending on the compound.

Compounds represented by general formulae (X), (XVIII), (XXXIII), (XXXV) and (XXXVII) are obtainable by processes similar to Process 3, Process 4, Process 6, Process 7, Process 10, Process 11 or Process 12, and compounds represented by general formula (X) wherein $Y_1$ is a halogen atom, can obtained by halogenation of the corresponding compound wherein $Y_1$ is a hydrogen.

<Process 15> Synthesis of Precursors Represented by General Formula (XIII)

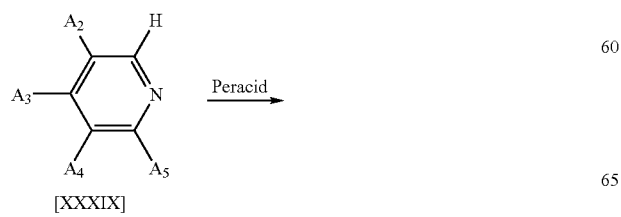

-continued

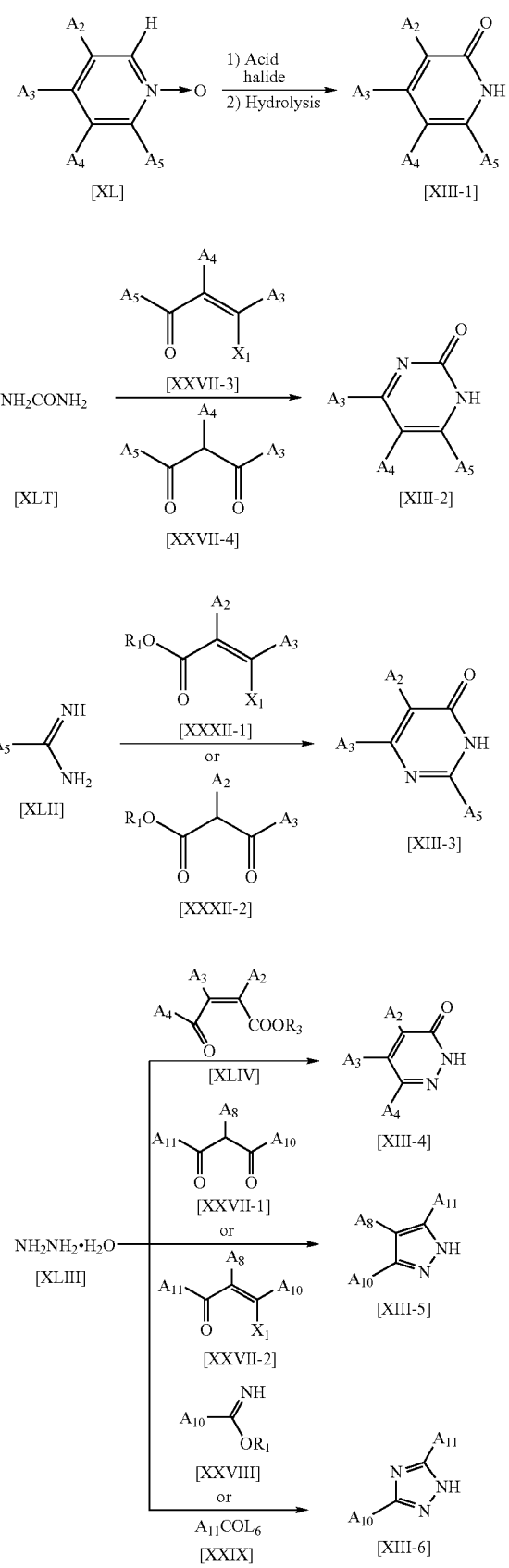

(therein $R_3$ is a hydrogen atom or an alkyl group, and $A_2$ to $A_{11}$, $R_1$, $X_1$ and $L_6$ are the same as defined above.)

That is, a compound represented by general formula (XXXIX) yields a precursor represented by general formula (XIII-1) as intended after oxidization into an N-oxide (XL) with from 1 to 3 moles of a peracid (such as m-chloroperbenzoic acid or peroxysulfuric acid) in from 0.5 to 10 l of a solvent (the same as defined for Process 1) and treatment with from 1 to 5 moles of an acid halide (such as acetyl chloride or phosphorus oxychloride) followed by hydrolysis under alkaline or acidic conditions, in relation to 1 mole of the compound represented by general formula (XXXIX).

Urea (XLI) yields a precursor represented by general formula (XIII-2) as intended when reacted with from 0.5 to 5 moles of a compound represented by general formula (XXVII-3) or a compound represented by general formula (XXVII-4) in from 0.5 to 10 l of a solvent (the same as defined for Process 1) in the presence of from 0.5 to 5 moles of a base (the same as defined for Process 1), in relation to 1 mole of urea (XLI).

A compound represented by general formula (XLII) yields a precursor represented by general formula (XIII-3) as intended when reacted with from 1 to 5 moles of a compound represented by general formula (XXXII-1) or a compound represented by general formula (XXXII-2) in from 0.5 to 10 l of a solvent (the same as defined for Process 1) in the presence of from 1 to 5 moles of a base (the same as defined for Process 1), in relation to 1 mole of the compound represented by general formula (XLII).

Hydrazine hydrate (XLIII) yields a precursor represented by general formula (XIII-4) as intended when reacted with from 0.5 to 5 moles of a compound represented by general formula (XLIV) in from 0.5 to 10 l of a solvent (the same as defined for Process 1), in relation to 1 mole of hydrazine hydrate (XLIII).

Also, hydrazine hydrate (XLIII) yields a precursor represented by general formula (XIII-5) as intended when reacted with from 0.5 to 5 moles of a compound represented by general formula (XXVII-1) or a compound represented by general formula (XXVII-2) in from 0.5 to 10 l of a solvent (the same as defined for Process 1) in the presence of from 0.5 to 5 moles of a base (the same as defined for Process 1), in relation to hydrazine hydrate (XLIII).

Further, hydrazine hydrate (XLIII) yields a precursor represented by general formula (XIII-6) as intended when reacted with from 0.5 to 5 moles of a compound represented by general formula (XXVIII) or a mineral acid salt thereof or a compound represented by general formula (XXIX) in from 0.5 to 10 l of a solvent (the same as defined for Process 1) in the presence of from 0.5 to 5 moles of a base (the same as defined for Process 1) in relation to 1 mole of hydrazine hydrate (XLIII).

Each reaction is carried out at an arbitrary temperature within the range of from −70° C. to the reflux temperature of the reaction system, preferably from −20° C. to 100° C., and completed in from 10 minutes to 20 hours, depending on the compound.

<Process 16> Synthesis of Precursors Represented by General Formula (XXI)

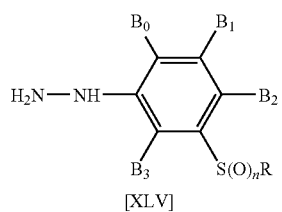

[XLV]

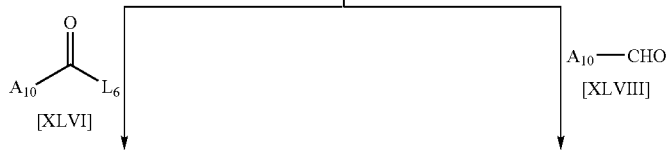

[XLVI] [XLVIII]

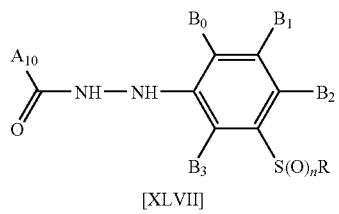
[XLVII]

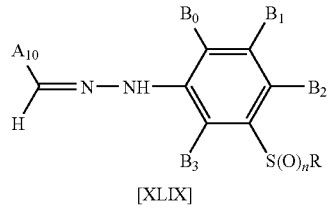
[XLIX]

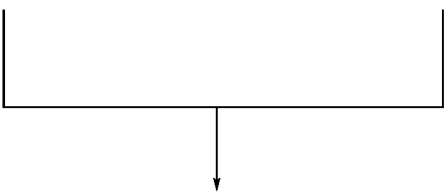

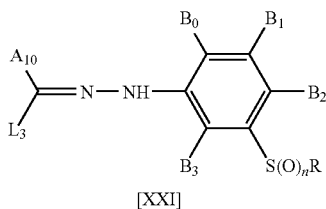
[XXI]

(wherein $L_3$, $L_6$, $A_{10}$, $B_0$ to $B_3$, R and n are as defined above.)

That is, a phenylhydrazine derivative represented by general formula (XLV) yields a compound represented by general formula (XXI) as intended when acylated into a compound represented by general formula (XLVII) with from 1 to 5 moles of a compound represented by general formula (XLVI) in from 0.5 to 10 l of a solvent (the same as defined for Process 1) in the presence of from 1 to 5 moles of a base (the same as defined for Process 1) and then treated with from 1 to 5 moles of a halogenating agent (such as phosphorus trichloride, phosphorus tribromide, thionyl chloride, phosphorus oxychloride, phosphorus pentachloride, triphenylphosphine/carbon tetrachloride or triphenylphosphine/carbon tetrabromide), in relation to 1 mole of the phenylhydrazine derivative represented by general formula (XLV).

Also, a phenylhydrazine derivative represented by general formula (XLV) yields a compound represented by general formula (XXI) as intended when converted into a phenyl hydrazone derivative represented by general formula (XLIX) by treatment with from 1 to 5 moles of an aldehyde derivative or an aldehyde-lower alcohol adduct (an aldehyde hemi-acetal) represented by general formula (XLVIII) in from 0.5 to 10 l of a solvent (the same as defined for Process 3) in the presence or absence of an acid catalyst (such as a sulfonic acid like p-toluenesulfonic acid or a Lewis acid like titanium tetrachloride) and then treated with from 1 to 5 moles of a halogenating agent (such as chlorine, N-chlorosuccinimide, N-bromosuccinimide or tert-butyl hypochlorite).

Each reaction is carried out at an arbitrary temperature within the range of from −70° C. to the reflux temperature of the reaction system, preferably from −20° C. to 150° C., and completed in from 10 minutes to 20 hours, depending on the compound.

EXAMPLES

Now, preparation, formulations and use of the compounds of the present invention will be described in further detail with reference to Examples. Preparations of precursors of the compounds of the present invention will also be described.

Example 1

(1) Preparation of 2-(2-propenylthio)-4-(4-trifluoromethylphenyl)benzonitrile (Compound No. I-42 of the Present Invention)

1.0 g (3.6 mmol) of 2-mercapto-4-(4-trifluoromethylphenyl)benzonitrile, 0.45 g (4.0 mmol) of potassium tert-butoxide and 0.5 g (4.1 mmol) of 3-propenyl bromide were stirred in 20 ml of N,N-dimethylformamide at room temperature for 1 hour. The resulting reaction mixture was poured into 20 ml of water and extracted with 50 ml of ethyl acetate twice. The ethyl acetate layer was washed with 50 ml of water twice and dried over anhydrous magnesium sulfate, and the ethyl acetate was distilled off under reduced pressure. Purification of the residue by silica gel column chromatography afforded 0.5 g of 2-(2-propenylthio)-4-(4-trifluoromethylphenyl)benzonitrile (yield 43.0%) as yellow crystals (m.p. 89-90° C.).

| $^1$H-NMR data (300 MHz, CDCl$_3$ solvent, δ value) ||
|---|---|
| 3.73 | (2H, d) |
| 5.16 | (1H, d) |
| 5.20 | (1H, d) |
| 5.90 | (1H, m) |
| 7.48 | (1H, d) |
| 7.50-7.76 | (6H, m) |

(2) Preparation of 2-cyclobutylmethylthio-4-(3-trifluoromethylpyrazolyl) benzonitrile (Compound No. V-33 of the Present Invention)

0.9 g (3.3 mmol) of 2-mercapto-4-(3-trifluoromethylpyrazolyl)benzonitrile, 0.5 g (3.3 mmol) of cyclobutylmethyl bromide and 0.55 g (4.0 mmol) of potassium carbonate were stirred in 5 ml of N,N-dimethylformamide at room temperature overnight. The resulting reaction mixture was poured into 50 ml of water and the organic matters were extracted with 20 ml of ethyl acetate twice. The ethyl acetate layers were combined, then washed with 30 ml of water twice and dried over anhydrous magnesium sulfate, and the ethyl acetate was distilled off under reduced pressure. Purification of the residue by silica gel column chromatography afforded 0.24 g of 2-cyclobutylmethylthio-4-(3-trifluoromethylpyrazolyl)benzonitrile (yield 21.2%) as a pale yellow powder (m.p. 102-103° C.).

| $^1$H-NMR data (300 MHz, CDCl$_3$ solvent, δ value) | |
| --- | --- |
| 1.84-2.00 | (4H, m) |
| 2.10-2.24 | (2H, m) |
| 2.57-2.67 | (1H, m) |
| 3.18 | (2H, d) |
| 6.79 | (1H, d) |
| 7.53 | (1H, dd) |
| 7.71 | (1H, d) |
| 7.79 | (1H, d) |
| 8.02 | (1H, dd) |

Example 2

(1) Preparation of [5-(2,6-dichloro-4-trifluoromethylphenyl)-2-methylphenyl] isopropyl sulfide (Compound No. I-55 of the Present Invention)

3.3 g (4.9 mmol) of 1,1'-thiodi-[5-(2,6-dichloro-4-trifluoromethylphenyl)-2-methylbenzene], 3.0 g (19.5 mmol) of Rongalite and 3.0 g (17.6 mmol) of isopropyl iodide were stirred in 30 ml of N,N-dimethylformamide at room temperature for 3 hours. The resulting reaction mixture was poured into 300 ml of water and extracted with 50 ml of ethyl acetate twice. The ethyl acetate layer was washed with 50 ml of water twice and dried over anhydrous magnesium sulfate, and the ethyl acetate was distilled off under reduced pressure. Purification of the residue by silica gel column chromatography afforded 1.4 g of [5-(2,6-dichloro-4-trifluoromethylphenyl)-2-methylphenyl] isopropyl sulfide (yield 38.0%) as a yellow dough ($n_D^{20}$ 1.5462).

| $^1$H-NMR data (300 MHz, CDCl$_3$ solvent, δ value) | |
| --- | --- |
| 1.33 | (6H, d) |
| 2.46 | (3H, s) |
| 3.35-3.44 | (1H, m) |
| 6.98-7.02 | (1H, dd) |
| 7.20 | (1H, d) |
| 7.31 | (1H, d) |
| 7.67 | (2H, s) |

(2) Preparation of [2-ethoxymethoxy-5-(4-trifluoromethylphenyl) phenyl] 2,2,2-trifluoroethyl sulfide (Compound No. 1-213 of the Present Invention)

3.3 g (5.0 mmol) of 1,1'-thiodi-[2-ethoxymethoxy-5-(4-trifluoromethylphenyl)benzene], 3.0 g (19.5 mmol) of Rongalite, 3.0 g (21.7 mmol) of potassium carbonate and 3.2 g (17.6 mmol) of 2,2,2-trifluoroethyl iodide were stirred in 50 ml of N,N-dimethylformamide at room temperature for 3 hours. The resulting reaction mixture was poured into 300 ml of water and extracted with 50 ml of ethyl acetate twice. The ethyl acetate layer was washed with 50 ml of water twice and dried over anhydrous magnesium sulfate, and the ethyl acetate was distilled off under reduced pressure. Purification of the residue by silica gel column chromatography afforded 3.1 g of [2-ethoxymethoxy-5-(4-trifluoromethylphenyl)phenyl] 2,2,2-trifluoroethyl sulfide (yield 75.6%) as a pale yellow viscous liquid ($n_D^{20}$ 1.5213).

(3) Preparation of 2-(2,2,2-trifluoroethylthio)-4-(3-trifluoromethylpyrazolyl)benzonitrile (Compound No. V-27 of the Present Invention)

2.7 g (5.0 mmol) of 1,1'-thiodi-[2-cyano-5-(3-trifluoromethylpyrazolyl)benzene], 3.0 g (19.5 mmol) of Rongalite, 3.0 g (21.7 mmol) of potassium carbonate and 6.1 g (29.0 mmol) of 2,2,2-trifluoroethyl iodide were stirred in 50 ml of N,N-dimethylformamide at room temperature for 3 hours. The resulting reaction mixture was poured into 300 ml of water and extracted with 50 ml of ethyl acetate twice. The ethyl acetate layer was washed with 50 ml of water twice and dried over anhydrous magnesium sulfate, and the ethyl acetate was distilled off under reduced pressure. Purification of the residue by silica gel column chromatography afforded 2.5 g of 2-(2,2,2-trifluoroethylthio)-4-(3-trifluoromethylpyrazolyl)benzonitrile (yield 71.4%) as a brown solid (m.p. 65-67° C.).

(4) Preparation of [2-chloro-4-fluoro-5-(3-trifluoromethyltriazolyl)phenyl] 2,2,2-trifluoroethyl sulfide (Compound No. VI-291 of the Present Invention)

1.8 g (3.0 mmol) of 1,1'-thiodi-[2-chloro-4-fluoro-5-(3-trifluoromethyltriazolyl)benzene], 2.0 g (13.0 mmol) of Rongalite, 2.0 g (14.5 mmol) of potassium carbonate and 3.2 g (17.6 mmol) of 2,2,2-trifluoroethyl iodide were reacted in the same way as in Example 2 (3) and afforded 1.1 g of [2-chloro-4-fluoro-5-(3-trifluoromethyltriazolyl)phenyl] 2,2,2-trifluoroethyl sulfide (yield 47.8%) as white crystals (m.p. 56-58° C.).

| $^1$H-NMR data (300 MHz, CDCl$_3$ solvent, δ value) | |
| --- | --- |
| 3.30 | (2H, q) |
| 7.76 | (1Hdd) |
| 7.50 | (1H, d) |
| 8.18 | (1H, d) |
| 8.72 | (1H, s) |

Example 3

Preparation of [3-(2,6-dichloro-4-trifluoromethylphenyl)phenyl] isopropyl sulfide (Compound No. I-73 of the Present Invention)

1.0 g (3.6 mmol) of 3-iodophenyl isopropyl sulfide was stirred in 10 ml of dry benzene in a nitrogen stream at room temperature, while 2.8 ml of a n-butyllithium solution in hexane (1.56 mol/l) was added dropwise. The resulting reaction mixture was stirred at room temperature for another 2 hours and cooled to 10° C., and 1.0 g (4.3 mmol) of 3,5-dichloro-4-fluorobenzotrifluoride in 50 ml of diethyl ether was added dropwise. The resulting reaction mixture was stirred at room temperature for further 12 hours and poured into 100 ml of water for separation. The organic layer was washed with 50 ml of water twice and dried over anhydrous magnesium sulfate, and the solvent was distilled off under reduced pressure. Purification of the residue by silica gel column chromatography afforded 0.5 g of [3-(2,6-dichloro-4-trifluoromethylphenyl)phenyl] isopropyl sulfide (yield 38.0%) as a colorless liquid ($n_D^{20}$ 1.5675).

| $^1$H-NMR data (300 MHz, CDCl$_3$ solvent, δ value) | |
|---|---|
| 1.32 | (6H, d) |
| 3.34-3.48 | (1H, m) |
| 7.11-7.12 | (1H, m) |
| 7.26-7.27 | (1H, d) |
| 7.40-7.49 | (2H, m) |
| 7.67 | (2H, s) |

Example 4

Preparation of [3-(4-trifluoromethylphenyl)phenyl]Cyclopentyl sulfide (Compound No. I-67 of the Present Invention)

1.0 g (5.2 mmol) of 4-trifluoromethylphenyl boronic acid, 1.4 g (5.4 mmol) of 3-bromophenyl cyclopentyl sulfide, 1.6 g (15.0 mmol) of sodium carbonate and 0.8 g (0.7 mmol) of tetrakis(triphenylphosphine) palladium were added to a solvent mixture of 50 ml of toluene, 25 ml of ethanol and 25 ml of water and refluxed under heating and stirring for 2 hours. The resulting reaction mixture was poured into ice-cold water and extracted with toluene. The toluene layer was washed with water twice and dried over anhydrous magnesium sulfate, and the solvent was distilled off under reduced pressure. Purification of the residue by silica gel column chromatography afforded 1.3 g of [3-(4-trifluoromethylphenyl)phenyl]cyclopentyl sulfide (yield 78.0%) as a colorless liquid ($n_D^{20}$ 1.5732).

| $^1$H-NMR data (300 MHz, CDCl$_3$ solvent, δ value) | |
|---|---|
| 1.54-1.75 | (4H, m) |
| 1.76-1.85 | (2H, m) |
| 2.03-2.14 | (2H, m) |
| 3.61-3.87 | (1H, m) |
| 7.38-7.96 | (8H, m) |

Example 5

Preparation of [5-(4-trifluoromethylphenyl)-2-ethoxymethoxyphenyl] propyl sulfide (Compound No. I-212 of the Present Invention)

3.0 g (10.1 mmol) of 4-(4-trifluoromethylphenyl)phenyl ethoxymethyl ether dissolved in 30 ml of diethyl ether was stirred at −20° C. while 7.8 ml of a n-butyllithium solution in hexane (1.56 mol/l) was added dropwise. The resulting reaction mixture was stirred at room temperature for another 2 hours and cooled to 0° C., and 1.8 g (12.0 mmol) of dipropyl disulfide was added dropwise. The resulting reaction mixture was stirred at room temperature for further 2 hours and poured into ice-cold water. The ether layer was washed with water twice and dried over anhydrous magnesium sulfate, and the solvent was distilled off under reduced pressure. Purification of the residue by silica gel column chromatography afforded 2.6 g of [5-(4-trifluoromethylphenyl)-2-ethoxymethoxyphenyl] propyl sulfide (yield 69.5%) as a yellow viscous liquid ($n_D^{20}$ 1.5491).

Example 6

Preparation of 2-propylthio-4-(3-trifluoromethyl-1H-triazolyl)benzonitrile (Compound No. VI-1 of the Present Invention) 1.06 g (7.7 mmol) of 3-trifluoromethyl-1H-triazol, 1.38 g (6.5 mmol) of 4-chloro-2-n-propylthiobenzonitrile and 1.07 g (7.7 mmol) of potassium carbonate were stirred in 10 ml of N,N-dimethylformamide at 150° C. for 2 hours. The resulting reaction mixture was cooled to the room temperature and poured into 100 ml of water, and the organic matters were extracted with 50 ml of ethyl acetate twice. The ethyl acetate layers were combined, then washed with 50 ml of water twice and dried over anhydrous magnesium sulfate, and the solvent was distilled off under reduced pressure. Purification of the residue by silica gel column chromatography afforded 0.78 g of 2-propylthio-4-(3-trifluoromethyl-1H-triazolyl)benzonitrile (yield 38.2%) as a milk-white powder (m.p. 143-144° C.).

| $^1$H-NMR data (300 MHz, CDCl$_3$ solvent, δ value) | |
|---|---|
| 1.84-2.00 | (4H, m) |
| 1.12 | (3H, t) |
| 1.80 | (2H, h) |
| 3.11 | (2H, t) |
| 7.53 | (1Hdd) |
| 7.75 | (1H, d) |
| 7.77 | (1H, d) |
| 8.69 | (1H, s) |

Example 7

Preparation of [4-fluoro-2methyl-5-(3-trifluoromethylpyrazolyl)phenyl] 2,2,2trifluoroetyl sulfide (Compound No. V-613 of the Present Invention)

0.34 g (2.49 mmol) of 1H-3-trifluoromethylpyrazol, 1.34 g (5.0 mmol) of 2-fluoro-4-methyl-5-(2,2,2trifluoroethylthio) benzeneboronic acid, 0.39 g (4.98 mmol) of pyridine, 0.68 g (3.74 mmol) of copper acetate (II) and 0.1 g of a 4 Å-molecular sieves were stirred in 20 ml of methylene chloride at room temperature for 2 days, and the solvent was distilled off under reduced pressure. Purification of the residue by silica gel column chromatography afforded 0.09 g of [4-fluoro-2methyl-5-(3-trifluoromethylpyrazolyl)phenyl]2,2,2trifluoroethyl sulfide (yield 10.0%) as a pale yellow liquid ($n_D^{20}$ 1.4998).

| $^1$H-NMR data (300 MHz, CDCl$_3$ solvent, δ value) | |
|---|---|
| 2.52 | (3H, s) |
| 3.43 | (2H, q) |
| 6.74 | (1H, d) |
| 7.15 | (1H, d) |
| 7.99 | (1H, bs) |
| 8.05 | (1H, d) |

Example 8

(1) Preparation of 4-(2,4-dichlorophenyl)-2-ethylthiobenzonitrile (Compound No. I-62 of the Present Invention)

0.12 g (3.0 mmol) of 60% sodium hydride was stirred in 30 ml of N,N-dimethylformamide at room temperature while 0.2 g (3.2 mmol) of ethanethiol was added dropwise. After generation of hydrogen was over, 0.7 g (2.6 mmol) of 2-fluoro-4-(2,4-dichlorophenyl)benzonitrile was added, and the reaction mixture was stirred at 60° C. for 6 hours. The reaction mixture was poured into about 100 ml of ice-cold water and extracted with 50 ml of ethyl acetate twice. The ethyl acetate layer was washed with 50 ml of water twice and dried over anhydrous magnesium sulfate, and the ethyl acetate was distilled off under reduced pressure. Purification of the residue by silica gel column chromatography afforded 0.7 g of 4-(2,4-dichlorophenyl)-2-ethylthiobenzonitrile (yield 88.0%) as pale yellow crystals (m.p. 89-92° C.).

| $^1$H-NMR data (300 MHz, CDCl$_3$ solvent, δ value) | |
| --- | --- |
| 1.38 | (3H, t) |
| 3.07 | (2H, q) |
| 7.25-7.42 | (3H, m) |
| 7.49 | (1H, dd) |
| 7.52 | (1H, dd) |
| 7.76 | (1H, d) |

(2) Preparation of [5-(2,6-dichloro-4-trifluoromethylphenyl)-2-nitrophenyl] isopropyl sulfide (Compound No. I-56 of the Present Invention)

0.33 g (8.3 mmol) of 60% sodium hydride was stirred in 50 ml of N,N-dimethylformamide at room temperature while 0.7 g (9.2 mmol) of isopropyl mercaptan was added dropwise. After generation of hydrogen was over, 3.0 g (8.1 mmol) of 1-chloro-5-(2,6-dichloro-4-trifluoromethylphenyl)-2-nitrobenzene was added, and the reaction mixture was stirred at room temperature for 12 hours. The reaction mixture was poured into about 200 ml of ice-cold water and extracted with 50 ml of ethyl acetate twice. The ethyl acetate was washed with 100 ml of water twice and dried over anhydrous magnesium sulfate, and the ethyl acetate was distilled off under reduced pressure. Purification of the residue by silica gel column chromatography afforded 3.0 g of [5-(2,6-dichloro-4-trifluoromethylphenyl)-2-nitrophenyl] isopropyl sulfide (yield 90.0%) as a yellow dough ($n_D^{20}$ 1.5881).

| $^1$H-NMR data (300 MHz, CDCl$_3$ solvent, δ value) | |
| --- | --- |
| 1.40 | (6H, d) |
| 3.50-3.59 | (1H, m) |
| 7.12-7.13 | (1H, dd) |
| 7.31 | (1H, d) |
| 7.67 | (2H, s) |
| 8.25 | (1H, d) |

(3) Preparation of [4-fluoro-2-nitro-5-(4-trifluoromethylphenyl)phenyl] propyl sulfide (Compound No. I-221 of the Present Invention)

To 1.4 g (12.5 mmol) of potassium tert-butoxide in 100 ml of tetrahydrofuran, 0.9 g (11.8 mmol) of n-pronanethiol was added dropwise at room temperature, and the resulting reaction mixture was stirred at the same temperature for 10 minutes. 3.5 g (11.6 mmol) of 4-(4-trifluoromethylphenyl)-2,5-difluoronitrobenzene was added dropwise, and the reaction mixture was stirred at room temperature for further 2 hours. The tetrahydrofuran was distilled off under reduced pressure, and after addition of 200 ml of ice-cold water, the organic matters were extracted with 50 ml of ethyl acetate twice. The ethyl acetate layers were combined, washed with 100 ml of water twice and dried over anhydrous magnesium sulfate, and the ethyl acetate was distilled off under reduced pressure. Purification of the residue by silica gel column chromatography afforded 3.8 g of [4-fluoro-2-nitro-5-(4-trifluoromethylphenyl)phenyl] propyl sulfide (yield 90%) as yellow crystals (m.p. 57-59° C.).

| $^1$H-NMR data (300 MHz, CDCl$_3$ solvent, δ value) | |
| --- | --- |
| 1.11 | (3H, t) |
| 1.81 | (2H, m) |
| 2.97 | (2H, t) |
| 7.42 | (1H, d) |
| 7.56 | (2H, d) |
| 7.81 | (2H, d) |
| 8.08 | (1H, d) |

(4) Preparation of 2-cyclopropylmethylthio-4-(5-trifluoromethylpyridin-2-yl)benzonitrile (Compound No. II-5 of the Present Invention)

1.8 g (6.8 mmol) of 4-(5-trifluoromethylpyridin-2-yl)-2-fluorobenzonitrile, 1.6 g (7.6 mmol) of S-cyclopropylmethylisothiourea hydrobromide salt and 50 ml of N,N-dimethylformamide were put into a round-bottomed flask and stirred together with 1.6 g (8 mmol) of 20% aqueous sodium hydroxide overnight. The solvent was distilled off under reduced pressure, and the reaction mixture was separated with 50 ml of water and 50 ml of ethyl acetate. The organic layer was washed with 50 ml of water twice and dried over anhydrous magnesium sulfate, and the solvent was distilled off under reduced pressure to obtain 2.2 g of 2-cyclopropylmethylthio-4-(5-trifluoromethylpyridin-2-yl)benzonitrile (yield 96%) as pale yellow feathery crystals (m.p. 135-136° C.).

| $^1$H-NMR data (300 MHz, CDCl$_3$ solvent, δ value) | |
| --- | --- |
| 0.29-0.35 | (2H, m) |
| 0.61-0.68 | (2H, m) |
| 1.07-1.20 | (1H, m) |
| 3.07 | (2H, d) |
| 7.75 | (1H, d) |
| 7.85-7.90 | (2H, m) |
| 8.05 | (1H, dd) |
| 8.19 | (1H, d) |
| 8.99 | (1H, dd) |

(5) Preparation of 4-(6-oxo-4-trifluoromethyl-1,6-dihydropyrimidin-1-yl)-2-propylthibenzonitrile (Compound No. III-9 of the Present Invention)

1.1 g (3.9 mmol) of 4-(6-oxo-4-trifluoromethyl-1,6-dihydropyrimidin-1-yl)-2-fluorobenzonitrile dissolved in 50 ml of dimethyl sulfoxide was allowed to react with 1.0 g (7.2 mmol) of potassium carbonate and 0.3 g (3.9 mmol) of propanethiol at 100° C. for 2 hours. The solvent was distilled off under reduced pressure, and the reaction mixture was separated with 50 ml of water and 50 ml of ethyl acetate. The organic layer was washed with 50 ml of water twice and dried over anhydrous magnesium sulfate, and the ethyl acetate was distilled off under reduced pressure. Purification of the residue by silica gel column chromatography afforded 0.7 g of 4-(6-oxo-4-trifluoromethyl-1,6-dihydropyrimidin-1-yl)-2-propylthibenzonitrile (yield 54%) as a white powder (m.p. 157-158° C.).

| $^1$H-NMR data (300 MHz, CDCl$_3$ solvent, δ value) | |
|---|---|
| 1.09 | (3H, t) |
| 1.77 | (2H, m) |
| 3.03 | (2H, t) |
| 6.96 | (1H, s) |
| 7.22 | (1H, dd) |
| 7.35 | (1H, d) |
| 7.79 | (1H, d) |
| 8.25 | (1H, s) |

(6) Preparation of 4-(5-chlorothiophen-2-yl)-2-cyclopropylmethylthiobenzonitrile (Compound No. IV-5 of the Present Invention)

0.9 g (4.0 mmol) of 4-(5-chlorothiophen-2-yl)-2-fluorobenzonitrile and 0.9 g (4.3 mmol) of S-cyclopropylmethylisothiourea hydrobromide were allowed to react in the same manner as described above in Example 8 (4), and purification of the crude product by silica gel column chromatography afforded 1.1 g of 4-(5-chlorothiophen-2-yl)-2-cyclopropylmethylthiobenzonitrile (yield 91%) as yellow feathery crystals (m.p. 123-124° C.).

| $^1$H-NMR data (300 MHz, CDCl$_3$ solvent, δ value) | |
|---|---|
| 0.28-0.33 | (2H, m) |
| 0.61-0.67 | (2H, m) |
| 1.07-1.15 | (1H, m) |
| 3.00 | (2H, d) |
| 6.95 | (1H, d) |
| 7.19 | (1H, d) |
| 7.36 | (1H, dd) |
| 7.54 | (1H, d) |
| 7.60 | (1H, dd) |

(7) Preparation of [2-nitro-5-(3-trifluoromethylpyrazolyl)phenyl] propyl sulfide (Compound No. V-166 of the Present Invention)

0.8 g (2.7 mmol) of 1-(3-chloro-4-nitrophenyl)-3-trifluoromethylpyrazol, 0.25 g (3.3 mmol) of 1-propanethiol and 0.57 g (4.1 mmol) of potassium carbonate were stirred in 5 ml of N,N-dimethylformamide at room temperature for 2 hours. The resulting reaction mixture was poured into 50 ml of water, and the organic matters were extracted with 20 ml of ethyl acetate twice. The ethyl acetate layers were combined, washed with 30 ml of water twice and dried over anhydrous magnesium sulfate, and the ethyl acetate was distilled off under reduced pressure. Purification of the residue by silica gel column chromatography afforded 0.31 g of [2-nitro-5-(3-trifluoromethylpyrazolyl)phenyl] propyl sulfide (yield 34.4%) as an amber viscous liquid ($n_D^{20}$ 1.5741).

| $^1$H-NMR data (300 MHz, CDCl$_3$ solvent, δ value) | |
|---|---|
| 1.08 | (3H, t) |
| 1.75 | (2H, h) |
| 3.02 | (2H, t) |
| 6.74 | (1H, d) |
| 7.37-7.40 | (2H, m) |
| 7.72 | (1Hdd) |
| 7.97 | (1H, d) |

(8) Preparation of 2-(2,2,2-trifluoroethylthio)-4-(4-trifluoromethylpyrazolyl)benzonitrile (Compound No. V-639 of the Present Invention)

0.65 g (2.4 mmol) of 2-chloro-4-(4-trifluoromethylpyrazolyl)benzonitrile, 0.33 g (2.9 mmol) of 2,2,2-trifluoroethanthiol and 0.40 g (2.9 mmol) of potassium carbonate were stirred in 5 ml of N,N-dimethylformamide at room temperature overnight. The resulting reaction mixture was poured into 50 ml of water, and the organic matters were extracted with 20 ml of ethyl acetate twice. The ethyl acetate layers were combined, washed with 30 ml of water twice and dried over anhydrous magnesium sulfate, and the ethyl acetate was distilled off under reduced pressure. Purification of the residue by silica gel column chromatography afforded 0.48 g of 2-(2,2,2-trifluoroethylthio)-4-(4-trifluoromethylpyrazolyl) benzonitrile (yield 57.1%) as a milk-white powder (m.p. 90-91° C.).

| $^1$H-NMR data (300 MHz, CDCl$_3$ solvent, δ value) | |
|---|---|
| 3.67 | (2H, q) |
| 7.76 | (1Hdd) |
| 7.83 | (1H, d) |
| 7.79 | (1H, s) |
| 8.08 | (1H, d) |
| 8.28 | (1H, s) |

(9) Preparation of 4-(4-methyl-3-trifluoromethylpyrazolyl)-2-propylthiobenzaldehyde (Compound No. V-381 of the Present Invention)

5.77 g (20.0 mmol) of 2-chloro-4-(4-methyl-3-trifluoromethylpyrazolyl)benzaldehyde, 1.83 g (23.9 mmol) of 1-propanethiol and 3.31 g (24.0 mmol) of potassium carbonate were stirred in 20 ml of N,N-dimethylformamide at room temperature overnight. The resulting reaction mixture was poured into 200 ml of water, and the organic matters were extracted with 100 ml of ethyl acetate twice. The ethyl acetate layers were combined, washed with 100 ml of water twice and dried over anhydrous magnesium sulfate, and the ethyl acetate was distilled off under reduced pressure. Purification of the residue by silica gel column chromatography afforded 3.07 g of 4-(4-methyl-3-trifluoromethylpyrazolyl)-2-propylthiobenzaldehyde (yield 46.8%) as a yellow liquid ($n_D^{20}$ 1.5726).

| $^1$H-NMR data (300 MHz, CDCl$_3$ solvent, δ value) | |
|---|---|
| 1.11 | (3H, t) |
| 1.79 | (2H, h) |
| 2.26 | (3H, s) |
| 3.03 | (2H, t) |
| 7.51 | (1H, dd) |
| 7.79 | (1H, d) |
| 7.83 | (1H, s) |
| 7.92 | (1H, d) |
| 10.35 | (1H, s) |

(10) Preparation of methyl 2-propylthio-4-(3-trifluoromethylpyrazolyl)benzoate (Compound No. V-175 of the Present Invention)

1.52 g (5.0 mmol) of methyl 2-chloro-4-(3-trifluoromethylpyrazolyl)benzoate, 0.66 g (8.6 mmol) of 1-propanethiol and 0.83 g (6.0 mmol) of potassium carbonate were stirred in 5 ml of N,N-dimethylformamide at 60° C. for 24 hours. The resulting reaction mixture was poured into 50 ml of water, and the organic matters were extracted with 20 ml of ethyl acetate twice. The ethyl acetate layers were combined, washed with 30 ml of water twice and dried over anhydrous magnesium sulfate, and the ethyl acetate was distilled off under reduced pressure. Purification of the residue by thin layer chromatography afforded 0.31 g of methyl 2-propylthio-4-(3-trifluoromethylpyrazolyl)benzoate as a white powder (m.p. 114-116° C.).

| $^1$H-NMR data (300 MHz, CDCl$_3$ solvent, δ value) | |
|---|---|
| 1.14 | (3H, t) |
| 1.83 | (2H, h) |
| 3.00 | (2H, t) |
| 3.94 | (3H, s) |
| 6.77 | (1H, d) |
| 7.40 | (1H, dd) |
| 7.73 | (1H, d) |
| 8.01 | (1H, bs) |
| 8.10 | (1H, d) |

Example 9

Preparation of [3-(2,4-dichlorophenyl)phenyl] isopropyl sulfide (Compound No. I-71 of the Present Invention)

To 0.9 g (3.8 mmol) of 3-(2,4-dichlorophenyl)aniline and 0.6 g (4.0 mmol) of diisopropyl disulfide in 20 ml of acetonitrile, 0.4 g (4.0 mmol) of tert-butyl nitrite was added dropwise at 60° C. The reaction mixture was stirred at the same temperature for 1 hour, and the low-boiling matters were distilled off under reduced pressure, the residue was separated with water and ethyl acetate. The ethyl acetate layer was washed with water and dried over anhydrous magnesium sulfate, and the ethyl acetate was distilled off under reduced pressure. Purification of the residue by silica gel column chromatography afforded 0.25 g of [3-(2,4-dichlorophenyl)phenyl] isopropyl sulfide (yield 31.0%) as a colorless liquid ($n_D^{20}$ 1.6143).

| $^1$H-NMR data (300 MHz, CDCl$_3$ solvent, δ value) | |
|---|---|
| 1.35 | (6H, d) |
| 3.35-3.49 | (1H, m) |
| 7.19-7.52 | (7H, m) |

Example 10

Preparation of [2-methyl-5-(3-trifluoromethylpyrazolyl)phenyl] propyl sulfide (Compound No. V-176 of the Present Invention)

1.0 g (3.2 mmol) of N'-(4-methyl-3-n-propylthiophenyl) trifluoroacetohydrazidoyl chloride was stirred in 5 ml of N,N-dimethylformamide at 0° C., then mixed with 0.72 g (7.1 mmol) of triethylamine and 1.7 g (15.9 mmol) of vinyl bromide and stirred at 0° C. from room temperature for 24 hours. The resulting reaction mixture was poured into 50 ml of water, and the organic matters were extracted with 20 ml of ethyl acetate twice. The ethyl acetate layers were combined, washed with 30 ml of water twice and dried over anhydrous magnesium sulfate, and the ethyl acetate was distilled off under reduced pressure. Purification of the residue by silica gel column chromatography afforded 0.22 g of [2-methyl-5-(3-trifluoromethylpyrazolyl)phenyl] propyl sulfide (yield 22.7%) as a colorless liquid ($n_D^{20}$ unmeasurable).

| $^1$H-NMR data (300 MHz, CDCl$_3$ solvent, δ value) | |
|---|---|
| 1.08 | (3H, t) |
| 1.75 | (2H, h) |
| 2.38 | (3H, s) |
| 2.97 | (2H, t) |
| 6.71 | (1H, d) |
| 7.23 | (1H, d) |
| 7.32 | (1H, dd) |
| 7.57 | (1H, d) |
| 7.89 | (1H, bs) |

Example 11

Preparation of 2-propylthio-4-(5-trifluoromethylpyrazolyl) benzonitrile (Compound No. V-153 of the Present Invention)

1.7 g (10.1 mmol) of 4-ethoxy-1,1,1-trifluoro-3-buten-2-one and 2.1 g (10.1 mmol) of 4-hydrazino-2-propylthibenzonitrile were added to 50 ml of ethanol and refluxed under heating and stirring for 2 hours. The ethanol was distilled off under reduced pressure, and the residue was refluxed under heating and stirring for another 6 hours after addition of 60 ml of acetic acid. The acetic acid was distilled off under reduced pressure, the residue was separated with ethyl acetate and water. The organic layer was washed with water twice and dried over anhydrous magnesium sulfate, and the solvent was distilled off under reduced pressure. Purification of the residue by silica gel column chromatography afforded 1.2 g of 2-propylthio-4-(5-trifluoromethylpyrazolyl)benzonitrile (yield 38.7%) as a tawny viscous liquid ($n_D^{20}$ 1.5562).

| $^1$H-NMR data (300 MHz, CDCl$_3$ solvent, δ value) | |
|---|---|
| 1.08 | (3H, t) |
| 1.70-1.82 | (2H, m) |
| 3.03 | (2H, t) |
| 6.90 | (1H, d) |
| 7.39 | (1H, dd) |
| 7.52 | (1H, d) |
| 7.72 | (1H, d) |
| 7.78 | (1H, d) |

Example 12

(1) Preparation of [3-(2,4-dichlorophenyl)phenyl]isopropyl sulfoxide (Compound No. I-72 of the Present Invention)

To 1.0 g (3.4 mmol) of [3-(2,4-dichlorophenyl)phenyl] isopropyl sulfide in 50 ml of chloroform, 0.7 g (4.1 mmol) of m-chloroperbenzoic acid was added at 0° C. with stirring, and the reaction mixture was stirred for 2 hours. The reaction mixture was stirred at room temperature for another 12 hours, and 5% aqueous sodium bicarbonate was added for separation. The chloroform layer was washed with 5% aqueous sodium sulfite and water and dried over anhydrous magnesium sulfate, and the solvent was distilled off under reduced pressure. Purification of the residue by silica gel column chromatography afforded 0.9 g of [3-(2,4-dichlorophenyl) phenyl] isopropyl sulfoxide (yield 85.0%) as a colorless dough ($n_D^{20}$ 1.6169).

| $^1$H-NMR data (300 MHz, CDCl$_3$ solvent, δ value) | |
|---|---|
| 1.22 | (6H, dd) |
| 2.79-2.96 | (1H, m) |
| 7.26-7.65 | (7H, m) |

(2) Preparation of [2-difluoromethyl-5-(3-trifluoromethylpyrazolyl)phenyl] 2,2,2-trifluoroethyl sulfoxide (Compound No. V-324 of the Present Invention)

To 0.37 g (1.0 mmol) of [2-difluoromethyl-5-(3-trifluoromethylpyrazolyl)phenyl] 2,2,2-trifluoroethyl sulfide (Compound No. V-295 of the present invention) in 5 ml of chloroform, 0.25 g (1.5 mmol) of m-chloroperbenzoic acid was added at 0° C. with stirring, and the reaction solution was stirred for 1 hour. The reaction solution was mixed with 10 ml of 10% aqueous sodium sulfite and stirred at room temperature for 10 minutes, and then 20 ml of chloroform was added. The chloroform layer was washed with 20 ml of saturated aqueous sodium hydrogen carbonate three times and dried over anhydrous magnesium sulfate, and the chloroform was distilled off under reduced pressure to obtain 0.38 g of [2-difluoromethyl-5-(3-trifluoromethylpyrazolyl)phenyl] 2,2,2-trifluoroethyl sulfoxide (yield 97.4%) as a yellow dough ($n_D^2$ 1.4909).

| $^1$H-NMR data (300 MHz, CDCl$_3$ solvent, δ value) | |
|---|---|
| 3.48-3.67 | (2H, m) |
| 6.82 | (1H, d) |
| 6.96 | (1H, t) |
| 7.81 | (1H, dd) |
| 8.15 | (1H, d) |
| 8.16 | (1H, d) |
| 8.51 | (1H, d) |

(3) Preparation of [2-methyl-5-(3-trifluoromethylpyrazolyl)phenyl] 2,2,2-trifluoroethyl sulfoxide (Compound No. V-321 of the Present Invention)

To 1.68 g (4.9 mmol) of [2-methyl-5-(3-trifluoromethylpyrazolyl)phenyl] 2,2,2-trifluoroethyl sulfide (Compound No. V-292 of the present invention) in 5 ml of chloroform, 1.02 g (5.1 mmol) of m-chlotoperbenzoic acid was added at 0° C. with stirring, and the reaction mixture was stirred at 0° C. for 1 hour. The reaction solution was mixed with 10 ml of 10% aqueous sodium sulfite and stirred at room temperature for 10 minutes, and then 20 ml of chloroform was added. The chloroform layer was washed with 20 ml of saturated aqueous sodium hydrogen carbonate three times and dried over anhydrous magnesium sulfate, and the chloroform was distilled off under reduced pressure to obtain 0.65 g of [2-methyl-5-(3-trifluoromethylpyrazolyl)phenyl] 2,2,2-trifluoroethyl sulfoxide (yield 37.1%) as a pale yellow solid (m.p. 109-110° C.).

| $^1$H-NMR data (300 MHz, CDCl$_3$ solvent, δ value) | |
|---|---|
| 2.44 | (3H, s) |
| 3.46-3.50 | (2H, m) |
| 6.76 | (1H, d) |
| 7.41 | (1H, d) |
| 7.94 | (1H, dd) |
| 8.07 | (1H, d) |
| 8.25 | (1H, d) |

Example 13

Preparation of 4-(2,6-dichloro-4-trifluoromethylphenyl)-2-isopropylthioaniline (compound No. I-57 of the Present Invention)

3.5 g (63.6 mmol) of iron powder, 10 m of water and 1 m of acetic acid were stirred in 20 ml toluene at 60° C. for 30 minutes, and 3.0 g (7.3 mmol) of [5-(2,6-dichloro-4-trifluoromethylphenyl)-2-nitrophenyl] isopropyl sulfide (the compound prepared in Example 8 (2)) in 10 ml toluene was added dropwise. The reaction was carried out with reflux and heating for another 3 hours, and then the reaction mixture was cooled to room temperature. The insolubles were filtered off, and the filtrate was separated with water and toluene. The toluene layer was washed with water and dried over anhydrous magnesium sulfate, and the solvent was distilled off under reduced pressure. Purification of the residue by silica gel column chromatography afforded 1.0 g of 4-(2,6-dichloro-4-trifluoromethylphenyl)-2-isopropylthioaniline (yield 36.0%) as a pale yellow dough ($n_D^{20}$ 1.5782).

| $^1$H-NMR data (300 MHz, CDCl$_3$ solvent, δ value) | |
|---|---|
| 1.27 | (6H, d) |
| 3.20-3.34 | (1H, m) |
| 6.82 | (1H, d) |
| 7.00-7.04 | (1H, dd) |
| 7.27 | (1H, d) |
| 7.67 | (2H, s) |

Example 14

Preparation of [5-(2,6-dichloro-4-trifluoromethylphenyl)-2-bromophenyl] isopropyl sulfide (Compound No. I-58 of the Present Invention)

To 0.7 g (1.8 mmol) of 5-(2,6-dichloro-4-trifluoromethylphenyl)-2-isopropylthioaniline (the compound prepared in Example 9) and 0.5 g (3.5 mmol) of copper bromide in 20 m of acetonitrile, 0.2 g (2.0 mmol) tert-butyl nitrite was added dropwise at 60° C. After 1 hour of stirring at the same temperature, the low-boiling matters were distilled off under reduced pressure, and the reaction mixture was separated with water and ethyl acetate. The ethyl acetate layer was washed with water and dried over anhydrous magnesium sulfate, and the solvent was distilled off under reduced pressure. Purification of the residue by silica gel column chromatography afforded 0.25 g of [5-(2,6-dichloro-4-trifluoromethylphenyl)-2-bromophenyl] isopropyl sulfide (yield 31.0%) as a colorless liquid ($n_D^{20}$ 1.5642).

| $^1$H-NMR data (300 MHz, CDCl$_3$ solvent, δ value) | |
|---|---|
| 1.37 | (6H, d) |
| 3.49 | (1H, q) |
| 6.93 | (1H, dd) |
| 7.18 | (1H, d) |
| 7.68 | (2H, s) |
| 7.69 | (1H, d) |

Example 15

Preparation of [2-methyl-5-(3-trifluoromethylpyrazolyl)phenyl] propyl sulfide (Compound No. V-176 of the Present Invention)

0.98 g (3.1 mmol) of 2-propylthio-4-(3-trifluoromethylpyrazolyl)benzaldehyde (Compound No. V-159 of the present invention) prepared in the same manner as in Example 8 (9) was dissolved in 10 ml of methylene chloride and stirred together with 1.44 g (12.4 mmol) of triethylsilane and 0.63 ml (6.8 mmol) of boron trifluoride diethyl ether complex at room temperature for 22 hours. The reaction mixture was poured into 50 ml of ice-cold water, and 20 ml of methylene chloride was added. The methylene chloride layer was separated, washed with 30 ml of water twice and dried over anhydrous magnesium sulfate, and the methylene chloride was distilled off under reduced pressure. Purification of the residue by silica gel column chromatography afforded 0.18 g of [2-methyl-5-(3-trifluoromethylpyrazolyl)phenyl] propyl sulfide (yield 19.3%) as a colorless liquid ($n_D^{20}$ unmeasurable).

| $^1$H-NMR data (300 MHz, CDCl$_3$ solvent, δ value) | |
|---|---|
| 1.08 | (3H, t) |
| 1.75 | (2H, h) |
| 2.38 | (3H, s) |
| 2.97 | (2H, t) |
| 6.71 | (1H, d) |
| 7.23 | (1H, d) |
| 7.32 | (1H, dd) |
| 7.57 | (1H, d) |
| 7.89 | (1H, bs) |

Example 16

Preparation of [2-difluoromethyl-5-(3-trifluoromethylpyrazolyl)phenyl] 2,2,2-trifluoroethyl sulfide (Compound No. V-295 of the Present Invention)

1.0 g (2.8 mmol) of 2-(2,2,2-trifluoroethylthio)-4-(3-trifluoromethylpyrazolyl)benzaldehyde (Compound No. V-275 of the present invention) prepared in the same manner as in Example 8 (9) was dissolved in 5 ml of methylene chloride and stirred together with 0.55 g (3.4 mmol of DAST (diethylaminosulfur trifluoride) in a nitrogen stream at room temperature for 4 hours. After further addition of 0.14 g (0.8 mmol) of DAST (diethylaminosulfur trifluoride), the reaction mixture was stirred at room temperature overnight. The reaction mixture was poured into 20 ml of ice-cold water, and 20 ml of methylene chloride was added. The methylene chloride layer was separated, washed with 20 ml of water twice and dried over anhydrous magnesium sulfate. The methylene chloride was distilled off under reduced pressure to obtain 0.75 g of [2-difluoromethyl-5-(3-trifluoromethylpyrazolyl)phenyl] 2,2,2-trifluoroethyl sulfide (yield 70.8%) as a yellow viscous liquid $n_D^{20}$ 1.4951).

| $^1$H-NMR data (300 MHz, CDCl$_3$ solvent, δ value) | |
|---|---|
| 3.50 | (2H, q) |
| 6.78 | (1H, d) |
| 7.16 | (1H, t) |
| 7.82 | (2H, s) |
| 8.02 | (1H, d) |
| 8.07 | (1H, s) |

Example 17

Preparation of [2-ethenyl-5-(3-trifluoromethylpyrazolyl)phenyl] 2,2,2-trifluoroethyl sulfide (Compound No. V-278 of the Present Invention)

2.83 g (8.0 mmol) of 2-(2,2,2-trifluoroethylthio)-4-(3-trifluoromethylpyrazolyl)benzaldehyde (Compound No. V-275 of the present invention) prepared in the same manner as in Example 8 (9), 2.85 g (8.0 mmol) of methyltriphenylphosphonium bromide and 1.38 g (10.0 mmol) of potassium carbonate were refluxed in a solvent mixture of 20 ml of dioxane and 0.3 ml of water with heating for 5 hours. After cooling down to room temperature, the insolubles were filtered off, and the dioxane was distilled off under reduced pressure. Purification of the residue by silica gel column chromatography afforded 1.23 g of [2-ethenyl-5-(3-trifluoromethylpyrazolyl)phenyl] 2,2,2-trifluoroethyl sulfide (yield 43.8%) as a pale yellow liquid ($n_D^{20}$ 1.5328).

| $^1$H-NMR data (300 MHz, CDCl$_3$ solvent, δ value) | |
|---|---|
| 3.41 | (2H, q) |
| 5.47 | (1H, dd) |
| 5.79 | (1H, dd) |
| 6.74 | (1H, d) |
| 7.29 | (1H, dd) |
| 7.67 | (2H, s) |
| 7.91 | (1H, s) |
| 8.95 | (1H, d) |

Examples of Preparation of Precursors

Reference Example 1

Preparation of 2-mercapto-4-(4-trifluoromethylphenyl)benzonitrile (Compound II)

(a) Preparation of 2-methylthio-4-(4-trifluoromethylphenyl)benzonitrile (Compound XVII)

To 3.0 g (11.3 mmol) of 2-fluoro-4-(4-trifluoromethylphenyl)benzonitrile in 50 ml of N,N-dimethylformamide, 7.0 g (15.0 mmol) of 15% aqueous sodium methyl mercaptan was added dropwise at room temperature. After 6 hours of stirring at 60° C., the reaction mixture was poured into 200 ml of ice-cold water and extracted with 100 ml of ethyl acetate twice. The ethyl acetate layer was washed with 100 ml of water twice and dried over anhydrous magnesium sulfate, and the ethyl acetate was distilled off under reduced pressure. Purification of the residue by silica gel column chromatography afforded 2.5 g of 2-methylthio-4-(4-trifluoromethylphenyl)benzonitrile (yield 75%) as white crystals (m.p. 128-129° C.).

(b) Preparation of 2-methylsulfinyl-4-(4-trifluoromethylphenyl)benzonitrile 2.5 g (8.5 mmol) of the methylthio analogue prepared in (a) was dissolved in 50 ml of chloroform, and 1.7 g (9.9 mmol) of m-chloroperbenzoic acid in chloroform was added dropwise at 0° C. with stirring. After 1 hour of stirring, 5% aqueous sodium bicarbonate was added for separation, and the chloroform layer was washed with 5% aqueous sodium sulfite and water and dried over anhydrous sodium sulfate, and the solvent was distilled off under reduced pressure. Purification of the residue by silica gel column chromatography afforded 2.2 g of 2-methylsulfinyl-4-(4-trifluoromethylphenyl)benzonitrile (yield 84.0%) as tawny crystals (m.p. 127-128° C.).

(c) Preparation of 2-mercapto-4-(4-trifluoromethylphenyl)benzonitrile (Compound II)

2.2 g (7.1 mmol) of 2-methylsulfinyl-4-(4-trifluoromethylphenyl)benzonitrile prepared in (b) was stirred in 15 ml of trifluoroacetic anhydride at room temperature for 12 hours, and the low-boiling matters were distilled off under reduced pressure. 50 ml of methanol and 3 g of 20% aqueous potassium hydroxide were added to the residue, and the reaction was carried out for 1 hour. The solvent was distilled off under reduced pressure, and the residue was mixed with 5% aqueous sulfuric acid and extracted with ethyl acetate. The ethyl acetate layer was dried over anhydrous sodium sulfate, and the solvent was distilled off under reduced pressure to obtain 1.0 g of 2-mercapto-4-(4-trifluoromethylphenyl)benzonitrile (yield 51.0%), which was used in Example 1 as the starting material.

Reference Example 2

Preparation of 1,1'-thiodi-[5-(2,6-dichloro-4-trifluoromethylphenyl)-2-methylbenzene] (Compound IV)

(a) Preparation of 4-(2,6-dichloro-4-trifluoromethylphenyl)toluene (Compound X)

To 5.7 g (26.1 mmol) of 4-iodotoluene in 30 ml of dry benzene, 17.0 ml of a n-butyllithium solution in hexane (1.60 mol/l) was added dropwise in a nitrogen stream at room temperature with stirring. After 2 hours of stirring at room temperature, 10 ml of 6.0 g (25.8 mmol) of 3,5-dichloro-4-fluorobenzotrifluoride in 10 ml of diethyl ether was added dropwise at 10° C. After another 12 hours of stirring at room temperature, the reaction mixture was poured into 100 ml of water for separation. The organic layer was washed with 50 ml of water twice and dried over anhydrous magnesium sulfate. The solvent was distilled off under reduced pressure to obtain 6.7 g of 4-(2,6-dichloro-4-trifluoromethylphenyl)toluene (yield 85.0%) as a colorless liquid.

(b) Preparation of 5-(2,6-dichloro-4-trifluoromethylphenyl)-2-methylbenzenesulfonyl chloride 6.7 g (22.0 mmol) of 4-(2,6-dichloro-4-trifluoromethylphenyl)toluene prepared in (a) was dissolved in 50 ml of chloroform, and 3.8 g (32.6 mmol) of chlorosulfonic acid was added dropwise at 0° C. with stirring. After further 3 hours of stirring at room temperature, the reaction mixture was poured into about 200 ml of ice-cold water for separation. The organic layer was washed with water twice and dried over anhydrous magnesium sulfate. The solvent was distilled off under reduced pressure to obtain 7.2 g of 5-(2,6-dichloro-4-trifluoromethylphenyl)-2-methylbenzenesulfonyl chloride (yield 81.0%).

(c) Preparation of 1,1'-thiodi-[5-(2,6-dichloro-4-trifluoromethylphenyl)-2-methylbenzene] (Compound IV)

To 0.7 g (18.4 mmol) of lithium aluminum hydride in 30 ml of diethyl ether, 7.2 g (17.8 mmol) of 5-(2,6-dichloro-4-trifluoromethylphenyl)-2-methylbenzenesulfonyl chloride in 30 ml of diethyl ether was added dropwise at -10° C. After 12 hours of stirring at room temperature, the reaction mixture was poured into 1N aqueous hydrochloric acid for separation. The organic layer was washed with 50 ml of water twice and dried over anhydrous magnesium sulfate, and the solvent was distilled off under reduced pressure. Purification of the residue by silica gel column chromatography affored 4.3 g of 1,1'-thiodi-[5-(2,6-dichloro-4-trifluoromethylphenyl)-2-methylbenzene] (yield 75.0%) as a pale yellow dough ($n_D^{20}$ 1.6066), which was used in Example 2 (1) as the starting material.

Reference Example 3

Preparation of 2-mercapto-4-(3-trifluoromethylpyrazolyl)benzonitrile (Compound II-1)

5.0 g (18.4 mmol) of 2-chloro-4-(3-trifluoromethylpyrazolyl)benzonitrile in N,N-dimethylformamide was stirred together with 1.86 g (23.9 mmol) of sodium sulfide at 120° C. for 30 minutes. The reaction mixture was cooled to room temperature, mixed with 100 ml of water, washed with 30 ml of ethyl acetate, and the aqueous layer was adjusted at pH 5-6 with citric acid, and extracted with 50 ml of ethyl acetate twice. The ethyl acetate layers were combined, washed with 50 ml of water twice and dried over anhydrous magnesium sulfate. The ethyl acetate was distilled off under reduced pressure to obtain 2-mercapto-4-(3-trifluoromethylpyrazolyl)benzonitrile (yield 97.6%) as a pale yellow powder, which was used in Example 1 (2) as the starting material.

| $^1$H-NMR data (300 MHz, CDCl$_3$ solvent, δ value) | |
|---|---|
| 4.28 | (1H, bs) |
| 6.79 | (1H, d) |
| 7.56 | (1H, dd) |
| 7.71 | (1H, d) |
| 7.87 | (1H, d) |
| 8.01 | (1H, d) |

Reference Example 4

Preparation of 1,1'-thiodi-[2-ethoxymethoxy-5-(4-trifluoromethylphenyl)benzene] (Compound IV)

To 3.0 g (10.1 mmol) of [4-(4-trifluoromethylphenyl)phenyl] ethoxymethyl ether in 30 ml of diethyl ether, 7.8 ml of a n-butyllithium solution in hexane (1.56 mol/l) was added dropwise at -20° C. with stirring. The resulting reaction mixture was stirred at room temperature for further 2 hours, then cooled to 0° C. and mixed with 0.6 g (18.8 mmol) of sulfur powder. After further 2 hours of stirring at room temperature, the reaction mixture was poured into diluted hydrochloric acid, and the ether layer was washed with water twice and dried over anhydrous magnesium sulfate. The solvent was distilled off under reduced pressure, 20 ml of dimethylsulfoxide was added to the residue, and reacted at 80° C. for 12 hours. The resulting reaction mixture was poured into about 200 ml of water and extracted with 100 ml of ethyl acetate twice. The organic layer was washed with water twice and dried over anhydrous magnesium sulfate, and the solvent was distilled off under reduced pressure, to obtain 1.6 g of 1,1'-thiodi-[2-ethoxymethoxy-5-(4-trifluoromethylphenyl)

benzene] (yield 48.5%) as a yellow solid (m.p. 61-62° C.), which was used in Example 2 (2) as the starting material.

Reference Example 5

(1) Preparation of 1,1'-thiodi-[2-cyano-5-(3-trifluoromethylpyrazolyl)benzene] (Compound IV)

3.0 g (11.1 mmol) of 2-mercapto-4-(3-trifluoromethylpyrazolyl)benzonitrile in 5 ml of dimethyl sulfoxide was stirred at 50° C. for 2 hours. The reaction mixture was cooled to room temperature and poured into 50 ml of water, and the organic matters were extracted with 20 ml of ethyl acetate twice. The ethyl acetate layers were combined, then washed with 30 ml of water twice and dried over anhydrous magnesium sulfate, and the ethyl acetate was distilled off under reduced pressure. Purification of the residue afforded 1.3 g of 1,1'-thiodi-[2-cyano-5-(3-trifluoromethylpyrazolyl)benzene] (yield 42.4%) as a yellow solid, which was used in Example 2 (3) as the starting material.

(2) Preparation of 1,1'-thiodi-[2-chloro-4-fluoro-5-(3-trifluoromethyltriazolyl)benzene (Compound IV)

2.2 g (7.1 mmol) of [2-chloro-4-fluoro-5(3-trifluoromethyltriazolyl)phenyl] methyl sulfide was converted to 2-chloro-4-fluoro-5(3-trifluoromethyltriazolyl)thiophenol in the same manner as in Reference Example 1 and then to 1.8 g of 1,1'-thiodi-[2-chloro-4-fluoro-5-(3-trifluoromethyltriazolyl)benzene (yield 85.7%) in the same manner as in Reference Example 5 (1), which was used in Example 2 (4) as the starting material.

Reference Example 6

Preparation of 4-methyl-3-trifluoromethylpyrazol (Compound XIII)

1.7 g (10.2 mmol) of 4-ethoxy-3-methyl-1,1,1-trifluoro-3-buten-2-on and 0.6 g (12.0 mmol) hydrazine hydrate were stirred in 50 ml of ethanol at room temperature for 2 hours. The ethanol was distilled off under reduced pressure, and the residue was separated with ethyl acetate and water. The organic layer was washed with water twice and dried over anhydrous magnesium sulfate. The solvent was distilled off under reduced pressure to obtain 1.3 g of 4-methyl-3-trifluoromethylpyrazol (yield 86.7%).

Reference Example 7

Preparation of 4-trifluoromethyl-1,6-dihydropyrimidine-6-oxide (Compound XIII)

6.9 g (48.6 mmol) of ethyl trifluoroacetate, 5 g (48.1 mmol) of formamidine acetate and 5.1 g (48.1 mmol) of sodium carbonate were refluxed in 50 ml of methanol for 6 hours. The methanol was distilled off under reduced pressure, and water and diluted hydrochloric acid were added. The crystal precipitate was filtered off and dried to give 5.3 g of 4-trifluoromethyl-1,6-dihydropyrimidine-6-oxide (yield 89.9%).

Reference Example 8

Preparation of N'-(4-methyl-3-n-propylthiophenyl)trifluoroacetohydrazidoyl chloride (Compound XXI)

2.0 g (10 mmol) of 4-methyl-3-n-propylthiophenylhydrazine in 15 ml of pyridine was stirred at 0° C. 2.1 g (10 mmol) of trifluoroacetic anhydride was added dropwise, and the reaction mixture was stirred at room temperature overnight. The pyridine was distilled off from the reaction mixture under reduced pressure, and the residue was poured into 50 ml of water and extracted with 30 ml of ethyl acetate. The ethyl acetate layer was washed with 20 ml of water three times and dried over anhydrous magnesium sulfate. The ethyl acetate was distilled off under reduced pressure to obtain 2.3 g of N'-(4-methyl-3-n-propylthiophenyl)trifluoroacetohyodrazide. 2.0 g (6.8 mmol) of the hydrazide was dissolved in 15 ml of acetonitrile and refluxed together with 2.0 g (7.6 mmol) of triphenylphosphine and 5 ml of carbon tetrachloride with heating for 2 hours. After cooling down to room temperature, the acetonitrile was distilled off under reduced pressure. 30 ml of toluene was added to the residue, and the insolubles were removed by decantation (twice). The toluene layers were combined, washed with 40 ml of water and dried over anhydrous magnesium sulfate, and the toluene was distilled off under reduced pressure. Purification of the residue by silica gel column chromatography afforded 1.0 g (3.2 mmol) of N'-(4-methyl-3-n-propylthiophenyl)trifluoroacetohydrazidoyl chloride, which was used in Example 10 as the starting material.

Reference Example 9

Preparation of 1-chloro-5-(2,6-dichloro-4-trifluoromethylphenyl)-2-nitrobenzene (Compound XVI)

To 10.0 g (41.9 mmol) of 1-chloro-3-iodobenzene in 50 ml of dry benzene, 32.0 ml of a n-butyllithium solution in hexane (1.56 mol/l) was added dropwise in a nitrogen stream at room temperature with stirring. After another 2 hours of stirring at room temperature, 9.9 g (42.5 mmol) of 3,5-dichloro-4-fluorobenzotrifluoride was added dropwise at 10° C. After another 12 hours of stirring at room temperature, the reaction mixture was poured into 500 ml of water for separation. The organic layer was washed with 200 ml of water twice and dried over anhydrous magnesium sulfate, and the solvent was distilled off under reduced pressure. Purification of the residue by silica gel column chromatography afforded 5.0 g of 1-chloro-3-(2,6-dichloro-4-trifluoromethylphenyl)benzene (yield 35.0%).

To 50 ml of fuming nitric acid, 5.0 g (15.4 mmol) of 1-chloro-3-(2,6-dichloro-4-trifluoromethylphenyl)benzene was added dropwise at −30° C. After 15 minutes of stirring at the same temperature, the reaction mixture was warmed to 5° C., poured into about 200 ml of ice-cold water and extracted with 100 ml of diethyl ether twice. The diethyl ether layer was washed with 200 ml of water twice and dried over anhydrous magnesium sulfate, and the diethyl ether was distilled off under reduced pressure. Purification of the residue by silica gel column chromatography afforded 3.0 g of 1-chloro-5-(2, 6-dichloro-4-trifluoromethylphenyl)-2-nitrobenzene (yield 52.6%) as a pale yellow liquid ($n_D^{20}$ 1.5744), which was used in Example 8 (2) as the starting material.

Reference Example 10

Preparation of 2-fluoro-4-(2,4-dichlorophenyl)benzonitrile (Compound XVI)

1.0 g (5.2 mmol) of 2,4-dichlorophenylboronic acid, 1.1 g (5.5 mmol) of 4-bromo-2-fluorobenzonitrile, 1.6 g (15.0 mmol) of sodium carbonate and 0.8 g (0.7 mmol) of tetrakis (triphenylphosphine) palladium were added to a solvent mixture of 50 ml of toluene, 25 ml of ethanol and 25 ml of water, and the reaction was carried out under reflux with heating for 2 hours. The reaction mixture was poured into ice-cold water and extracted with toluene. The toluene layer was washed with water twice and dried over anhydrous magnesium sulfate. The solvent was distilled off under reduced pressure to obtain 1.3 g of 2-fluoro-4-(2,4-dichlorophenyl)benzonitrile (yield 93.0%), which was used in Example 8 (1) as the starting material.

Reference Example 11

Preparation of 4-(4-trifluoromethylphenyl)-2,5-difluoronitrobenzene (Compound XVI)

16.3 g (68.5 mmol) of 2,5-difluoro-4-bromonitrobenzene, 13.0 g (68.4 mmol) of 4-trilfluoromethylphenylbononic acid, 15.0 g (141.5 mmol) of sodium carbonate and 2.0 g (1.8 mmol) of tetrakis(triphenylphosphine) palladium were added to a solvent mixture of 200 ml of dimethoxyethane and 50 ml of water, and the reaction was carried out under reflux with heating for 8 hours. The dimethoxyethane was distilled off under reduced pressure, and after addition of 300 ml of ice-cold water, organic matters were extracted with 100 ml of ethyl acetate twice. The ethyl acetate layers were combined, washed with 200 ml of water twice and dried over anhydrous magnesium sulfate, and the solvent was distilled off under reduced pressure. Purification of the residue by silica gel column chromatography afforded 13.5 g of 4-(4-trifluoromethylphenyl)-2,5-difluoronitrobenzene (yield 65.0%) as white crystals (m.p. 113-114° C.), which was used in Example 8 (3) as the starting material.

Reference Example 12

Preparation of 2-fluoro-4-(5-trifluoromethylpyridin-2-yl)benzonitrile (Compound XVI)

4.0 g (19.7 mmol) of 2-fluoro-4-bromobenzaldehyde, 2.0 g (32.3 mmol) of ethylene glycol, 0.2 g (1.1 mmol) of p-toluenesulfonic acid and 100 ml of toluene were put into a round-bottomed flask and azeotropically dehydrated for 4 hours. After the reaction, the organic layer was washed with aqueous sodium bicarbonate and water and dried over anhydrous magnesium sulfate. The toluene was distilled off under reduced pressure to obtain 4.7 g of 2-(2-fluoro-4-bromophenyl)dioxolan (yield 97%). The dioxolan was dissolved in 50 ml of ether, and 15.0 ml of a n-butyllithium solution in hexane (1.56 mol/l) was added dropwise in a nitrogen stream at −60° C. with stirring. After another 2 hours of stirring at −60° C., 3.0 g (28.9 mmol) of trimethyl borate in 10 ml of diethyl ether was added dropwise, and then reaction mixture was stirred at room temperature for 12 hours. The reaction mixture was cooled back to 0° C., stirred together with 5 ml of diluted hydrochloric acid for 1 hour and poured into 100 ml of water for partitioning. The organic layer was washed with 50 ml of water twice and dried over anhydrous magnesium sulfate. The solvent was distilled off under reduced pressure to obtain 2.4 g of 4-(dioxobororan-2-yl)-2-fluorobenzaldehyde (yield 69%). The benzaldehyde, 3.5 g (14.2 mmol) of 2-bromo5-trifluoromethylpyridine, 3.2 g (30.0 mmol) of sodium carbonate and 1.5 g (1.4 mmol) of tetrakis(triphenylphosphine) palladium were added to a solvent mixture of 100 ml of toluene, 40 ml of ethanol and 40 ml of water and stirred with heating and reflux for 2 hours. The reaction mixture was poured into ice-cold water and extracted with toluene. The toluene layer was washed with water twice and dried over anhydrous magnesium sulfate, and the solvent was distilled off under reduced pressure. Purification of the residue by silica gel column chromatography afforded 2.3 g of 4-(5-trifluoromethylpyridin-2-yl)-2-fluorobenzaldehyde (yield 81%). It was dissolved in 100 ml of ethanol and stirred together with 1.0 g (14.5 mmol) of hydroxylamine hydrochloride and 1.0 g (10 mmol) of triethylamine at room temperature for 12 hours. The ethanol was distilled off under reduced pressure, and the residue was separated with 50 ml of water and 50 ml of ethyl acetate. The organic layer was washed with 50 ml of water twice and dried over anhydrous magnesium sulfate, and the solvent was distilled off under reduced pressure. The residue was dissolved in pyridine, mixed with 2.1 g (10 mmol) of trifluoroacetic anhydride and allowed to stand overnight. The pyridine was distilled off under reduced pressure, and the residue was separated with 50 ml of aqueous sodium bicarbonate and 50 ml of ethyl acetate. The organic layer was washed with 50 ml of water twice and dried over anhydrous magnesium sulfate. The solvent was distilled off under reduced pressure to obtain 1.8 g of 2-fluoro-4-(5-trifluoromethylpyridin-2-yl)benzonitrile (yield 81%), which was used in Example 8 (4) as the starting material.

Reference Example 13

Preparation of 2-fluoro-4-(6-oxo-4-trifluoromethyl-1,6-dihydropyrimidin-1-yl)benzonitrile (Compound XVI)

0.8 g (20 mmol) of 60% sodium hydride was dispersed in 100 ml of N,N-dimethylformamide and mixed with 3.3 g (20 mmol) of 4-trifluoromethyl-1,6-dihydropyrimidine-6-oxide prepared in Reference Example 7 with stirring. After generation of hydrogen gas was over, 2.8 g (20 mmol) of 2,4-difluorobenzonitrile was added, and the reaction was carried out at 110° C. for 12 hours. The solvent was distilled off under reduced pressure, and the residue was separated with 50 ml of water and 50 ml of ethyl acetate. The organic layer was washed with 50 ml of water twice and dried over anhydrous magnesium sulfate, and the ethyl acetate was distilled off under reduced pressure to obtain 1.1 g of 2-fluoro-4-(6-oxo-4-trifluoromethyl-1,6-dihydropyrimidin-1-yl)benzonitrile (yield 19%), which was used in Example 8 (5) as the starting material.

Reference Example 14

Preparation of 4-(5-chlorothiophen-2-yl)-2-fluorobenzonitrile (Compound XVI)

Coupling of 2.0 g (10.4 mmol) of 4-(dioxobororan-2-yl)-2-fluorobenzaldehyde and 2.2 g (11.1 mmol) of 2-bromo-5-chlorothiophene similar to that in Reference Example 11 followed by treatment with hydroxylamine hydrochloride afforded 0.9 g of 4-(5-chlorothiophen-2-yl)-2-fluorobenzonitrile (yield 38%), which was used in Example 8 (6) as the starting material.

Reference Example 15

Preparation of 2-chloro-4-(3-trifluoromethylpyrazolyl)benzaldehyde (Compound XVI)

4.08 g (30.0 mmol) of 3-trifluoromethylpyrazol, 4.75 mmol (30.0 mmol) of 2-chloro-4-fluorobenzaldehyde and 4.14 g (30.0 mmol) of potassium carbonate in 30 ml of N,N-dimethylformamide were stirred at 60° C. for 2 hours. After cooling to room temperature, the reaction mixture was poured into 100 ml of water, and the organic matters were extracted with 50 ml of ethyl acetate twice. The ethyl acetate layers were combined, washed with 50 ml of water twice and dried over anhydrous magnesium sulfate, and the ethyl acetate was distilled off under reduced pressure. The residue afforded 7.18 g of 2-chloro-4-(3-trifluoromethylpyrazolyl)benzaldehyde (yield 87.2%) as a pale yellow powder, after washed with n-hexane.

Reference Example 16

Preparation of 2-chloro-4-(3-trifluoromethylpyrazolyl)benzonitrile (Compound XVI)

2.5 g (18.4 mmol) of 3-trifluoromethylpyrazole, 2.9 g (18.4 mmol) of 2-chloro-4-fluorobenzonitrile and 2.8 g (20.2 mmol) of potassium carbonate in 20 ml of N,N-dimethylformamide were stirred at 60° C. for 2 hours. After cooling to room temperature, the reaction mixture was poured into 100 ml of water, and the organic matters were extracted with 50 ml of ethyl acetate twice. The ethyl acetate layers were combined, washed with 50 ml of water twice and dried over anhydrous magnesium sulfate, and the ethyl acetate was distilled off under reduced pressure. After washed with n-hexane, the residue afforded 4.6 g of 2-chloro-4-(3-trifluoromethylpyrazolyl)benzonitrile (yield 92.0%) as a white powder, which was used in Reference Example 3 as the starting material.

Reference Example 17

Preparation of 3-(2,4-dichlorophenyl)aniline (Compound XVIII)

2.0 g (10.4 mmol) of 2,4-dichlorophenylboronic acid, 2.4 g (11.0 mmol) of 3-iodoaniline, 3.2 g (30.0 mmol) of sodium carbonate and 1.6 g (1.4 mmol) of tetrakis(triphenylphosphine) palladium were added to a solvent mixture of 70 ml of toluene, 30 ml of ethanol and 30 ml of water, and the reaction was carried out under reflux with heating for 2 hours. The reaction mixture was poured into ice-cold water and extracted with toluene. The toluene layer was washed with water twice and dried over anhydrous magnesium sulfate. The solvent was distilled off under reduced pressure to obtain 0.9 g of 3-(2,4-dichlorophenyl)aniline (yield 36.0%), which was used in Example 9 as the starting material.

Reference Example 18

Preparation of [2-chloro-4-fluoro-5-(3-trifluoromethyltriazolyl)phenyl] methyl sulfide 4.1 g (19.8 mmol) of 4-chloro-2-fluoro-5-methylthiophenylhydrazine, 2.9 g (20.1 mmol) of trifluoroacetaldehyde hemi-acetal, 0.3 g (1.5 mmol) of p-toluenesulfonic acid monohydrate and 50 ml of ethanol were put into a round-bottomed flask, and the reaction was carried out with reflux for 1 hour. Then, the ethanol was distilled off under reduced pressure to obtain N'-(4-chloro-2-fluoro-5-methylthiophenyl)trifluoroacetaldehydehydrazone. It was dissolved in 50 ml of N,N-dimethylformamide and mixed with 3.8 g (21.3 mmol) of N-bromosuccinimide at room temperature. After another 1 hour of stirring at room temperature, the solvent was distilled off under reduced pressure, and the residue was poured into 50 ml of water and extracted with 30 ml of ethyl acetate. The ethyl acetate layer was washed with 20 ml of water and dried over anhydrous magnesium sulfate. The ethyl acetate was distilled off under reduced pressure to obtain 6.5 g of N'-(4-chloro-2-fluoro-5-methylthiophenyl)trifluoroacetohydrazidoyl bromide (90.3%). It was dissolved in 50 ml of N,N-dimethylformamide and mixed with 2 ml of 28% aqueous ammonia. After another 1 hour of stirring at room temperature, the solvent was distilled off under reduced pressure, and the residue was poured into 50 ml of water and extracted with 30 ml of ethyl acetate. The ethyl acetate layer was washed with 20 ml of water three times and dried over anhydrous magnesium sulfate. The ethyl acetate was distilled off under reduced pressure to obtain 4.5 g of N'-(4-chloro-2-fluoro-5-methylthiophenyl)trifluoroacetamizine (83.8%). The N'-(4-chloro-2-fluoro-5-methylthiophenyl)trifluoroacetamizine and 0.3 g (1.5 mmol) of p-toluenesulfonic acid monohydrate were refluxed in 30 ml of trimethyl orthoformate for 6 hours, and then the trimethyl orthoformate was distilled off under reduced pressure. The residue was poured into 50 ml of water and extracted with 30 ml of ethyl acetate. The ethyl acetate layer was washed with 20 ml of water twice and dried over anhydrous magnesium sulfate. The ethyl acetate was distilled off under reduced pressure to obtain 2.2 g of [2-chloro-4-fluoro-5-(3-trifluoromethyltriazolyl)phenyl] methyl sulfide (47.2%), which was used in Reference Example 5 (2) as the starting material.

The insecticides and miticides of the present invention contain 3-arylphenyl sulfide derivatives represented by general formula (I) as an active ingredient.

When a compound of the present invention is used as the active ingredient of a pesticide, it may be used by itself. However, it can be formulated into various formulations such as an emulsifiable concentrate, a suspension, a dust, a granule, a tablet, a wettable powder, a water-soluble concentrate, a solution, a flowable suspension, a water dispersible granule, an aerosol, a paste, an oil formulation and a concentrated emulsion in water in combination with various carriers, surfactants and other adjuvants which are commonly used for formulation as agricultural adjuvants. They are blended usually in such proportions that the active ingredient is from 0.1 to 90 parts by weight and the agricultural adjuvants are from 10 to 99.9 parts by weight.

The carriers to be used for such formulation may be classified into solid carriers and liquid carriers. The solid carriers include, for example, animal and plant powders such as starch, activated carbon, soybean powder, wheat flour, wood flour, fish flour and powdered milk, and mineral powders such as talc, kaolin, bentonite, calcium carbonate, zeolite, diatomaceous earth, white carbon, clay and alumina. The liquid carriers include, for example, water; alcohols such as isopropyl alcohol and ethylene glycol; ketones such as cyclohexanone and methyl ethyl ketone; ethers such as dioxane and tetrahydrofuran; aliphatic hydrocarbons such as kerosene and light oil; aromatic hydrocarbons such as xylene, trimethylbenzene, tetramethylbenzen, methylnaphthalene and solvent naphtha; halogenated hydrocarbons such as chlorobenzene; acid amides such as dimethylacetamide; esters such as glycerin esters of fatty acids; nitriles such as acetonitrile; and sulfur-containing compounds such as dimethyl sulfoxide.

The surfactants include, for example, metal salts of alkylbenzenesulfonic acids, metal salts of dinaphthylmethandisulfonic acids, salts of alcohol sulfates, alkylarylsulfonates, lignin sulfonates, polyoxyethylene glycol ethers, polyoxyethylene alkyl aryl ethers, polyoxyethylene sorbitan monoalkylates.

The other adjuvants include, for example, adhesive agents and thickeners such as carboxymethylcellulose, gum arabic, sodium arginate, guar gum, tragacanth gum, and polyvinyl alcohol, antifoaming agents such as metal soap, physical property improvers such as fatty acids, alkyl phosphate salts, silicone and paraffin and coloring agents.

When these formulations are practically used, they may be used directly or after diluted with a diluent such as water to a predetermined concentration. Various formulations containing the compounds of the present invention, whether diluted or not, may be applied by conventional methods, i.e., application methods (such as spraying, misting, atomizing, dusting, granule application, paddy water application and seeding box application), soil treatment (such as mixing or drenching), surface application (such as painting, dressing and covering), dipping or poison bait. Further, the above active ingredients may be incorporated into livestock feeds so as to prevent infestation or growth of pest, especially pest insects after they are voided in excrement. Otherwise, they can also be applied in low volume at high concentration, when the active ingredient may be contained up to 100%.

The pesticides of the present invention are applied usually at an active ingredient concentration of from 0.1 to 50000 ppm, preferably from 1 to 10000 ppm.

The active ingredient concentration can be suitably changed in accordance with the type of formulation, the method, the purpose, the season or the site of application and the degree of infestation the pest. For example, when an aquatic pest is to be controlled by applying a formulation within the above-mentioned concentration range to the infested site, the concentration of the active ingredient in water may be below the above-mentioned range. The dose per unit area is usually from 0.1 to 5000 g, preferably 1 to 1000 g, per 1 ha in terms of the compound that serves as the active ingredient. However, the dose is not limited to such specific range.

The compounds of the present invention are sufficiently effective when used alone. However, they may be used, if necessary, in combination or in admixture with fertilizers or other agrochemicals such as insecticides, miticides, nematicides, fungicides, antivirus agents, attractants, herbicides and plant growth regulants, and such combined use can sometimes produce improved effects.

Typical examples of the insecticides, fungicides, miticides which may be used in combination with the compounds of the present invention, will be given below.

Organophosphorus compounds and carbamate insecticides: fenthion, fenitrothion, diazinon, chlorpyriphos, oxydeprofos, vamidothion, phenthoate (fentoat), dimethoate, formothion, malathion, trichlorphon, thiometon, phosmet, dichlorvos, acephate, EPBP, methyl-parathion, oxydimetonmethyl, ethion, dioxabenzofos, cyanophos (cyanofos), isoxathion, pyridafenthion, phosalone, metidation, sulprophos (sulprofos), chlorfenvinphos, tetrachlorvinphos, dimethylvinphos, propahos, isofenphos, disulfoton, profenofos, pyraclofos, monocrotophos, azinphos-methyl, aldikarb, methomyl, thiodicarb, carbofuran, carbosulfan, benfuracarb, furathiocarb, propoxur, fenobcarb, metolcarb, isoprocarb, carbaryl (carbaril), pirimicarb, ethiofencarb, dichlophenthion, pirimiphos-methyl, quinalphos, chlorpyriphos-methyl, prothiophos, naled, EPN, XMC, bendiocarb, oxamyl, alanycarb, chlorethoxyfos, etc.

Pyrethroid insecticides: permethrin, cypermethrin, deltamethrin, fenvalerate, fenpropathrin, piretrine, allethrin, tetramethrin, resmethrin, dimethrin, proparthrin, phenothrin, prothrin, fluvalinate, cyfluthrin, cyhalothrin, flucythrinate, etofenprox, cycloprothrin, tralomethrin, silafluofen, tefluthrin, bifenthrin, acrinathrin, etc.

Acylurea type and other insecticides: diflubenzuron, chlorfluazuron, hexaflumuron, triflumuron, teflubenzuron, flufenoksuron, flucycloxuron, buprofezin, pyriproxyfen, lufenuron, cyromazine, methoprene, endosulphan, diafenthiuron, imidacloprid, fipronil, nicotin-sulfate, rotenone, metaldehyde, machine oil, microbial pesticides such as BT and insect viruses, fenoxycarb, cartap, thiocyclam, bensultap, tebufenozide, chlorphenapyr, emamectin-benzoate, acetaprid, nitenpyram, sodium oleate, rapeseed oil, etc.

Nematicides: phenamiphos, fosthiazate, ethoprophos, methyl isothiocyanate, 1,3-dichloropropene, DCIP, etc.

Miticides: chlororbenzilate, phenisobromolate, dicofol, amitraz, propargit, benzomate, hexythiazox, fenbutatin oxide, polynactin, quinomethionate, chlorfenson, tetradifon, avermectin, milbemectin, clofentezine, pyridaben, fenpyroximate, tebufenpyrad, pyrimidifen, fenothiocarb, dienochlor, etoxazole, halfenprox, etc.

Fungicides: thiophanate-methyl, benomil, carbendazol, thiabendazol, folpet, thiuram, diram, zineb, maneb, polycarbamate, iprobenfos, edifenphos, fthalide, probenazole, isoprothiolane, chlorothalonil, captan, polyoxin, blasticidin-S, kasugamycin, streptomycin, validamycin, tricyclazole, pyroquilone, phenazine oxide, mepronil, flutolanil, pencycuron, iprodione, hymexazol, metalaxyl, triflumizole, triforine, triadimefone, bitertanol, fenarimol, propikonazol, cymoxanil, prochloraze, pefurazoate, hexaconazole, myclobutanil, diclomezine, tecloftalam, propineb, dithianon, phosethyl, vinclozolin, procymidone, oxadixyl, guazatine, propamocarb-hydrochloride, fluazinam, oxolinic acid, hydroxyisoxazole, mepanipyrim.

The compounds of the present invention exhibit excellent pesticidal activities against pests such as pest hemiptera, pest lepidoptera, pest coleoptera, pest diptera, pest hymenoptera, pest orthoptera, pest isoptera, pest thysanoptera, mites and plant-parasitc nematodes. The following pest insects may be mentioned as such pests.

Pest hemiptera: bugs (HETEROPTERA) such as bean bug (*Riptortus clavatus*), southern green stink bug (*Nezara viridula*), lygus bugs (*Lygus* sp.), hairy chinch bug (*Blissus leucopterus*) and pear lace bug (*Stephanitis nashi*); leafhoppers (*Circulifer* sp.) such as green rice leafhopper (*Nephotettix cincticeps*) and leafhoppers (*Empoasca* sp., *Erythroneura* sp., *Circulifer* sp.); delphacid planthoppers such as brown rice planthopper (*Nilaparvata lugens*), white-backed planthopper (*Sogatella furcifera*) and small brown planthopper (*Laodelphax striatellus*); jumping plantlice such as Psyllids (*Psylla* sp.); whiteflies such as sweetpotato whitefly (*Bemisia tabaci*) and greenhouse whitefly (*Trialeurodes vaporariorum*); aphids such as grapeleaf louse (*Viteus vitifolii*), green peach aphid (*Myzus persicae*), green apple aphid (*Aphis pomi*), cotton aphid (*Aphis gossypii*), *Aphis fabae*, turnip aphid (*Rhopalosiphum psedobrassicas*), glasshouse-potato aphid (*Aulacorthum solani*) and greenbug (*Schizaphis graminum*); mealy bugs or scales such as Comstock mealybug (*Pseudococcus comstocki*), red wax scale (*Ceroplastes rubens*), San Jose scale (*Comstockaspis perniciosa*) and arrowhead scale (*Unaspis yanonensis*) and *Rhodimius* sp.

Pest lepidoptera: tortricids such as oriental tea tortrix (*Homona magnanima*), summer fruit tortrix (*Adoxophyes orana*), tortricids (*Sparganothis pilleriana*), oriental fruit moth (*Grapholitha molesta*), soybean pod borer (*Leguminivora glycinivorella*), codling moth (*Laspeyresia pomonella*), *Eucosma* sp. and *Lobesia botrana*; Cochylidae such as grape cochylid (*Eupoecillia ambiguella*); bagworm moths such as *Bambalina* sp.; tineids such as European grain moth (*Nemapogon granellus*) and casemaking clothes moth (*Tinea translucens*); lyonetiid moths such as *Lyonetia prunifoliella*; leafblotch miners such as apple leafminer (*Phyllonorycter rigoniella*); Phyllocnistidae such as citrus leafminer (*Phyllocnistis citrella*); yponomeutids such as diamondback moth (*Plutella xylostella*) and *Prays citri*; clearwing moths such as grape clearwing moth (*Paranthrene regalis*) and *Synanthedon* sp.; gelechiid moths such as pink bollworm (*Pectinophora gossypiella*), potato tuberworm (*Phthorimaea operculella*) and *Stomopteryx* sp.; Carposinidae such as peach fruit moth (*Carposina niponensis*); slug caterpillarmoths such as oriental moth (*Monema flavescens*); pyralid moths such as Asiatic rice borer (*Chilo suppressalis*), rice leafroller (*Cnaphalocrocis medinalis*), *Ostrinia nubilalis*, oriental corn borer (*Ostrinia furnacalis*), cabbage webworm (*Hellula*

*undalis*), greater wax moth (*Galleria mellonella*), *Elasmopalpus lignosellus* and *Loxostege sticticalis*; whites such as common cabbageworm (*Pieris rapae*); geometrid moths such as mugwort looper (*Ascotis selenaria*); tent caterpillar moths such as tent caterpillar (*Malacosoma neustria*); sphinx moths such as *Manduca sexta*; tussock moths such as tea tussock moth (*Euproctis pseudoconspersa*) and gypsy moth (*Lymantria dispar*); tiger moths such as fall webworm (*Hyphantria cunea*); and owlet moths such as tobacco budworm (*Heliothis virescens*), bollworm (*Helicoverpa zea*), beet armyworm (*Spodoptera exigua*), cotton bollworm (*Helicoverpa armigera*), common cutworm (*Spodoptera litura*), cabbage armyworm (*Mamestra brassicae*), black cutworm (*Agrotis ipsiron*), rice armyworm (*Pseudaletia separata*) and cabbage looper (*Trichoplusia ni*).

Pest coleoptera: chafers such as cupreous chafer (*Anomala cuprea*), Japanese beetle (*Popillia japonica*), soybean beetle (*Anomala rufocuprea*) and *Eutheola rugiceps*; click beetles such as wireworm (*Agriotes* sp.) and *Conodeus* sp.; ladybirds such as twenty-eight-spotted ladybird (*Epilachna vigintioctopunctata*) and Mexican bean beetle (*Epilachna varivestis*); darkling beetles such as red flour beetle (*Tribolium castaneum*); longicorn beetles such as white-spotted longicorn beetle (*Anoplophora malasiaca*) and pine sawyer (*Monochamus alternatus*); seed beetles such as bean weevil (*Acanthoscelides obtectus*) and adzuki bean weevil (*Callosobruchus chinensis*); leaf beetles such as colorado potato beetle (*Leptinotarsa decemlineata*), corn rootworm (*Diabrotica* sp.), rice leaf beetle (*Oulema oryzae*), beet flea beetle (*Chaetocnema concinna*), *Phaedon cochlearias, Oulema melanopus* and *Dicladispa armigera*; Apionidae such as *Apion godmani*; weevils such as rice water weevil (*Lissorhoptrus oryzophilus*) and cotton boll weevil (*Anthonomus grandis*); Rhynchophoridae such as maize weevil (*Sitophilus zeamais*); bark beetles; dermestid beetles; and drugstore beetles.

Pet diptera: rice crane fly (*Tipra ano*), rice midge (*Tanytarsus oryzae*), *Orseolia oryzae, Ceratitis capitata*, rice leafminer (*Hydrellia griseola*), cherry drosophila (*Drosophila suzukii*), frit fly (*Oscinella frit*), rice stem maggot (*Chlorops oryzae*), French bean miner (*Ophiomyia phaseoli*), legume leafminer (*Liriomyza trifolii*), spinach leafminer (*Pegomya hyoscyami*), seedcorn maggot (*Hylemia platura*), sorghum fly (*Atherigona soccata*), muscid fly (*Musca domestica*), *Gastrophilus* sp., stomoxiid flies (*Stomoxys* sp.), *Aedes aegypti, Culex pipiens, Anopheles slnensis* and *Culex tritaeniorhynchus*.

Pest hymenoptera: stem sawflies (*Cephus* sp.); eurytomids (*Harmolita* sp.); cabbage sawflies (*Athalia* sp.), hornets (*Vespa* sp.) and fire ants.

Pest orthoptera: German cockroach (*Blatella germanica*); American cockroach (*Periplaneta americana*); African mole cricket (*Gryllotalpa africana*); Asiatic locust (*Locusta migratoria migratoriodes*); and *Melanoplus sanguinipes*.

Pest isoptera: termites (*Reticulitermes speratus*) and Formosan subterranean termite (*Coptotermes formosanus*).

Pest thysanopetra: yellow tea thrips (*Scirtothrips dorsalis*); thrips (*Thrips palmi*); greenhouse thrips (*Heliothrips haemorrholidalis*); western flower thrips (*Frankliniella occidentalis*) and rice aculeated thrips (*Haplothrips aculeatus*).

Mites: two-spotted spider mite (*Tetranychus urticae*); Kanzawa spider mite (*Tetranychus kanzawai*); citrus red mite (*Panonychus citri*); European red mite (*Panonychus ulmi*), yellow spider mite (*Eotetranychus carpini*); Texas citrus mite (*Eotetranychus banksi*); citrus rust mite (*Phyllocoptruta oleivora*); broad mite (*Polyphagotarsonemus latus*); false spider mites (*Brevipalpus* sp.); bulb mite (*Rhizoglyphus robini*) and mold mite (*Tyrophagus putrescentiae*).

Plant-parasitic nematodes: southern root-knot nematode (*Meloidogyne incognita*); root-lesion nematode (*Pratylenchus* sp.); soybean cyst nematode (*Heterodera glycines*); rice white-tip nematode (*Aphelenchoides besseyi*) and pine wood nematode (*Bursaphelenchus xylophilus*).

Other pests unfavorable animals, unhygrinic insects, and parasites: gastropods (*Gastropoda*) such as apple snails (*Pomacea canaliculata*), slugs (*Incilaria* sp.) and giant African snail (*Achatina fulica*); isopods (*Isopoda*) such as pillbug (*Armadillidium* sp.), sow bug and centipede; booklice such as *Liposcelis* sp.; siverfish such as *Ctenolepisma* sp.; fleas such as *Pulex* sp. and *Ctenocephalides* sp.; bird lice such as *Trichodectes* sp.; bed bugs such as *Cimex* sp.; aminal-parasitic mites such as *Boophilus microplus* and *Haemaphysalis longicornis* and Epidermoptidae.

Further, the compounds of the present invention are effective also against pest insects which show resistance to organophosphorus compounds, carbamate compounds, synthetic pyrethroid compounds, acylurea compounds or conventional insecticides.

Effect of the Invention

Thus, compounds of the present invention exhibit excellent pesticidal effects against a wide range of pests including pest hemiptera, pest lepidoptera, pest coleoptera, pest diptera, pest hymenoptera, pest orthoptera, pest isoptera, pest thysanoptera, mites and plant-parastic nematodes, and they are also capable of controlling pests which have acquired resistance to conventional pesticides.

Now, formulation methods will be described in detail with reference to typical Formulation Examples. However, it should be understood that the types and the proportions of the compounds and the adjuvants are not restricted by these specific Examples and may be varied within wide ranges. In the following examples, "%" means "% by weight".

Formulation Example 1

Emulsifiable Concentrate

30% of compound (I-28), 20% of cyclohaxanone, 11% of polyoxyethylene alkyl aryl ether, 4% of calcium alkylbenzenesulfonate and 35% of methylnaphthalene were uniformly dissolved to obtain an emulsifiable concentrate.

Formulation Example 2

Wettable Powder

10% of compound (I-28), 0.5% of the sodium salt of a naphthalenesulfonic acid/formalin condensate, 0.5% of polyoxyethylene alkyl aryl ether, 24% of diatomaceous earth and 65% of clay were uniformly mixed and pulverized to obtain a wettable powder.

Formulation Example 3

Dust

2% of compound (I-28), 5% of diatomaceous earth and 93% of clay were uniformly mixed and pulverized to obtain a dust.

Formulation Example 4

Granule

5% of compound (I-28), 2% of sodium lauryl alcohol sulfate, 5% of sodium lignin sulfonate, 2% of carboxymethylcellulose and 86% of clay were uniformly mixed and pulverized. 100 parts by weight of this mixture was kneaded with 20 parts by weight of water, formed into granules of from 14 to 32 mesh by an extrusion-type granulator and dried to obtain a granule formulation.

Now, the effects of the pesticides containing the compounds of the present invention as active ingredients will be described with reference to Test Examples.

Test Example 1 Insecticidal Test on Two-Spotted Spider Mites

Wettable powders were prepared in accordance with Formulation Example 2 and diluted to an active ingredient concentration of 500 ppm. Soybean seedlings which had been inoculated with adult two-spotted spider mites were immersed in the resulting solutions and dried in air. The treated seedlings were placed in a thermostatic chamber for 13 days, and the mite survivors were counted for calculation of the preventive value by using Equation 1. Typical compounds which showed miticidal effect corresponding to preventive values of 90 or more in the test are I-2, I-3, I-10, I-12, I-17, I-18, I-19, I-21, I-24, I-26, I-27, I-28, I-29, I-32, I-35, I-37, I-38, I-40, I-42, I-44, I-45, I-46, I-48, I-49, I-50, I-51, I-52, I-53, I-54, I-59, I-60, I-61, I-76, I-77, I-78, I-79, I-81, I-82, I-82, I-85, I-92, I-93, I-96, I-98, I-99, I-100, I-103, I-107, I-111, I-113, I-114, I-118, I-119, I-120, I-122, I-123, I-124, I-127, I-128, I-129, I-130, I-131, I-132, I-133, I-134, I-137, I-151, I-152, I-153, I-163, I-167, I-170, I-173, I-175, I-176, I-178, I-179, I-180, I-181, I-183, I-184, I-185, I-186, I-187, I-188, I-189, I-190, I-191, I-192, I-193, I-194, I-196, I-198, I-199, I-204, I-205, I-206, I-207, I-208, I-209, I-210, I-211, I-213, I-215, I-216, I-219, I-220, I-221, I-222, I-223, I-224, I-227, I-228, I-229, I-230, I-232, I-233, I-234, I-235, I-236, I-238, I-239, I-244, I-245, I-248, I-249, I-250, I-251, I-252, I-253, I-254, I-255, I-256, I-257, I-258, I-259, I-260, I-261, I-262, I-263, I-264, I-265, I-266, I-267, I-276, I-277, I-278, I-279, I-282, I-283, I-286, I-287, I-288, I-290, I-291, I-292, I-293, I-294, I-295, I-296, I-297, I-298, I-299, I-300, I-301, I-302, I-303, I-304, I-305, I-306, I-307, I-308, I-309, I-310, I-311, I-312, I-313, I-314, I-315, I-317, I-318, I-320, I-322, I-324, I-325, I-328, I-329, I-330, I-336, I-337, I-339, I-340, I-341, I-342, I-343, I-344, I-345, I-346, I-347, I-348, I-349, I-350, I-351, I-352, I-353, I-354, I-355, I-356, I-357, I-358, I-359, I-360, I-361, I-362, I-364, I-366, I-367, I-368, I-369, I-370, I-372, I-374, I-383, I-385, I-386, I-387, I-388, I-403, I-405, I-406, I-407, I-408, I-411, I-414, I-417, I-418, I-419, I-421, I-422, I-425, I-426, I-427, I-428, I-429, I-430, I-445, I-446, I-451, I-452, I-477, I-478, I-513, I-514, I-517, I-518, I-535, I-571, I-572, I-573, I-575, I-576, I-577, I-581, I-587, I-588, I-589, I-591, I-593, I-595, I-599, I-600, I I-1, I I-3, I I-4, I I-5, I I-6, I I-9, I I-11, I I-15, I I-16, I I-19, I I-20, I I-27, I I-28, I I-39, I I-40, I I-43, I I-44, I I-55, I I-57, I I-58, I I-61, I I-62, I I-77, I I-78, I I-81, I I-82, I I-85, I I-86, I I-89, I I-94, II-95, I I I-10, I I I-14, I I I-15, I V-5, I V-6, V-13, V-14, V-19, V-20, V-21, V-27, V-32, V-33, V-36, V-37, V-38, V-44, V-53, V-54, V-82, V-83, V-92, V-93, V-95, V-102, V-103, V-105, V-113, V-114, V-116, V-120, V-121, V-124, V-154, V-155, V-156, V-159, V-167, V-176, V-179, V-188, V-208, V-237, V-266, V-276, V-278, V-283, V-284, V-285, V-286, V-292, V-294, V-295, V-297, V-301, V-302, V-305, V-307, V-312, V-321, V-323, V-324, V-326, V-330, V-331, V-333, V-365, V-366, V-373, V-493, V-613, V-614, V-635, V-636, V-639, V-640, V-645, V-646, V-651, V-652, V-653, V-657, V-658, V-659, V-660, V-685, V-686, V-687, V-688, V-692, V-693, V-694, V-695, V-698, V-699, V-700, V-701, V-708, V-710, V-717 and V-718.

In contrast, Comparative Compound 1 (2-amino-6-methylthio-4-phenyl-benzene-1,3-dicarbonitrile), which is disclosed in Example 1 of East German Patent No. 142541, and Comparative Compound 2 (2-amino-6-phenyl-4-methylthio-3-nitrobenzonitrile), which is mentioned in East German Patent No. 142542, both scored preventive values of 0 in the test.

$$\text{Preventive value} = \left(1 - \frac{\begin{array}{c}\text{Number of adult mites}\\\text{in the control area}\\\text{before treatment}\end{array}}{\begin{array}{c}\text{Number of adult mites}\\\text{in the treated area}\\\text{before treatment}\end{array}} \times \frac{\begin{array}{c}\text{Number of adult mites}\\\text{in the treated area}\\\text{on the date of survey}\end{array}}{\begin{array}{c}\text{Number of adult mites}\\\text{in the control area}\\\text{on the date of survey}\end{array}}\right) \times 100 \quad \text{(Equation 1)}$$

The invention claimed is:

1. A compound represented by formula (I):

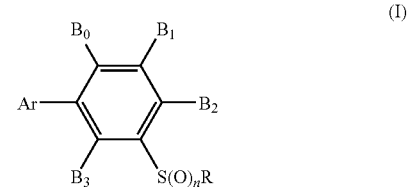

wherein
R is a $C_3$-$C_6$ alkyl group which may be mono- or poly-substituted by halogen atoms or cyano groups,
a $C_3$-$C_6$ alkenyl group which may be mono- or poly-substituted by halogen atoms or cyano groups,
a $C_3$-$C_6$ alkynyl group which may be mono- or poly-substituted by halogen atoms or cyano groups,
a $C_3$-$C_6$ cycloalkyl group which may be mono- or poly-substituted by halogen atoms or cyano groups, or
a $C_4$-$C_9$ cycloalkylalkyl group which may be mono- or poly-substituted by halogen atoms or cyano groups,
n is an integer of from 0 to 2,
Ar is a moiety represented by formula Ar-3:

wherein
$Q_6$ is a sulfur atom,
$Q_7$ is C-$A_7$,
each of $A_7$ and $B_0$ is, independently
a hydrogen atom, a halogen atom,
an amino group,
a cyano group,
a nitro group,
a $C_1$-$C_6$ alkyl group,
a $C_1$-$C_4$ haloalkyl group,
a $C_1$-$C_6$ alkylthio group which may be mono- or poly-substituted by halogen atoms or
a $C_1$-$C_6$ alkoxy group,
each of $A_6$, $A_9$, $B_1$, $B_2$ and $B_3$ is, independently
a hydrogen atom,
a halogen atom,
a cyano group,
a nitro group,
a $C_1$-$C_6$ alkyl group which may be mono- or poly-substituted by halogen atoms, hydroxyl groups, cyano groups, $C_2$-$C_7$ alkoxycarbonyl groups or $C_1$-$C_6$ alkoxy groups,
a $C_2$-$C_6$ alkenyl group which may be mono- or poly-substituted by halogen atoms or cyano groups,
a $C_2$-$C_6$ alkynyl group which may be mono- or poly-substituted by halogen atoms or cyano groups,
a $C_1$-$C_6$ alkoxy group which may be mono- or poly-substituted by halogen atoms, cyano groups, $C_2$-$C_5$ alkoxycarbonyl groups or $C_1$-$C_3$ alkoxy groups,
a $C_1$-$C_6$ alkylthio group which may be mono- or poly-substituted by halogen atoms or $C_1$-$C_3$ alkoxy groups,
a $C_1$-$C_6$ alkylsulfinyl group which may be mono- or poly substituted by halogen atoms or $C_1$-$C_3$ alkoxy groups,
a $C_1$-$C_6$ alkylsulfonyl group which may be mono- or poly-substituted by halogen atoms or $C_1$-$C_3$ alkoxy groups,
a $C_1$-$C_7$ acyl group,
a $C_2$-$C_5$ haloalkylcarbonyl group,
a carboxyl group,
a $C_2$-$C_7$ alkoxycarbonyl group or
$NR_1R_2$
wherein $R_1$ and $R_2$ are independently hydrogen atoms, $C_1$-$C_6$ alkyl groups which may be mono- or poly-substituted by halogen atoms, cyano groups, hydroxyl groups, $C_1$-$C_6$ alkoxy groups or $C_1$-$C_6$ alkylthio groups, $C_2$-$C_6$ alkenyl groups which may be mono- or poly-substituted by halogen atoms or cyano groups, $C_2$-$C_6$ alkynyl groups which may be mono-or poly-substituted by halogen atoms or cyano groups, $C_1$-$C_7$ acyl groups or $C_2$-$C_7$ alkoxycarbonyl groups or may form a 5 to 6-membered ring together with the nitrogen atom attached thereto.

2. The compound according to claim 1, wherein $A_7$ is a hydrogen atom, and
R is a n-propyl group which may be mono- or poly-substituted by halogen atoms or a cyclopropylmethyl group which may be mono- or poly-substituted by halogen atoms.

3. The compound according to claim 1, wherein $Q_7$ is C—H.

4. The compound according to claim 1, wherein
R is a n-propyl group or a $CH_2$-cyclopropyl group; and
n is 0 or 1.

5. The compound according to claim 1, wherein
$A_6$ is H; $A_9$ is one of H, Cl, and $CF_3$; $B_0$, $B_1$ and $B_3$ are each H; $B_2$ is one of CN, CHO, and $CH_3$; R is a n-propyl group or a $CH_2$-cyclopropyl group; and n is 0 or 1.

6. The compound according to claim 1, wherein
$A_6$ is H; $A_9$ is one of H, Cl, and $CF_3$; $B_0$, $B_1$ and $B_3$ are each H; and $B_2$ is one of CN, CHO, and $CH_3$.

7. The compound according to claim 1, which is:

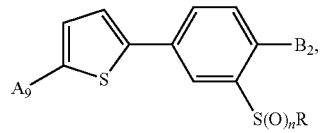

where
$A_9$ is one of H, Cl, and $CF_3$;
$B_2$ is one of CN, CHO, and $CH_3$;
R is a n-propyl group or a $CH_2$-cyclopropyl group; and
n is 0 or 1.

8. The compound according to claim 1, which is:

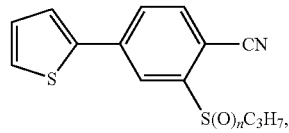

where
R is a n-propyl group or a $CH_2$-cyclopropyl group; and
n is 0 or 1.

9. The compound according to claim 1, which is

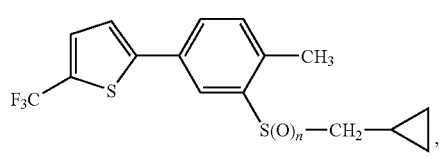

where n is 0 or 1.

10. The compound according to claim 1, which is where n is 0 or 1.

11. The compound according to claim 1, which is where n is 0 or 1.

12. The compound according to claim 1, which is

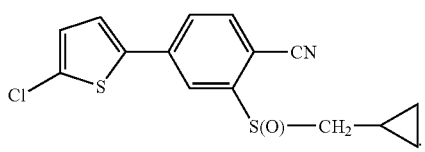

13. The compound according to claim 1, which is

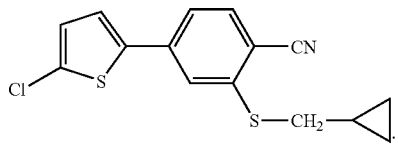

14. An insecticide or miticide comprising the compound as defined in claim 1 as an active ingredient.

15. An insecticide or miticide comprising the compound as defined in claim 2 as an active ingredient.

16. The insecticide or miticide according to claim 15, comprising from 0.1 to 50,000 ppm of said 3-arylphenyl sulfide compound as an active ingredient.

17. A method of killing a farm or garden pest insect or mites comprising contacting said insect or mites with an effective amount of the compound as defined in claim 1.

18. The method according to claim 17, wherein said effective amount is from 0.1 to 5,000 g per 1 ha.

19. A method of killing a farm or garden pest insect or mites comprising contacting said insect or mites with an effective amount of the compound as defined in claim 2.

* * * * *